(12) United States Patent
Jaeschke et al.

(10) Patent No.: US 7,951,824 B2
(45) Date of Patent: May 31, 2011

(54) 4-ARYL-PYRIDINE-2-CARBOXYAMIDE DERIVATIVES

(75) Inventors: Georg Jaeschke, Basel (CH); Will Spooren, Franken (FR); Eric Vieira, Frenkendorf (CH)

(73) Assignee: Hoffman-La Roche Inc., Nutley, NJ (US)

( * ) Notice: Subject to any disclaimer, the term of this patent is extended or adjusted under 35 U.S.C. 154(b) by 1120 days.

(21) Appl. No.: 11/699,786

(22) Filed: Jan. 30, 2007

(65) Prior Publication Data
US 2007/0197553 A1    Aug. 23, 2007

(30) Foreign Application Priority Data

Feb. 17, 2006 (EP) .................... 06110086

(51) Int. Cl.
C07D 401/12 (2006.01)
C07D 213/81 (2006.01)
A61K 31/443 (2006.01)

(52) U.S. Cl. ...... 514/333; 514/342; 546/256; 546/270.7

(58) Field of Classification Search .............. 546/256, 546/270.7; 514/333, 342
See application file for complete search history.

(56) References Cited

U.S. PATENT DOCUMENTS
6,660,753 B2  12/2003  Van Wagenen et al.

FOREIGN PATENT DOCUMENTS

| | | |
|---|---|---|
| CN | 1580056 | 2/2005 |
| EP | 0 321 115 | 6/1989 |
| EP | 1210344 | 6/2002 |
| GB | 2406856 | * 4/2005 |
| JP | 2004315395 | 11/2004 |
| WO | WO 98/05651 | 2/1998 |
| WO | WO 02/068417 | 9/2002 |
| WO | WO 03/029210 | 4/2003 |
| WO | WO 03/051315 | 6/2003 |
| WO | WO 03/051833 | 6/2003 |
| WO | WO 03/053922 | 7/2003 |
| WO | WO 03/059904 | 7/2003 |
| WO | WO 2004/058762 | 7/2004 |
| WO | 2005032493 | 4/2005 |
| WO | 2005034870 | 4/2005 |
| WO | WO 2005/044797 | 5/2005 |
| WO | WO 2005/079802 | 9/2005 |
| WO | WO 2006/008545 | 1/2006 |
| WO | WO 2006/016178 | 2/2006 |
| WO | WO 2006/039718 | 4/2006 |

OTHER PUBLICATIONS

Nan et al., CAPLUS Abstract 144:468150 (corresponds to CN 1580056 A patent document published Feb. 16, 2005).*
Kulkarni et al., Design and synthesis of novel heterobiaryl amides as metabotropic glutamate receptor subtype 5 antagonists, Bioorganic & Medicinal Chemistry Letters, 17(7), pp. 2074-2079, Jan. 4, 2007.*
Bonnefous, et al., Bioorganic & Medicinal Chemistry Letters, vol. 15, pp. 1197-1200 (2005).
Mutel, V., Expert Opinion Ther. Patents, vol. 12(12), pp. 1845-1852 (2002).
Schlaeger, et al., Cytotechnology, vol. 30: pp. 71-83 (1999).
Ahn, et al., J. Med. Chem. vol. 40, pp. 2196-2210 (1997).
Felder, E. et al Jour. of Med. Chem., 15(2), pp. 210-211 (1972).
Bonnefous, C. et al, Bioorganic & Medicinal Chem. Letters, 15(4) pp. 1197-1200 (2004).
Lynch, G. S., Expert Opin. Ther. Patents (2002), 12, pp. 11-27.
Guery et al., Synth. Commun. vol. 32 (11), (2002) pp. 1715-1719.
Fife, J. Org. Chem. vol. 48(8) (1983) pp. 1375-1377.
Fife, Heterocycles, vol. 22(1) (1984) pp. 93-95.
Goehring et al., Chimia vol. 50(11) (1996) pp. 538-543.
Schlaeger et al., Cytotechnology, vol. 30, pp. 71-83 (1999).
Porter et al., Br. J. Pharmacol. vol. 128, pp. 13-20 (1999).
Tanga et al., J. Heterocyclic Chem. vol. 34(3), pp. 717-727 (1997).
Kaye, et al., J. C. S. Perkin I, pp. 2335-2339 (1981).
Chemical Abstract XP002430655.
Suzuki et al., Synthesis, (1982) pp. 874-875.
Basha et al., Tetrahedron Lett. (1977) vol. 48, pp. 4171-4174.
Golankiewicz et al., Tetrahedron (1985) vol. 41, pp. 5989-5994.
English Language Abstract Corresponding to CN1580056, 2005.
Chemical Abstract AN:101:72495 Compound, 1984.
English Language Abstract Corresponding to JP2004/315395, 2004.
Nan et al., CAPLUS Abstract 144:468150—CN1580056 Published Feb. 16, 2005.

* cited by examiner

*Primary Examiner* — Deepak Rao
(74) *Attorney, Agent, or Firm* — George W. Johnson; Patricia S. Rocha-Tramaloni; Kimberly J. Prior

(57) ABSTRACT

The present invention relates to novel pyridine-2-carboxyamide derivatives of formula (I) useful as metabotropic glutamate receptor antagonists:

wherein Y, Z, $R^1$, $R^2$ and $R^3$ are as defined in the specification herein.

29 Claims, No Drawings

4-ARYL-PYRIDINE-2-CARBOXYAMIDE DERIVATIVES

PRIORITY TO RELATED APPLICATIONS

This application claims the benefit of European Application No. 06110086.3, filed Feb. 17, 2006, which is hereby incorporated by reference in its entirety.

BACKGROUND OF THE INVENTION

Glutamate is the major excitatory neurotransmitter in the brain and plays a unique role in a variety of central nervous system (CNS) functions. The glutamate-dependent stimulus receptors are divided into two main groups. The first main group, namely the ionotropic receptors, forms ligand-controlled ion channels. The metabotropic glutamate receptors (mGluR) belong to the second main group and, furthermore, belong to the family of G-protein coupled receptors.

At present, eight different members of the mGluR family are known and of these, some even have sub-types. According to their sequence homology, signal transduction mechanisms and agonist selectivity, these eight receptors can be sub-divided into three sub-groups: mGluR1 and mGluR5 belong to group I, mGluR2 and mGluR3 belong to group II and mGluR4, mGluR6, mGluR7 and mGluR8 belong to group III.

Ligands of metabotropic glutamate receptors belonging to the first group can be used for the treatment or prevention of acute and/or chronic neurological disorders such as psychosis, epilepsy, schizophrenia, Alzheimer's disease, cognitive disorders and memory deficits, as well as chronic and acute pain.

Other treatable indications in this connection are restricted brain function caused by bypass operations or transplants, poor blood supply to the brain, spinal cord injuries, head injuries, hypoxia caused by pregnancy, cardiac arrest and hypoglycaemia. Further treatable indications are ischemia, Huntington's chorea, amyotrophic lateral sclerosis (ALS), dementia caused by AIDS, eye injuries, retinopathy, idiopathic parkinsonism or parkinsonism caused by medicaments as well as conditions which lead to glutamate-deficiency functions, such as e.g. muscle spasms, convulsions, migraine, urinary incontinence, gastrointestinal reflux disorder, liver damage or failure whether drug or disease induced, Fragile-X syndrom, Down syndrom, autism, nicotine addiction, opiate addiction, anxiety, vomiting, dyskinesia, eating disorders such as bulimia or anorexia nervosa, and depressions.

Disorders mediated full or in part by mGluR5 are for example acute, traumatic and chronic degenerative processes of the nervous system, such as Alzheimer's disease, senile dementia, Parkinson's disease, Huntington's chorea, amyotrophic lateral sclerosis and multiple sclerosis, psychiatric diseases such as schizophrenia and anxiety, depression, pain and drug dependency (*Expert Opin. Ther. Patents* (2002), 12, (12)).

Selective mGluR5 antagonists are especially useful for the treatment of anxiety and pain.

SUMMARY OF THE INVENTION

The present invention provides novel pyridine-2-carboxyamide derivatives of the formula (I):

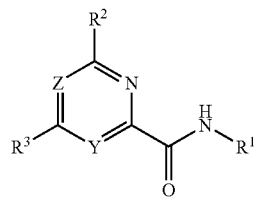

(I)

wherein
Y is C—$R^4$ and Z is CH; or
Y is C—$R^4$ and Z is N; or
Y is N and Z is CH;
$R^1$ is a 5- or 6-membered ring respectively of formula (II) or (III):

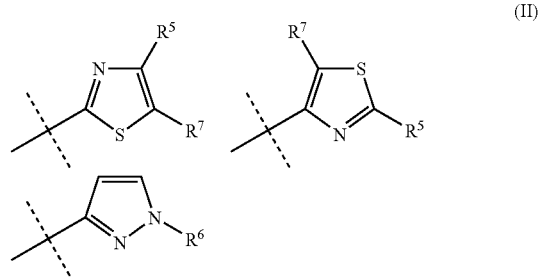

(II)

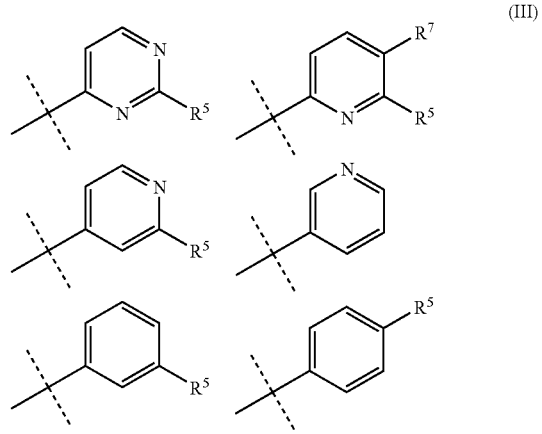

(III)

$R^2$ is H, $C_1$-$C_7$-alkyl, $C_3$-$C_6$-cycloalkyl or —$(CH_2)_m$—$R^a$;
$R^3$ is aryl or heteroaryl each of which is optionally substituted by one or more substituents selected from the group consisting of:
CN, Cl, F, Br, $CF_3$, $CHF_2$, $C_1$-$C_7$-alkyl, —O—$C_1$-$C_7$-alkyl, —(CO)—$R^b$, —$(CH_2)_m$—$R^c$, —NH—(CO)—$C_1$-$C_7$-alkyl, —O—$CH_2F$, —O—$CHF_2$, —O—$CF_3$, —$S(O)_2$—$R^d$, and —$NR^gR^h$ or is heteroaryl which is optionally substituted by $C_1$-$C_7$-alkyl;
$R^4$ is H, —OH, —$NH_2$, —NH—$C_1$-$C_7$-alkyl, Cl, F, Br, $CF_3$, $CHF_2$, $C_1$-$C_7$-alkyl, or —$(CH_2)_m$—$R^a$;
$R^5$ is H, —OH, Cl, F, Br, CN, $CF_3$, $CHF_2$, $C_1$-$C_7$-alkyl, —$C_3$-$C_6$-cycloalkyl, —O—(CO)—$C_1$-$C_7$-alkyl —$(CH_2)_m$—$R^3$, or —(CO)—$NR^iR^j$;
$R^6$ is $C_1$-$C_7$-alkyl, —$C_3$-$C_6$-cycloalkyl, $C_1$-$C_7$-alkyl-$C_3$-$C_6$-cycloalkyl, —$(CH_2)_n$—O—$R^f$, $C_3$-$C_8$-alkenyl-O—$R^f$, —$(CH_2)_n$—$NR^gR^h$, —$C_2$-$C_6$-alkenyl-$NR^gR^h$ or —$(CH_2)_n$—$R^e$;
$R^7$ is H, Cl, F, CN, or $C_1$-$C_7$-alkyl;
$R^a$ is —O—$C_1$-$C_7$-alkyl or OH;

$R^b$ is $C_1$-$C_7$-alkyl, —$NR^gR^h$ or —O—$C_1$-$C_7$-alkyl;

$R^c$ is —OH, —$NR^gR^h$ or NH—(CO)—O—$C_1$-$C_7$-alkyl;

$R^d$ is $C_1$-$C_7$-alkyl, —$NR^gR^h$, —NH—$C_1$-$C_7$-alkyl or —N-di ($C_1$-$C_7$-alkyl);

$R^e$ is —H, —$CH_2F$, —$CHF_2$, —$CF_3$, CN, $C_1$-$C_7$-alkyl, $C_1$-$C_7$-alkoxy, —(CO)—$NR^iR^j$ or —O—(CO)—$C_1$-$C_7$-alkyl;

$R^f$ is $C_1$-$C_7$-alkyl, $C_3$-$C_8$-alkenyl, $C_3$-$C_6$-cycloalkyl, phenyl, benzyl or —(CO)—R';

$R^g$ and $R^h$ are each independently H, $C_1$-$C_7$-alkyl, $C_3$-$C_6$-cycloalkyl, $C_3$-$C_8$-alkenyl, phenyl, benzyl, or —(CO)—R' or $R^g$ and $R^h$ can also, together with the nitrogen atom to which they are attached, form a 5- to 7-membered heterocyclic or heteroaryl ring each of which is optionally substituted with 1 or 2 OH;

$R^i$ and $R^j$ are each independently H or $C_1$-$C_7$-alkyl;

R' is —$NR^gR^h$, —NH—$C_1$-$C_7$-alkyl, $C_1$-$C_7$-alkyl, or $C_1$-$C_7$-alkoxy;

m is 1 to 4; and n is 2 to 6;

and pharmaceutically acceptable salts thereof.

Bonnefous et al. in "Dipyridyl amides: potent metabotropic glutamate subtype 5 (mGlu5) receptor antagonists;" *Bioorganic & Medicinal chemistry Letters*, 2005, describes compounds useful as group I metabotropic glutamate receptor antagonists but does not disclose compounds of the instant invention. Furthermore, Bonnefous et al. discloses that compounds of formula (I) where $R^3$ is hydrogen, Z is —CH— and $R^1$ is pyridine-3-yl, or pyridine-4-yl are generally inactive. The reference also states that for compounds of formula (I) where $R^3$ is hydrogen, Z is —CH— and $R^1$ is pyridine-2-yl substitution was only tolerated in the position 6.

Contrary to Bonnefous, et al. the present inventors have determined that an $R^3$ substituent leads to potent mGluR5 receptor antagonists. Also contrary to Bonnefous et al., the 5-position of compounds where $R^1$ is pyridine-2-yl are indeed amenable to substitution by substituents as defined in $R^7$, and that the resulting compounds of formula I where $R^1$ is pyridine-4-yl are active as mGluR5 receptor antagonists.

The invention also provides pharmaceutical compositions containing one or more compounds of the present invention and a pharmaceutically acceptable carrier. The invention further provides methods for the manufacture of the compounds and compositions of the invention.

Compounds of general formula I are metabotropic glutamate receptor antagonists. Compounds of formula I are distinguished by having valuable therapeutic properties. They can be used in the treatment or prevention of mGluR5 receptor mediated disorders, such as acute and/or chronic neurological disorders, in particular anxiety and chronic or acute pain.

DETAILED DESCRIPTION OF THE INVENTION

The following definitions of general terms used in the present description apply irrespective of whether the terms in question appear alone or in combination. It must be noted that, as used in the specification and the appended claims, the singular forms "a", "an," and "the" include plural forms unless the context clearly dictates otherwise.

"Aryl" means a monovalent cyclic aromatic hydrocarbon moiety consisting of a mono-, bi- or tricyclic aromatic ring. Preferred aryl groups are $C_6$-$C_{10}$ aryl. The aryl group can be optionally substituted as defined herein. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof.

"$C_1$-$C_7$ alkyl" denotes a straight- or branched-hydrocarbon chain containing from 1 to 7 carbon atoms, for example, methyl, ethyl, propyl, isopropyl, isobutyl, sec-butyl, tert-butyl, pentyl, and n-hexyl as well as those specifically illustrated by the examples herein below.

"$C_1$-$C_7$ alkoxy" denotes a $C_1$-$C_7$ alkyl group as described hereinabove, which is linked to the rest of the molecule via an oxygen atom. Examples of $C_1$-$C_7$-alkoxy groups are methoxy and ethoxy, as well as those specifically illustrated by the examples herein below.

"$C_1$-$C_7$ alkenyl" or "$C_3$-$C_8$ alkenyl" denote a straight- or branched-hydrocarbon chain containing from 1 to 7 or from 3 to 8 carbon atoms, respectively which contains at least one double bond. Examples of such alkenyl groups include ethenyl, propenyl, prop-2-enyl well as those specifically illustrated by the examples herein below.

"Halogen" denotes chlorine, iodine, fluorine and bromine.

"Heteroaryl" means a monocyclic, bicyclic or tricyclic radical of 5 to 12, preferably 5 to 9, ring atoms having at least one aromatic ring and furthermore containing one, two, or three ring heteroatoms selected from N, O, and S, the remaining ring atoms being C. Heteroaryl can optionally be substituted with one, two, three or four substituents, wherein each substituent is independently hydroxy, cyano, alkyl, alkoxy, thioalkyl, halo, haloalkyl, hydroxyalkyl, alkoxycarbonyl, amino, acetyl, —$NHCOOC(CH_3)_3$ or halogen substituted benzyl, or for the non aromatic part of cyclic ring also by oxo, unless otherwise specifically indicated. Examples of heteroaryl moieties include, but are not limited to, optionally substituted imidazolyl, optionally substituted oxazolyl, optionally substituted thiazolyl, optionally substituted pyrazinyl, optionally substituted pyrrolyl, optionally substituted pyrazinyl, optionally substituted pyridinyl, optionally substituted pyrimdinyl, optionally substituted indonyl, optionally substituted isoquinolinyl, optionally substituted carbazol-9-yl, optionally substituted furanyl, optionally substituted benzofuranyl, optionally substituted benzo[1,2,3] thiadiazolyl, optionally substituted benzo[b]thiophenyl, optionally substituted 9H-thioxanthenyl, optionally substituted thieno[2,3-c]pyridinyl and the like or those which are specifically exemplified herein.

"$C_3$-$C_6$ cycloalkyl" denotes an alicyclic carbon ring having 3 to 6 carbon atoms as ring members and includes, but is not limited to, cyclopropyl, cyclobutyl, cyclopentyl, cyclohexyl, as well as those groups specifically illustrated by the examples herein below.

"5- to 7-membered heterocyclic" denotes a saturated cyclic ring comprising from 1 to 6 carbon atoms as ring members, the remaining ring members being selected from one or more of O, N and S. The term heterocycloalkyl as used herein is synonymous with heterocyclic. Preferred 5 to 7 membered heterocycloalkyl groups are 5 or 6 membered heterocycloalkyl groups. Examples of 5 to 7 and 5 or 6 membered heterocycloalkyl groups include, but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiomorpholinyl, thiomorpholinylsulfoxide, thiomorpholinylsulfone, dihydroquinolinyl, dihydrisoquinolinyl, tetrahydroquinolinyl, tetrahydroisoquinolinyl, 1-oxo-thiomorpholin, 1,1-dioxo-thiomorpholin, 1,4-diazepane, 1,4-oxazepane as well as those groups specifically illustrated by the examples herein below.

"Pharmaceutically acceptable" such as pharmaceutically acceptable carrier, excipient, etc., means pharmacologically acceptable and substantially non-toxic to the subject to which the particular compound is administered.

The term "pharmaceutically acceptable salts" embraces salts with inorganic and organic acids, which include but are not limited to hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid.

"Therapeutically effective amount" means an amount that is effective to prevent, alleviate or ameliorate symptoms of disease or prolong the survival of the subject being treated.

The present invention provides novel pyridine-2-carboxamide derivatives of the formula (I):

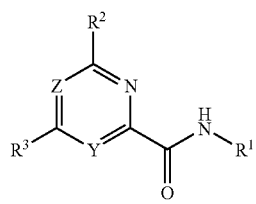

(I)

wherein

Y is C—$R^4$ and Z is CH; or

Y is C—$R^4$ and Z is N; or

Y is N and Z is CH;

$R^1$ is a 5- or 6-membered ring respectively of formula (II) or (III):

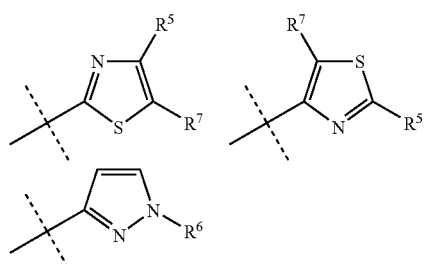

(II)

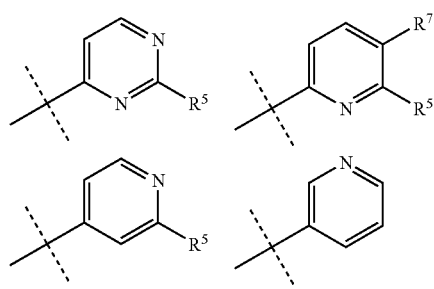

(III)

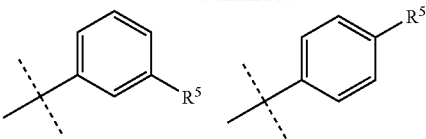

$R^2$ is H, $C_1$-$C_7$-alkyl, $C_3$-$C_6$-cycloalkyl or —$(CH_2)_m$—$R^a$;

$R^3$ is aryl or heteroaryl each of which is optionally substituted by one or more substituents selected from the group consisting of:
CN, Cl, F, Br, $CF_3$, $CHF_2$, $C_1$-$C_7$-alkyl, —O—$C_1$-$C_7$-alkyl, —(CO)—$R^b$, —$(CH_2)_m$—$R^c$, —NH—(CO)—$C_1$-$C_7$-alkyl, —O—$CH_2F$, —O—$CHF_2$, —O—$CF_3$, —$S(O)_2$—$R^d$, and —$NR^gR^h$ or is heteroaryl which is optionally substituted by $C_1$-$C_7$-alkyl;

$R^4$ is H, —OH, —$NH_2$, —NH—$C_1$-$C_7$-alkyl, Cl, F, $CF_3$, $CHF_2$, $C_1$-$C_7$-alkyl, or —$(CH_2)_m$—$R^a$;

$R^5$ is H, —OH, Cl, F, Br, CN, $CF_3$, $CHF_2$, $C_1$-$C_7$-alkyl, —$C_3$-$C_6$-cycloalkyl, —O—(CO)—$C_1$-$C_7$-alkyl —$(CH_2)_m$—$R^e$, or —(CO)—$NR^iR^j$;

$R^6$ is $C_1$-$C_7$-alkyl, —$C_3$-$C_6$-cycloalkyl, $C_1$-$C_7$-alkyl-$C_3$-$C_6$-cycloalkyl, —$(CH_2)_n$—O—$R^f$, $C_3$-$C_8$-alkenyl-O—$R^f$, —$(CH_2)_n$—$NR^gR^h$, —$C_2$-$C_6$-alkenyl-$NR^gR^h$ or —$(CH_2)_n$—$R^e$;

$R^7$ is H, Cl, F, CN, or $C_1$-$C_7$-alkyl;

$R^a$ is —O—$C_1$-$C_7$-alkyl or OH;

$R^b$ is $C_1$-$C_7$-alkyl, —$NR^gR^h$ or —O—$C_1$-$C_7$-alkyl;

$R^c$ is —OH, —$NR^gR^h$ or NH—(CO)—O—$C_1$-$C_7$-alkyl;

$R^d$ is $C_1$-$C_7$-alkyl, —$NR^gR^h$, —NH—$C_1$-$C_7$-alkyl or —N-di($C_1$-$C_7$-alkyl);

$R^e$ is —OH, —$CH_2F$, —$CHF_2$, —$CF_3$, CN, $C_1$-$C_7$-alkyl, $C_1$-$C_7$-alkoxy, —(CO)—$NR^iR^j$ or —O—(CO)—$C_1$-$C_7$-alkyl;

$R^f$ is $C_1$-$C_7$-alkyl, $C_3$-$C_6$-alkenyl, $C_3$-$C_6$-cycloalkyl, phenyl, benzyl or —(CO)—R';

$R^g$ and $R^h$ are each independently H, $C_1$-$C_7$-alkyl, $C_3$-$C_6$-cycloalkyl, $C_3$-$C_8$-alkenyl, phenyl, benzyl, or —(CO)—R' or $R^g$ and $R^h$ can also, together with the nitrogen atom to which they are attached, form a 5- to 7-membered heterocyclic or heteroaryl ring each of which is optionally substituted with 1 or 2 OH;

$R^i$ and $R^j$ are each independently H or $C_1$-$C_7$-alkyl;

R' is —$NR^gR^h$, —NH—$C_1$-$C_7$-alkyl, $C_1$-$C_7$-alkyl, or $C_1$-$C_7$-alkoxy;

m is 1 to 4; and n is 2 to 6;

and pharmaceutically acceptable salts thereof.

In all the embodiments described herein, alone or in combination and independent from the other groups, Y is C—$R^4$ and Z is CH, or Y is C—$R^4$ and Z is N or Y is N and Z is CH.

In all the embodiments described herein, alone or in combination and independent from the other groups, $R^2$ is preferably H or $C_1$-$C_7$-alkyl, for example methyl.

In all the embodiments described herein, alone or in combination and independent from the other groups, $R^3$ is preferably selected from substituted or unsubstituted phenyl, pyrazolyl, isoxazolyl, pyridinyl, pyrimidinyl, pyrazynyl, wherein the substituents are as described in these embodiments, for example one, two, three or four substituents independently selected from the group consisting of CN, Cl, F, $CF_3$, $C_1$-$C_7$-alkyl, —O—$C_1$-$C_7$-alkyl, —$(CH_2)_m$—$R^c$, —O—$CF_3$ and —$S(O)_2$—$R^d$.

In all the embodiments described herein, alone or in combination and independent from the other groups, $R^4$ is preferably H or $C_1$-$C_7$-alkyl, for example methyl.

In all the embodiments described herein, alone or in combination and independent from the other groups, $R^5$ is preferably H, Cl, CN, $CF_3$, $CHF_2$, $C_1$-$C_7$-alkyl, $C_3$-$C_6$-cycloalkyl, —O(CO)—$C_1$-$C_7$-alkyl, —$(CH_2)_m$—$R^e$ or —(CO)—$NR^iR^j$.

In all the embodiments described herein, alone or in combination and independent from the other groups, $R^6$ is preferably $C_1$-$C_7$-alkyl or —$(CH_2)_m$—$R^e$.

In all the embodiments described herein, alone or in combination and independent from the other groups, $R^7$ is preferably H, Cl, F, CN or $C_1$-$C_7$-alkyl.

In all the embodiments described hereinafter, alone or in combination and independent from the other groups, $R^c$ is preferably OH.

In all the embodiments described herein, alone or in combination and independent from the other groups, $R^d$ is preferably $C_1$-$C_7$-alkyl.

In all the embodiments described herein, alone or in combination and independent from the other groups, $R^e$ is preferably —$CF_3$, CN, $C_1$-$C_7$-alkoxy, —O(CO)—$C_1$-$C_7$-alkyl or —(CO)—$NR^iR^j$.

In all the embodiments described herein, alone or in combination and independent from the other groups, m is preferably 1.

Also encompassed by the compounds of formula (I) are those compounds of formula (I'):

(I')

wherein
Z is N or CH;
$R^1$ is a 5- or 6-membered ring respectively of formula (II') or (III'):

(II)

(III)

$R^2$ is H, $C_1$-$C_7$-alkyl, $C_3$-$C_6$-cycloalkyl or —$(CH_2)_m$—$R^a$;

$R^3$ is aryl or heteroaryl each of which is optionally substituted by one or more:
CN, Cl, F, Br, $CF_3$, $CHF_2$, —O—$C_1$-$C_7$-alkyl, —(CO)—$R^b$, —$(CH_2)_m$—$R^c$, —NH—(CO)—$C_1$-$C_7$-alkyl, —O—$CH_2F$, —O—$CHF_2$, —O—$CF_3$, —$S(O)_2$—$R^d$, or —$NR^gR^h$ or is heteroaryl which is optionally substituted by $C_1$-$C_7$-alkyl;

$R^4$ is H, —OH, —$NH_2$, —NH—$C_1$-$C_7$-alkyl, Cl, F, Br, $CF_3$, $CHF_2$, $C_1$-$C_7$-alkyl, or —$(CH_2)_m$—$R^a$ $R^5$ is H, —OH, Cl, F, Br, CN, $CF_3$, $CHF_2$, $C_1$-$C_7$-alkyl, —$C_3$-$C_6$-cycloalkyl —O—(CO)—$C_1$-$C_7$-alkyl or —$(CH_2)_m$—$R^e$;

$R^6$ is $C_1$-$C_7$-alkyl, —$C_3$-$C_6$-cycloalkyl, $C_1$-$C_7$-alkyl-$C_3$-$C_6$-cycloalkyl, —$(CH_2)_n$—O—$R^f$, $C_3$-$C_8$-alkenyl-O—$R^f$, —$(CH_2)_n$—$NR^gR^h$, —$C_2$-$C_6$-alkenyl-$NR^gR^h$ or —$(CH_2)_n$—$R^e$;

$R^7$ is H or F;

$R^a$ is —O—$C_1$-$C_7$-alkyl or OH;

$R^b$ is $C_1$-$C_7$-alkyl, —$NR^gR^h$ or —O—$C_1$-$C_7$-alkyl;

$R^c$ is —OH, —$NR^gR^h$ or NH—(CO)—O—$C_1$-$C_7$-alkyl;

$R^d$ is $C_1$-$C_7$-alkyl, —$NR^gR^h$, —NH—$C_1$-$C_7$-alkyl or —N-di($C_1$-$C_7$-alkyl);

$R^e$ is —OH, —$CH_2F$, —$CHF_2$, —$CF_3$ or —O—(CO)—$C_1$-$C_7$-alkyl;

$R^f$ is $C_1$-$C_7$-alkyl, $C_3$-$C_8$-alkenyl, $C_3$-$C_6$-cycloalkyl, phenyl, benzyl or —(CO)—R';

$R^g$ and $R^h$ are each independently H, $C_1$-$C_7$-alkyl, $C_3$-$C_6$-cycloalkyl, $C_3$-$C_8$-alkenyl, phenyl, benzyl, or —(CO)—R' or $R^g$ and $R^h$ can also, together with the nitrogen atom to which they are attached, form a 5- to 7-membered heterocyclic or heteroaryl ring each of which is optionally substituted with 1 or 2 OH;

R' is —$NR^gR^h$, —NH—$C_1$-$C_7$-alkyl, $C_1$-$C_7$-alkyl, or $C_1$-$C_7$-alkoxy;

m is 1 to 4; and n is 2 to 6;

and pharmaceutically acceptable salts thereof.

In certain embodiments, the compounds of formula (I') according to the invention are those following compounds of formulae (Ia') (Ib') (Ic') (Id') (Ie') (If') (Ig') and (Ih'):

(Ia')

(Ib')

-continued

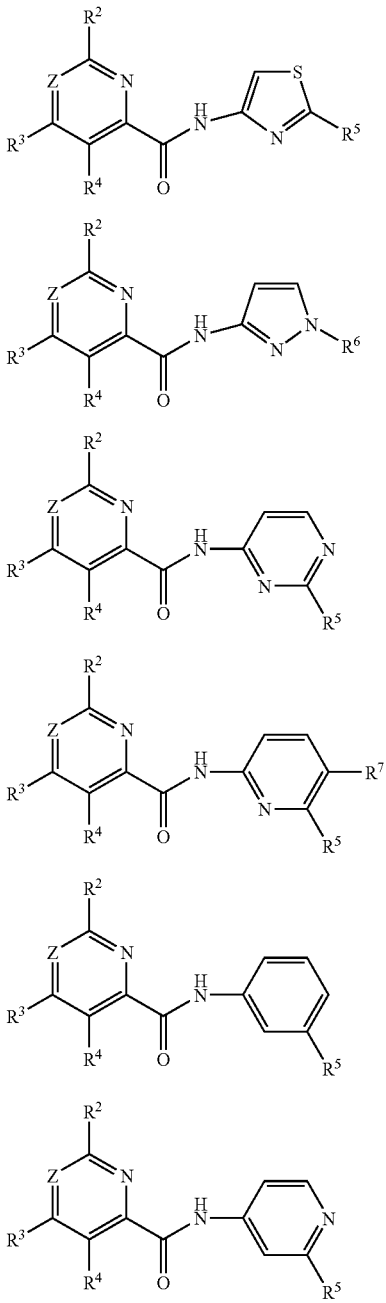

(Ic')

(Id')

(Ie')

(If')

(Ig')

(Ih')

wherein Z, $R^2$, $R^3$, $R^4$, $R^5$, $R^6$ and $R^7$ are as defined hereinabove for formula (I').

In certain embodiments, the compounds of formula (Ia') according to the invention are those compounds wherein:
Z is N or CH;
$R^2$ is H or $C_1$-$C_7$-alkyl;
$R^3$ is heteroaryl which is optionally substituted by CN, Cl, F, Br, $CF_3$, $CHF_2$, —O—$C_1$-$C_7$-alkyl, —(CO)—$R^b$, —$(CH_2)_m$—$R^c$, —NH—(CO)—$C_1$-$C_7$-alkyl, —O—$CH_2F$, —O—$CHF_2$, —O—$CF_3$, or —$S(O)_2$—$R^d$ or is heteroaryl which is optionally substituted by $C_1$-$C_7$-alkyl;
$R^4$ is H, Cl, OH, methyl or hydroxymethyl;
$R^5$ is H, Cl, F, $CF_3$, $CHF_2$, $C_1$-$C_7$-alkyl, $C_3$-$C_6$-cycloalkyl, or —$(CH_2)_m$—$R^e$;
preferably $C_1$-$C_7$-alkyl, $CF_3$, or —$(CH_2)_m$—$R^e$; and $R^6$, $R^7$, $R^b$, $R^c$, $R^d$, $R^e$ and m are as defined hereinabove for formula (I').

In certain embodiments, the compounds of formula (Ib') according to the invention are those compounds wherein:
Z is N or CH;
$R^2$ is H or $C_1$-$C_7$-alkyl;
$R^3$ is heteroaryl which is optionally substituted by CN, Cl, F, Br, $CF_3$, $CHF_2$, —O—$C_1$-$C_7$-alkyl, —(CO)—$R^b$, —$(CH_2)_m$—$R^c$, —NH—(CO)—$C_1$-$C_7$-alkyl, —O—$CH_2F$, —O—$CHF_2$, —O—$CF_3$, or —$S(O)_2$—$R^d$ or heteroaryl which is optionally substituted by $C_1$-$C_7$-alkyl;
$R^4$ is H, Cl, OH, methyl or hydroxymethyl;
$R^5$ is H, Cl, F, $CF_3$, $CHF_2$, $C_1$-$C_7$-alkyl, $C_3$-$C_6$-cycloalkyl, or —$(CH_2)_m$—$R^e$;
preferably $C_1$-$C_7$-alkyl, $CF_3$, or —$(CH_2)_m$—$R^e$; and
$R^b$, $R^c$, $R^d$, $R^e$ and m are as defined for formula (I') hereinabove, and pharmaceutically acceptable salts thereof.

In certain embodiments, the compounds of formula (Ic') according to the invention are those compounds wherein:
Z is N or CH;
$R^2$ is H or $C_1$-$C_7$-alkyl;
$R^3$ is heteroaryl which is optionally substituted by CN, Cl, F, Br, $CF_3$, $CHF_2$, —O—$C_1$-$C_7$-alkyl, —(CO)—$R^b$, —$(CH_2)_m$—$R^c$, —NH—(CO)—$C_1$-$C_7$-alkyl, —O—$CH_2F$, —O—$CHF_2$, —O—$CF_3$, or —$S(O)_2$—$R^d$ or is heteroaryl which is optionally substituted by $C_1$-$C_7$-alkyl;
$R^4$ is H, Cl, OH, methyl or hydroxymethyl;
$R^5$ is H, Cl, F, $CF_3$, $CHF_2$, $C_1$-$C_7$-alkyl, $C_3$-$C_6$-cycloalkyl, or —$(CH_2)_m$—$R^e$;
preferably $C_1$-$C_7$-alkyl, $CF_3$, or —$(CH_2)_m$—$R^e$; and
$R^b$, $R^c$, $R^d$, $R^e$ and m are as defined hereinabove for formula (I').

In certain embodiments, the compounds of formula (Id') according to the invention are those compounds wherein:
Z is N or CH;
$R^2$ is H or $C_1$-$C_7$-alkyl;
$R^3$ is heteroaryl which is optionally substituted by CN, Cl, F, Br, $CF_3$, $CHF_2$, —O—$C_1$-$C_7$-alkyl, —(CO)—$R^b$, —$(CH_2)_m$—$R^c$, —NH—(CO)—$C_1$-$C_7$-alkyl, —O—$CH_2F$, —O—$CHF_2$, —O—$CF_3$, or —$S(O)_2$—$R^d$ or is heteroaryl which is optionally substituted by $C_1$-$C_7$-alkyl;
$R^4$ is H, Cl, OH, methyl or hydroxymethyl;
$R^6$ is $C_1$-$C_7$-alkyl, $C_3$-$C_6$-cycloalkyl, or —$(CH_2)_n$—$R^e$; preferably $C_1$-$C_7$-alkyl or —$(CH_2)_n$—$R^e$; and
$R^b$, $R^c$, $R^d$, m, and n are as defined hereinabove for formula (I'), and pharmaceutically acceptable salts thereof.

In certain embodiments, the compounds of formula (Ie') according to the invention are those compounds wherein:
Z is N or CH;
$R^2$ is H or $C_1$-$C_7$-alkyl;
$R^3$ is heteroaryl which is optionally substituted by CN, Cl, F, Br, $CF_3$, $CHF_2$, —O—$C_1$-$C_7$-alkyl, —(CO)—$R^b$, —$(CH_2)_m$—$R^c$, —NH—(CO)—$C_1$-$C_7$-alkyl, —O—$CH_2F$, —O—$CHF_2$, —O—$CF_3$, or —$S(O)_2$—$R^d$ or is heteroaryl which is optionally substituted by $C_1$-$C_7$-alkyl;
$R^4$ is H, Cl, OH, methyl or hydroxymethyl;
$R^5$ is H, Cl, F, $CF_3$, $CHF_2$, $C_1$-$C_7$-alkyl, $C_3$-$C_6$-cycloalkyl, or —$(CH_2)_m$—$R^e$;
preferably $C_1$-$C_7$-alkyl, $CF_3$, or —$(CH_2)_m$—$R^e$; and
$R^b$, $R^c$, $R^d$ and m are as defined hereinabove for formula (I'), and pharmaceutically acceptable salts thereof.

In certain embodiments, the compounds of formula (If') according to the invention are those compounds wherein:

Z is N or CH;
$R^2$ is H or $C_1$-$C_7$-alkyl;
$R^3$ is heteroaryl which is optionally substituted by CN, Cl, F, Br, $CF_3$, $CHF_2$, —O—$C_1$-$C_7$-alkyl, —(CO)—$R^b$, —($CH_2$)$_m$—$R^c$, —NH—(CO)—$C_1$-$C_7$-alkyl, —O—$CH_2$F, —O—$CHF_2$, —O—$CF_3$, or —S(O)$_2$—$R^d$ or is heteroaryl which is optionally substituted by $C_1$-$C_7$-alkyl;
$R^4$ is H, Cl, OH, methyl or hydroxymethyl;
$R^5$ is H, Cl, F, $CF_3$, $CHF_2$, $C_1$-$C_7$-alkyl, $C_3$-$C_6$-cycloalkyl, or —($CH_2$)$_m$—$R^e$;
preferably Cl, $C_1$-$C_7$-alkyl, $CF_3$, or —($CH_2$)$_m$—$R^e$;
$R^7$ is H or F; and
$R^b$, $R^c$, $R^d$, $R^e$ and m are as defined hereinabove for formula (I'), and pharmaceutically acceptable salts thereof.

In any one of the embodiments recited hereinabove in the compounds of formula (If') according to the invention $R^5$ is preferably H when $R^7$ is F.

In certain embodiments, the compounds of formula (Ig') according to the invention are those compounds wherein:

Z is N or CH;
$R^2$ is H or $C_1$-$C_7$-alkyl;
$R^3$ is aryl or heteroaryl each of which is optionally substituted by CN, Cl, F, Br, $CF_3$, $CHF_2$, —O—$C_1$-$C_7$-alkyl, —(CO)—$R^b$, —($CH_2$)$_m$—$R^c$, —NH—(CO)—$C_1$-$C_7$-alkyl, —O—$CH_2$F, —O—$CHF_2$, —O—$CF_3$, or —S(O)$_2$—$R^d$ or is heteroaryl which is optionally substituted by $C_1$-$C_7$-alkyl;
$R^4$ is H, Cl, OH, methyl or hydroxymethyl;
$R^5$ is H, Cl, F, Br, $CF_3$, CN, $C_1$-$C_7$-alkyl, —O—(CO)—$C_1$-$C_7$-alkyl or —($CH_2$)$_m$—$R^e$; and
$R^b$, $R^c$, $R^d$, $R^e$ and m are as defined hereinabove for formula (I').

In certain embodiments, the compounds of formula (Ih') according to the invention are those compounds wherein:

Z is N or CH;
$R^2$ is H or $C_1$-$C_7$-alkyl;
$R^3$ is aryl or heteroaryl each of which is optionally substituted by CN, Cl, F, Br, $CF_3$, $CHF_2$, —O—$C_1$-$C_7$-alkyl, —(CO)—$R^b$, —($CH_2$)$_m$—$R^c$, —NH—(CO)—$C_1$-$C_7$-alkyl, —O—$CH_2$F, —O—$CHF_2$, —O—$CF_3$, or —S(O)$_2$—$R^d$ or is heteroaryl which is optionally substituted by $C_1$-$C_7$-alkyl;
$R^4$ is H, Cl, OH, methyl or hydroxymethyl;
$R^5$ is —OH, Cl, F, Br, $CF_3$, CN, $C_1$-$C_7$-alkyl, —O—(CO)—$C_1$-$C_7$-alkyl or ($CH_2$)$_m$—$R^e$;
preferably Cl, $CF_3$, CN or $C_1$-$C_7$-alkyl; and
$R^b$, $R^c$, $R^d$, $R^e$ and m are as defined hereinabove for formula (I').

Also encompassed by the compounds of formula (I) are those compounds wherein
Y is C—$R^4$ and Z is CH; or
Y is C—$R^4$ and Z is N; or
Y is N and Z is CH;
$R^1$ is as defined for formula (I) hereinabove;
$R^2$ is H or $C_1$-$C_7$-alkyl;
$R^3$ is aryl or heteroaryl each of which is optionally substituted by one or more substituents independently selected from the group consisting of CN, Cl, F, $CF_3$, $C_1$-$C_7$-alkyl, —O—$C_1$-$C_7$-alkyl, —($CH_2$)$_m$—$R^c$, —O—$CF_3$, or —S(O)$_2$—$R^d$;
$R^4$ is H or $C_1$-$C_7$-alkyl;
$R^5$ is H, Cl, CN, $CF_3$, $CHF_2$, $C_1$-$C_7$-alkyl, $C_3$-$C_6$-cycloalkyl, —O(CO)—$C_1$-$C_7$-alkyl, —($CH_2$)$_m$—$R^e$ or —(CO)—NR$^i$R$^j$;
$R^6$ is $C_1$-$C_7$-alkyl or —($CH_2$)$_m$—$R^e$;
$R^7$ is H, Cl, F, CN, or $C_1$-$C_7$-alkyl;
$R^c$ is OH;
$R^d$ is $C_1$-$C_7$-alkyl;
$R^e$ is —$CF_3$, CN, $C_1$-$C_7$-alkoxy, —O(CO)—$C_1$-$C_7$-alkyl or —(CO)—NR$^i$R$^j$;
$R^i$ and $R^j$ are each independently H or $C_1$-$C_7$-alkyl; and
m is 1;
and pharmaceutically acceptable salts thereof.

Also encompassed by the compounds of formula (I) are those compounds of formulae (Ia), (Ib), (Ic), (Id), (Ie), (If), (Ig), (Ih) and (Ii):

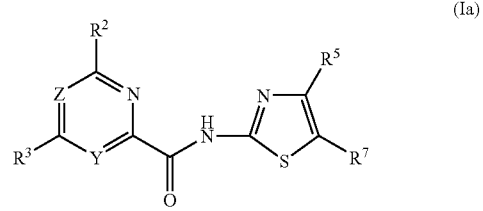
(Ia)

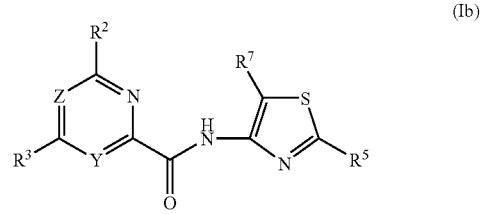
(Ib)

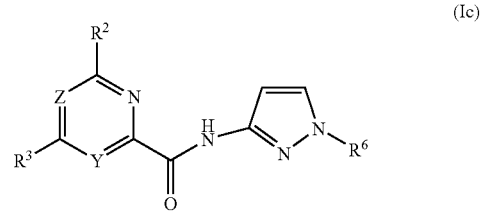
(Ic)

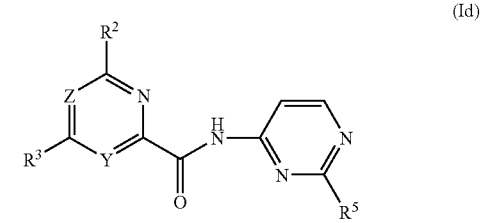
(Id)

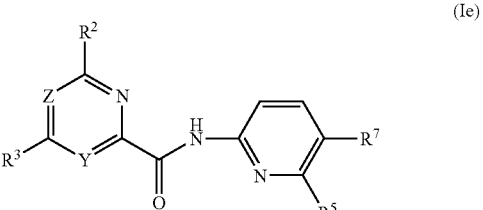
(Ie)

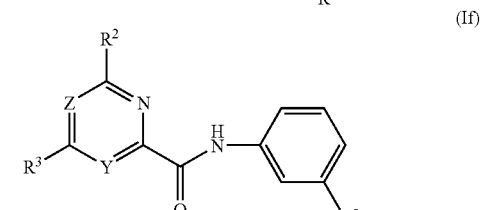
(If)

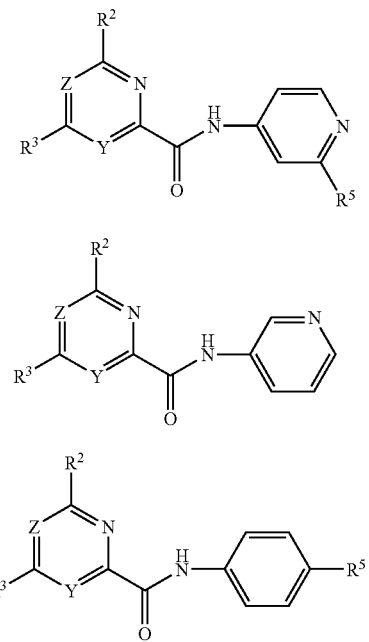

wherein Y, Z, $R^2$, $R^3$, $R^5$, $R^6$ and $R^7$ are as defined hereinabove for formula (I).

An example of compound of formula (Ia) according to the invention is:

4-(3-Fluoro-phenyl)-6-methyl-pyridine-2-carboxylic acid (4-methyl-thiazol-2-yl)-amide;
4-(3,5-Difluoro-phenyl)-6-methyl-pyridine-2-carboxylic acid (4-methyl-thiazol-2-yl)-amide;
4-(3-Cyano-phenyl)-6-methyl-pyridine-2-carboxylic acid (4-methyl-thiazol-2-yl)-amide;
6-Chloro-6'-methyl-[3,4']bipyridinyl-2'-carboxylic acid (4-methyl-thiazol-2-yl)-amide;
4-(2,5-Difluoro-phenyl)-6-methyl-pyridine-2-carboxylic acid (4-methyl-thiazol-2-yl)-amide;
4-(3-Methoxy-phenyl)-6-methyl-pyridine-2-carboxylic acid (4-methyl-thiazol-2-yl)-amide;
6-Methyl-4-(3-trifluoromethoxy-phenyl)-pyridine-2-carboxylic acid (4-methyl-thiazol-2-yl)-amide;
4-(3-Methanesulfonyl-phenyl)-6-methyl-pyridine-2-carboxylic acid (4-methyl-thiazol-2-yl)-amide;
4-(4-Methoxy-phenyl)-6-methyl-pyridine-2-carboxylic acid (4-methyl-thiazol-2-yl)-amide;
4-(3,4-Difluoro-phenyl)-6-methyl-pyridine-2-carboxylic acid (4-methyl-thiazol-2-yl)-amide;
6-Methyl-4-(3,4,5-trifluoro-phenyl)-pyridine-2-carboxylic acid (4-methyl-thiazol-2-yl)-amide;
4-(4-Cyano-phenyl)-6-methyl-pyridine-2-carboxylic acid (4-methyl-thiazol-2-yl)-amide;
4-(2-Methoxy-phenyl)-6-methyl-pyridine-2-carboxylic acid (4-methyl-thiazol-2-yl)-amide;
4-(2-Chloro-phenyl)-6-methyl-pyridine-2-carboxylic acid (4-methyl-thiazol-2-yl)-amide;
4-(3-Hydroxymethyl-phenyl)-6-methyl-pyridine-2-carboxylic acid (4-methyl-thiazol-2-yl)-amide;
6'-Methyl-[3,4']bipyridinyl-2'-carboxylic acid (4-methyl-thiazol-2-yl)-amide;
4-(3,5-Dichloro-phenyl)-6-methyl-pyridine-2-carboxylic acid (4-methyl-thiazol-2-yl)-amide;
6-Methyl-4-pyrimidin-5-yl-pyridine-2-carboxylic acid (4-methyl-thiazol-2-yl)-amide;
5-Fluoro-6'-methyl-[3,4']bipyridinyl-2'-carboxylic acid (4-methyl-thiazol-2-yl)-amide;
4-(4-Fluoro-phenyl)-6-methyl-pyridine-2-carboxylic acid (4-methyl-thiazol-2-yl)-amide;
6-(3,5-Difluoro-phenyl)-2-methyl-pyrimidine-4-carboxylic acid (4-methyl-thiazol-2-yl)-amide;
2-Methyl-6-pyridin-3-yl-pyrimidine-4-carboxylic acid (4-methyl-thiazol-2-yl)-amide;
4-(2,5-Dimethyl-2H-pyrazol-3-yl)-6-methyl-pyridine-2-carboxylic acid (4-methyl-thiazol-2-yl)-amide;
2'-Chloro-6-methyl-[4,4']bipyridinyl-2-carboxylic acid (4-methyl-thiazol-2-yl)-amide;
6'-Methyl-[2,4']bipyridinyl-2'-carboxylic acid (4-methyl-thiazol-2-yl)-amide;
6-Methyl-4-(3-trifluoromethyl-phenyl)-pyridine-2-carboxylic acid (4-methyl-thiazol-2-yl)-amide;
2-Chloro-6'-methyl-[3,4']bipyridinyl-2'-carboxylic acid (4-methyl-thiazol-2-yl)-amide;
5-Cyano-6'-methyl-[3,4']bipyridinyl-2'-carboxylic acid (4-methyl-thiazol-2-yl)-amide;
4-(3,5-Dimethyl-isoxazol-4-yl)-6-methyl-pyridine-2-carboxylic acid (4-methyl-thiazol-2-yl)-amide;
4,6'-Dimethyl-[3,4']bipyridinyl-2'-carboxylic acid (4-methyl-thiazol-2-yl)-amide;
5-Methoxy-6'-methyl-[3,4']bipyridinyl-2'-carboxylic acid (4-methyl-thiazol-2-yl)-amide;
6-Fluoro-6'-methyl-[3,4']bipyridinyl-2'-carboxylic acid (4-methyl-thiazol-2-yl)-amide;
2'-Chloro-6-methyl-[4,4']bipyridinyl-2-carboxylic acid (4-methyl-thiazol-2-yl)-amide;
4-(3,5-Difluoro-phenyl)-6-methyl-pyridine-2-carboxylic acid (4-trifluoromethyl-thiazol-2-yl)-amide;
5-Fluoro-6'-methyl-[3,4']bipyridinyl-2'-carboxylic acid (4-trifluoromethyl-thiazol-2-yl)-amide;
4-(3-Fluoro-phenyl)-6-methyl-pyridine-2-carboxylic acid (4-trifluoromethyl-thiazol-2-yl)-amide;
4-(3-Cyano-phenyl)-6-methyl-pyridine-2-carboxylic acid (4-trifluoromethyl-thiazol-2-yl)-amide;
4-(2-Chloro-phenyl)-6-methyl-pyridine-2-carboxylic acid (4-trifluoromethyl-thiazol-2-yl)-amide;
6'-Methyl-[3,4']bipyridinyl-2'-carboxylic acid (4-trifluoromethyl-thiazol-2-yl)-amide;
2'-Chloro-6-methyl-[4,4']bipyridinyl-2-carboxylic acid (4-trifluoromethyl-thiazol-2-yl)-amide;
4-(2,5-Dimethyl-2H-pyrazol-3-yl)-6-methyl-pyridine-2-carboxylic acid (4-trifluoromethyl-thiazol-2-yl)-amide;
6'-Methyl-[3,4']bipyridinyl-2'-carboxylic acid (4-difluoromethyl-thiazol-2-yl)-amide;
2'-Chloro-6-methyl-[4,4']bipyridinyl-2-carboxylic acid (4-difluoromethyl-thiazol-2-yl)-amide;
4-(3-Chloro-4-fluoro-phenyl)-3,6-dimethyl-pyridine-2-carboxylic acid (4-methyl-thiazol-2-yl)-amide;
4-(3,5-Difluoro-phenyl)-3,6-dimethyl-pyridine-2-carboxylic acid (4-methyl-thiazol-2-yl)-amide;
5-Fluoro-3',6'-dimethyl-[3,4']bipyridinyl-2'-carboxylic acid (4-methyl-thiazol-2-yl)-amide;
4-(4-Fluoro-phenyl)-3,6-dimethyl-pyridine-2-carboxylic acid (4-methyl-thiazol-2-yl)-amide;
3',6'-Dimethyl-[3,4']bipyridinyl-2'-carboxylic acid (4-methyl-thiazol-2-yl)-amide;
3,6-Dimethyl-4-pyrimidin-5-yl-pyridine-2-carboxylic acid (4-methyl-thiazol-2-yl)-amide;
4-(3,4-Difluoro-phenyl)-3,6-dimethyl-pyridine-2-carboxylic acid (4-methyl-thiazol-2-yl)-amide;

4-(2,5-Dimethyl-2H-pyrazol-3-yl)-3,6-dimethyl-pyridine-2-carboxylic acid (4-methyl-thiazol-2-yl)-amide;
2'-Chloro-3,6-dimethyl-[4,4']bipyridinyl-2-carboxylic acid (4-methyl-thiazol-2-yl)-amide;
3,6,2'-Trimethyl-[4,4']bipyridinyl-2-carboxylic acid (4-methyl-thiazol-2-yl)-amide;
6'-Methyl-5-trifluoromethyl-[3,4']bipyridinyl-2'-carboxylic acid (4-methyl-thiazol-2-yl)-amide;
2'-Fluoro-6-methyl-[4,4']bipyridinyl-2-carboxylic acid (4-methyl-thiazol-2-yl)-amide;
6-Methyl-4-pyrazin-2-yl-pyridine-2-carboxylic acid (4-methyl-thiazol-2-yl)-amide;
2,6'-Dimethyl-[3,4']bipyridinyl-2'-carboxylic acid (4-methyl-thiazol-2-yl)-amide;
6,2'-Dimethyl-[4,4']bipyridinyl-2-carboxylic acid (4-methyl-thiazol-2-yl)-amide;
6-Methyl-2-trifluoromethyl-[4,4]bipyridinyl-2-carboxylic acid (4-methyl-thiazol-2-yl)-amide;
2'-Cyano-6-methyl-[4,4']bipyridinyl-2-carboxylic acid (4-methyl-thiazol-2-yl)-amide;
6'-Cyano-6,2'-dimethyl-[4,4']bipyridinyl-2-carboxylic acid (4-methyl-thiazol-2-yl)-amide;
2'-Chloro-5'-fluoro-6-methyl-[4,4']bipyridinyl-2-carboxylic acid (4-methyl-thiazol-2-yl)-amide;
5,6'-Dimethyl-[3,4']bipyridinyl-2'-carboxylic acid (4-methyl-thiazol-2-yl)-amide;
4-(3,5-Difluoro-phenyl)-6-methyl-pyridine-2-carboxylic acid (4-cyanomethyl-thiazol-2-yl)-amide;
4-(3,5-Difluoro-phenyl)-6-methyl-pyridine-2-carboxylic acid (4-difluoromethyl-thiazol-2-yl)-amide;
4-(3,5-Difluoro-phenyl)-6-methyl-pyridine-2-carboxylic acid (4-cyano-thiazol-2-yl)-amide;
4-(3,5-Difluoro-phenyl)-6-methyl-pyridine-2-carboxylic acid (4-methoxymethyl-thiazol-2-yl)-amide;
5-Fluoro-6'-methyl-[3,4']bipyridinyl-2'-carboxylic acid (4-difluoromethyl-thiazol-2-yl)-amide;
5-Fluoro-6'-methyl-[3,4']bipyridinyl-2'-carboxylic acid (4-cyano-thiazol-2-yl)-amide;
5-Fluoro-6'-methyl-[3,4']bipyridinyl-2'-carboxylic acid (4-cyclopentyl-thiazol-2-yl)-amide;
6,2'-Dimethyl-[4,4']bipyridinyl-2-carboxylic acid (4-cyano-thiazol-2-yl)-amide;
6,2'-Dimethyl-[4,4']bipyridinyl-2-carboxylic acid (4-methoxymethyl-thiazol-2-yl)-amide;
6,2'-Dimethyl-[4,4']bipyridinyl-2-carboxylic acid (4-methyl-thiazol-2-yl)-amide;
2-{[4-(3,5-Difluoro-phenyl)-6-methyl-pyridine-2-carbonyl]-amino}-thiazole-4-carboxylic acid methyl ester;
4-(3,5-Difluoro-phenyl)-6-methyl-pyridine-2-carboxylic acid (4-methylcarbamoyl-thiazol-2-yl)-amide;
4-(3,5-Difluoro-phenyl)-6-methyl-pyrimidine-2-carboxylic acid (4-methyl-thiazol-2-yl)-amide;
4-(3,5-Difluoro-phenyl)-6-methyl-pyridine-2-carboxylic acid (4-methoxymethyl-thiazol-2-yl)-amide;
6,2'-Dimethyl-[4,4']bipyridinyl-2-carboxylic acid (4-methoxymethyl-thiazol-2-yl)-amide;
4-(3,5-Difluoro-phenyl)-6-methyl-pyridine-2-carboxylic acid (4-methoxymethyl-thiazol-2-yl)-amide;
6,2'-Dimethyl-[4,4']bipyridinyl-2-carboxylic acid (4-methoxymethyl-thiazol-2-yl)-amide;
4-(3,5-Difluoro-phenyl)-6-methyl-pyridine-2-carboxylic acid (5-methyl-thiazol-2-yl)-amide;
5-Fluoro-6'-methyl-[3,4']bipyridinyl-2'-carboxylic acid (4-methoxymethyl-thiazol-2-yl)-amide;
5-Fluoro-6'-methyl-[3,4']bipyridinyl-2'-carboxylic acid (4-cyanomethyl-thiazol-2-yl)-amide; or
5-Fluoro-6'-methyl-[3,4']bipyridinyl-2'-carboxylic acid (5-fluoro-thiazol-2-yl)-amide.

An example of compound of formula (Ib) according to the invention is:
4-(3,5-Dichloro-phenyl)-6-methyl-pyridine-2-carboxylic acid (2-methyl-thiazol-4-yl)-amide;
4-(3-Chloro-4-fluoro-phenyl)-6-methyl-pyridine-2-carboxylic acid (2-methyl-thiazol-4-yl)-amide;
4-(3,4-Difluoro-phenyl)-6-methyl-pyridine-2-carboxylic acid (2-methyl-thiazol-4-yl)-amide;
6-(3,5-Difluoro-phenyl)-2-methyl-pyrimidine-4-carboxylic acid (2-methyl-thiazol-4-yl)-amide;
5-Methoxy-6'-methyl-[3,4']bipyridinyl-2'-carboxylic acid (2-methyl-thiazol-4-yl)-amide;
6'-Methyl-[3,4']bipyridinyl-2'-carboxylic acid (2-methyl-thiazol-4-yl)-amide;
5-Fluoro-6'-methyl-[3,4']bipyridinyl-2'-carboxylic acid (2-methyl-thiazol-4-yl)-amide;
4-(4-Fluoro-phenyl)-6-methyl-pyridine-2-carboxylic acid (2-methyl-thiazol-4-yl)-amide;
4-(3,5-Difluoro-phenyl)-6-methyl-pyridine-2-carboxylic acid (2-methyl-thiazol-4-yl)-amide;
2'-Chloro-6-methyl-[4,4']bipyridinyl-2-carboxylic acid (2-methyl-thiazol-4-yl)-amide;
4-(2,5-Dimethyl-2H-pyrazol-3-yl)-6-methyl-pyridine-2-carboxylic acid (2-methyl-thiazol-4-yl)-amide;
4-(4-Fluoro-3-trifluoromethyl-phenyl)-6-methyl-pyridine-2-carboxylic acid (2-methyl-thiazol-4-yl)-amide;
4-(2,5-Dimethyl-2H-pyrazol-3-yl)-3,6-dimethyl-pyridine-2-carboxylic acid (2-methyl-thiazol-4-yl)-amide;
2'-Chloro-3,6-dimethyl-[4,4']bipyridinyl-2-carboxylic acid (2-methyl-thiazol-4-yl)-amide;
4-(3,5-Difluoro-phenyl)-3,6-dimethyl-pyridine-2-carboxylic acid (2-methyl-thiazol-4-yl)-amide;
3',6'-Dimethyl-[3,4']bipyridinyl-2'-carboxylic acid (2-methyl-thiazol-4-yl)-amide;
4-(3-Chloro-4-fluoro-phenyl)-3,6-dimethyl-pyridine-2-carboxylic acid (2-methyl-thiazol-4-yl)-amide;
5-Fluoro-3',6'-dimethyl-[3,4']bipyridinyl-2'-carboxylic acid (2-methyl-thiazol-4-yl)-amide;
3,6-Dimethyl-4-pyrimidin-5-yl-pyridine-2-carboxylic acid (2-methyl-thiazol-4-yl)-amide;
4-(4-Fluoro-phenyl)-3,6-dimethyl-pyridine-2-carboxylic acid (2-methyl-thiazol-4-yl)-amide;
4-(3,4-Difluoro-phenyl)-3,6-dimethyl-pyridine-2-carboxylic acid (2-methyl-thiazol-4-yl)-amide; or
2'-Fluoro-6-methyl-[4,4']bipyridinyl-2-carboxylic acid (2-methyl-thiazol-4-yl)-amide.

An example of compound of formula (Ic) according to the invention is:
4-(3,5-Dichloro-phenyl)-6-methyl-pyridine-2-carboxylic acid (1-methyl-1H-pyrazol-3-yl)-amide;
4-(3-Chloro-4-fluoro-phenyl)-6-methyl-pyridine-2-carboxylic acid (1-methyl-1H-pyrazol-3-yl)-amide;
4-(3,4-Difluoro-phenyl)-6-methyl-pyridine-2-carboxylic acid (1-methyl-1H-pyrazol-3-yl)-amide;
4-(4-Fluoro-phenyl)-6-methyl-pyridine-2-carboxylic acid (1-methyl-1H-pyrazol-3-yl)-amide;
6-(3,5-Difluoro-phenyl)-2-methyl-pyrimidine-4-carboxylic acid (1-methyl-1H-pyrazol-3-yl)-amide;
5-Methoxy-6'-methyl-[3,4']bipyridinyl-2'-carboxylic acid (1-methyl-1H-pyrazol-3-yl)-amide;
6'-Methyl-[3,4']bipyridinyl-2'-carboxylic acid (1-methyl-1H-pyrazol-3-yl)-amide;
5-Fluoro-6'-methyl-[3,4']bipyridinyl-2'-carboxylic acid (1-methyl-1H-pyrazol-3-yl)-amide;

4-(3,5-Difluoro-phenyl)-6-methyl-pyridine-2-carboxylic acid (1-methyl-1H-pyrazol-3-yl)-amide;

2'-Chloro-6-methyl-[4,4']bipyridinyl-2-carboxylic acid (1-methyl-1H-pyrazol-3-yl)-amide;

4-(4-Fluoro-3-trifluoromethyl-phenyl)-6-methyl-pyridine-2-carboxylic acid (1-methyl-1H-pyrazol-3-yl)-amide;

4-(4-Fluoro-phenyl)-3,6-dimethyl-pyridine-2-carboxylic acid (1-methyl-1H-pyrazol-3-yl)-amide;

4-(3,5-Difluoro-phenyl)-3,6-dimethyl-pyridine-2-carboxylic acid (1-methyl-1H-pyrazol-3-yl)-amide;

3',6'-Dimethyl-[3,4']bipyridinyl-2'-carboxylic acid (1-methyl-1H-pyrazol-3-yl)-amide;

3,6-Dimethyl-4-pyrimidin-5-yl-pyridine-2-carboxylic acid (1-methyl-1H-pyrazol-3-yl)-amide;

4-(3,4-Difluoro-phenyl)-3,6-dimethyl-pyridine-2-carboxylic acid (1-methyl-1H-pyrazol-3-yl)-amide;

5-Fluoro-3',6'-dimethyl-[3,4']bipyridinyl-2'-carboxylic acid (1-methyl-1H-pyrazol-3-yl)-amide;

4-(2,5-Dimethyl-2H-pyrazol-3-yl)-3,6-dimethyl-pyridine-2-carboxylic acid (1-methyl-1H-pyrazol-3-yl)-amide;

2'-Chloro-3,6-dimethyl-[4,4']bipyridinyl-2-carboxylic acid (1-methyl-1H-pyrazol-3-yl)-amide;

2'-Chloro-6-methyl-[4,4']bipyridinyl-2-carboxylic acid (1-methyl-1H-pyrazol-3-yl)-amide;

6,2'-Dimethyl-[4,4']bipyridinyl-2-carboxylic acid (1-methyl-1H-pyrazol-3-yl)-amide;

6,2',6'-Trimethyl-[4,4']bipyridinyl-2-carboxylic acid (1-methyl-1H-pyrazol-3-yl)-amide;

2'-Chloro-5'-fluoro-6-methyl-[4,4']bipyridinyl-2-carboxylic acid (1-methyl-1H-pyrazol-3-yl)-amide;

5,6'-Dimethyl-[3,4']bipyridinyl-2'-carboxylic acid (1-methyl-1H-pyrazol-3-yl)-amide;

6,2',5'-Trimethyl-[4,4']bipyridinyl-2-carboxylic acid (1-methyl-1H-pyrazol-3-yl)-amide;

6'-Cyano-6,2'-dimethyl-[4,4']bipyridinyl-2-carboxylic acid (1-methyl-1H-pyrazol-3-yl)-amide;

2'-Cyano-6-methyl-[4,4']bipyridinyl-2-carboxylic acid (1-methyl-1H-pyrazol-3-yl)-amide;

(3-{[4-(3,5-Difluoro-phenyl)-6-methyl-pyridine-2-carbonyl]-amino}-pyrazol-1-yl)-acetic ethyl ester;

4-(3,5-Difluoro-phenyl)-6-methyl-pyridine-2-carboxylic acid [1-(2,2,2-trifluoro-ethyl)-1H-pyrazol-3-yl]-amide;

6-Methyl-4-pyrimidin-5-yl-pyridine-2-carboxylic acid (1-methyl-1H-pyrazol-3-yl)-amide;

4-(3,5-Difluoro-phenyl)-6-methyl-pyridine-2-carboxylic acid (1-carbamoylmethyl-1H-pyrazol-3-yl)-amide;

4-(3,5-Difluoro-phenyl)-6-methyl-pyridine-2-carboxylic acid (1-cyanomethyl-1H-pyrazol-3-yl)-amide; or 4-(3,5-Difluoro-phenyl)-6-methyl-pyrimidine-2-carboxylic acid (1-methyl-1H-pyrazol-3-yl)-amide.

An example of compound of formula (Id) according to the invention is:

4-(4-Fluoro-phenyl)-6-methyl-pyridine-2-carboxylic acid (2-methyl-pyrimidin-4-yl)-amide;

4-(3,5-Difluoro-phenyl)-6-methyl-pyridine-2-carboxylic acid (2-methyl-pyrimidin-4-yl)-amide;

6'-Methyl-[3,4']bipyridinyl-2'-carboxylic acid (2-methyl-pyrimidin-4-yl)-amide;

5-Fluoro-6'-methyl-[3,4']bipyridinyl-2'-carboxylic acid (2-methyl-pyrimidin-4-yl)-amide;

4-(3,5-Difluoro-phenyl)-6-methyl-pyridine-2-carboxylic acid (4-chloro-pyrimidin-2-yl)-amide;

4-(3,5-Difluoro-phenyl)-6-methyl-pyridine-2-carboxylic acid (2-chloro-pyrimidin-4-yl)-amide;

2'-Chloro-6-methyl-[4,4']bipyridinyl-2-carboxylic acid (2-methyl-pyrimidin-4-yl)-amide; or 4-(3,5-Difluoro-phenyl)-6-methyl-pyrimidine-2-carboxylic acid (2-methyl-pyrimidin-4-yl)-amide.

An example of compound of formula (Ie) according to the invention is:

6'-Methyl-[3,4']bipyridinyl-2'-carboxylic acid (6-methyl-pyridin-2-yl)-amide;

6'-Methyl-[3,4']bipyridinyl-2'-carboxylic acid (6-chloro-pyridin-2-yl)-amide;

4-(3,5-Difluoro-phenyl)-3,6-dimethyl-pyridine-2-carboxylic acid (2-methyl-pyridin-4-yl)-amide;

5-Fluoro-3',6'-dimethyl-[3,4']bipyridinyl-2'-carboxylic acid (2-methyl-pyridin-4-yl)-amide;

3',6'-Dimethyl-[3,4']bipyridinyl-2'-carboxylic acid (2-methyl-pyridin-4-yl)-amide;

4-(3-Chloro-4-fluoro-phenyl)-3,6-dimethyl-pyridine-2-carboxylic acid (2-methyl-pyridin-4-yl)-amide;

4-(3,5-Difluoro-phenyl)-3,6-dimethyl-pyridine-2-carboxylic acid (2-chloro-pyridin-4-yl)-amide;

4-(3,5-Difluoro-phenyl)-6-methyl-pyridine-2-carboxylic acid (5-cyano-pyridin-2-yl)-amide;

4-(3,5-Difluoro-phenyl)-6-methyl-pyridine-2-carboxylic acid (5-methyl-pyridin-2-yl)-amide;

5-Fluoro-6'-methyl-[3,4']bipyridinyl-2'-carboxylic acid (5-chloro-pyridin-2-yl)-amide;

2'-Chloro-6-methyl-[4,4']bipyridinyl-2-carboxylic acid (6-methyl-pyridin-2-yl)-amide;

2'-Chloro-6-methyl-[4,4']bipyridinyl-2-carboxylic acid (5-chloro-pyridin-2-yl)-amide; or 2'-Chloro-6-methyl-[4,4']bipyridinyl-2-carboxylic acid (5-methyl-pyridin-2-yl)-amide.

An example of compound of formula (If) according to the invention is:

4-(4-Fluoro-phenyl)-6-methyl-pyridine-2-carboxylic acid (3-chloro-phenyl)-amide;

6'-Methyl-[3,4']bipyridinyl-2'-carboxylic acid (3-cyano-phenyl)-amide;

4-(3,5-Difluoro-phenyl)-6-methyl-pyridine-2-carboxylic acid (3-cyano-phenyl)-amide;

5-Fluoro-6'-methyl-[3,4']bipyridinyl-2'-carboxylic acid (3-cyano-phenyl)-amide;

6,2'-Dimethyl-[4,4']bipyridinyl-2-carboxylic acid (3-cyano-phenyl)-amide;

5-Fluoro-6'-methyl-[3,4']bipyridinyl-2'-carboxylic acid (3-chloro-phenyl)-amide;

5-Fluoro-6'-methyl-[3,4']bipyridinyl-2'-carboxylic acid (4-fluoro-phenyl)-amide; or 5-Fluoro-6'-methyl-[3,4']bipyridinyl-2'-carboxylic acid phenylamide.

An example of compound of formula (Ig) according to the invention is:

4-(4-Fluoro-phenyl)-6-methyl-pyridine-2-carboxylic acid (2-methyl-pyridin-4-yl)-amide;

4-(4-Fluoro-phenyl)-6-methyl-pyridine-2-carboxylic acid (2-chloro-pyridin-4-yl)-amide;

6-(3,5-Difluoro-phenyl)-2-methyl-pyrimidine-4-carboxylic acid (2-chloro-pyridin-4-yl)-amide;

6-(3,5-Difluoro-phenyl)-2-methyl-pyrimidine-4-carboxylic acid (2-methyl-pyridin-4-yl)-amide;

5-Fluoro-6'-methyl-[3,4']bipyridinyl-2'-carboxylic acid (2-chloro-pyridin-4-yl)-amide;

4-(3,4-Difluoro-phenyl)-6-methyl-pyridine-2-carboxylic acid (2-chloro-pyridin-4-yl)-amide;

6'-Methyl-[3,4']bipyridinyl-2'-carboxylic acid (2-chloro-pyridin-4-yl)-amide;
4-(3,5-Difluoro-phenyl)-6-methyl-pyridine-2-carboxylic acid (2-chloro-pyridin-4-yl)-amide;
4-(3-Chloro-4-fluoro-phenyl)-6-methyl-pyridine-2-carboxylic acid (2-chloro-pyridin-4-yl)-amide;
4-(3,4-Difluoro-phenyl)-6-methyl-pyridine-2-carboxylic acid (2-methyl-pyridin-4-yl)-amide;
5-Fluoro-6'-methyl-[3,4']bipyridinyl-2'-carboxylic acid (2-methyl-pyridin-4-yl)-amide;
4-(3-Chloro-4-fluoro-phenyl)-6-methyl-pyridine-2-carboxylic acid (2-methyl-pyridin-4-yl)-amide;
6'-Methyl-[3,4']bipyridinyl-2'-carboxylic acid (2-methyl-pyridin-4-yl)-amide;
4-(3,5-Difluoro-phenyl)-6-methyl-pyridine-2-carboxylic acid (2-methyl-pyridin-4-yl)-amide;
5-Cyano-6'-methyl-[3,4']bipyridinyl-2'-carboxylic acid (2-methyl-pyridin-4-yl)-amide;
4-(2,5-Dimethyl-2H-pyrazol-3-yl)-6-methyl-pyridine-2-carboxylic acid (5-chloro-pyridin-2-yl)-amide;
4-(3,5-Difluoro-phenyl)-6-methyl-pyridine-2-carboxylic acid (5-chloro-pyridin-2-yl)-amide;
4-(3-Chloro-4-fluoro-phenyl)-6-methyl-pyridine-2-carboxylic acid (5-chloro-pyridin-2-yl)-amide;
6'-Methyl-[3,4']bipyridinyl-2'-carboxylic acid (5-chloro-pyridin-2-yl)-amide;
2'-Cyano-6-methyl-[4,4']bipyridinyl-2-carboxylic acid (2-methyl-pyridin-4-yl)-amide;
6'-Cyano-6,2'-dimethyl-[4,4']bipyridinyl-2-carboxylic acid (2-methyl-pyridin-4-yl)-amide;
6,2'-Dimethyl-[4,4']bipyridinyl-2-carboxylic acid (2-methyl-pyridin-4-yl)-amide;
2'-Chloro-6-methyl-[4,4']bipyridinyl-2-carboxylic acid (2-methyl-pyridin-4-yl)-amide;
6'-Cyano-6,2'-dimethyl-[4,4']bipyridinyl-2-carboxylic acid (2-chloro-pyridin-4-yl)-amide;
2'-Cyano-6-methyl-[4,4']bipyridinyl-2-carboxylic acid (2-chloro-pyridin-4-yl)-amide;
6,2'-Dimethyl-[4,4']bipyridinyl-2-carboxylic acid (2-chloro-pyridin-4-yl)-amide;
6,2',6'-Trimethyl-[4,4']bipyridinyl-2-carboxylic acid (2-chloro-pyridin-4-yl)-amide;
5,6'-Dimethyl-[3,4']bipyridinyl-2'-carboxylic acid (2-chloro-pyridin-4-yl)-amide;
2'-Chloro-6-methyl-[4,4']bipyridinyl-2-carboxylic acid (2-chloro-pyridin-4-yl)-amide;
6,2',5'-Trimethyl-[4,4']bipyridinyl-2-carboxylic acid (2-chloro-pyridin-4-yl)-amide;
4-(3,5-Difluoro-phenyl)-6-methyl-pyridine-2-carboxylic acid (2-cyano-pyridin-4-yl)-amide;
4-(3,5-Difluoro-phenyl)-6-methyl-pyrimidine-2-carboxylic acid (2-chloro-pyridin-4-yl)-amide;
4-(3,5-Difluoro-phenyl)-6-methyl-pyrimidine-2-carboxylic acid (2-methyl-pyridin-4-yl)-amide; or
4-(3,5-Difluoro-phenyl)-6-methyl-pyrimidine-2-carboxylic acid (2-cyano-pyridin-4-yl)-amide.

An example of compound of formula (Ih) according to the invention is 5-Fluoro-6'-methyl-[3,4']bipyridinyl-2'-carboxylic acid pyridin-3-ylamide.

An example of compound of formula (Ii) according to the invention is 5-Fluoro-6'-methyl-[3,4']bipyridinyl-2'-carboxylic acid (4-fluoro-phenyl)-amide.

The invention also encompasses methods for the preparation of the compounds of the invention.

The compounds of formula (I) wherein Z is CH and Y is C—$R^4$ can be prepared according to the following method of the invention which method comprises:
reacting an amino protected compound of formula (IV):

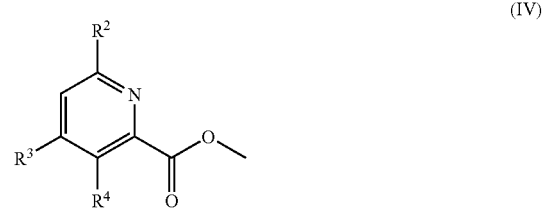

(IV)

with a compound of formula (V):

(V)

to obtain a compound of formula (I); or
reacting a compound of formula (VI)

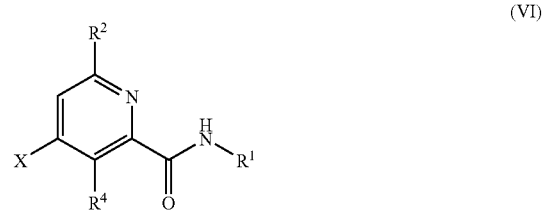

(VI)

with a compound of formula (VII):

(VII)

to obtain the compound of formula (I); or
reacting a compound of formula (VIII)

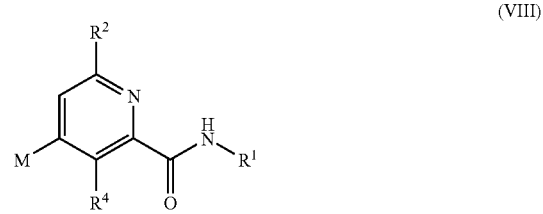

(VIII)

with a compound of formula (IX):

(IX)

to obtain the compound of formula (I)
wherein
$R^1$, $R^2$ and $R^3$ are as defined hereinabove;
X is Cl, Br (optionally also I or trifluoromethanesulfonyloxy); and
M is selected from the group consisting of trialkylsilyl, alkylfluorosilyl, alkoxysilyl, trifluoroborate, trialkylstannyl, boronic acid, boronic ester, and a zinc or magnesium containing residue such as —ZnCl, —ZnBr, —Zn(alkyl), —MgCl, —MgBr, and the like.

These methods are further described in details in scheme I and general procedure I hereafter.
Scheme 1:
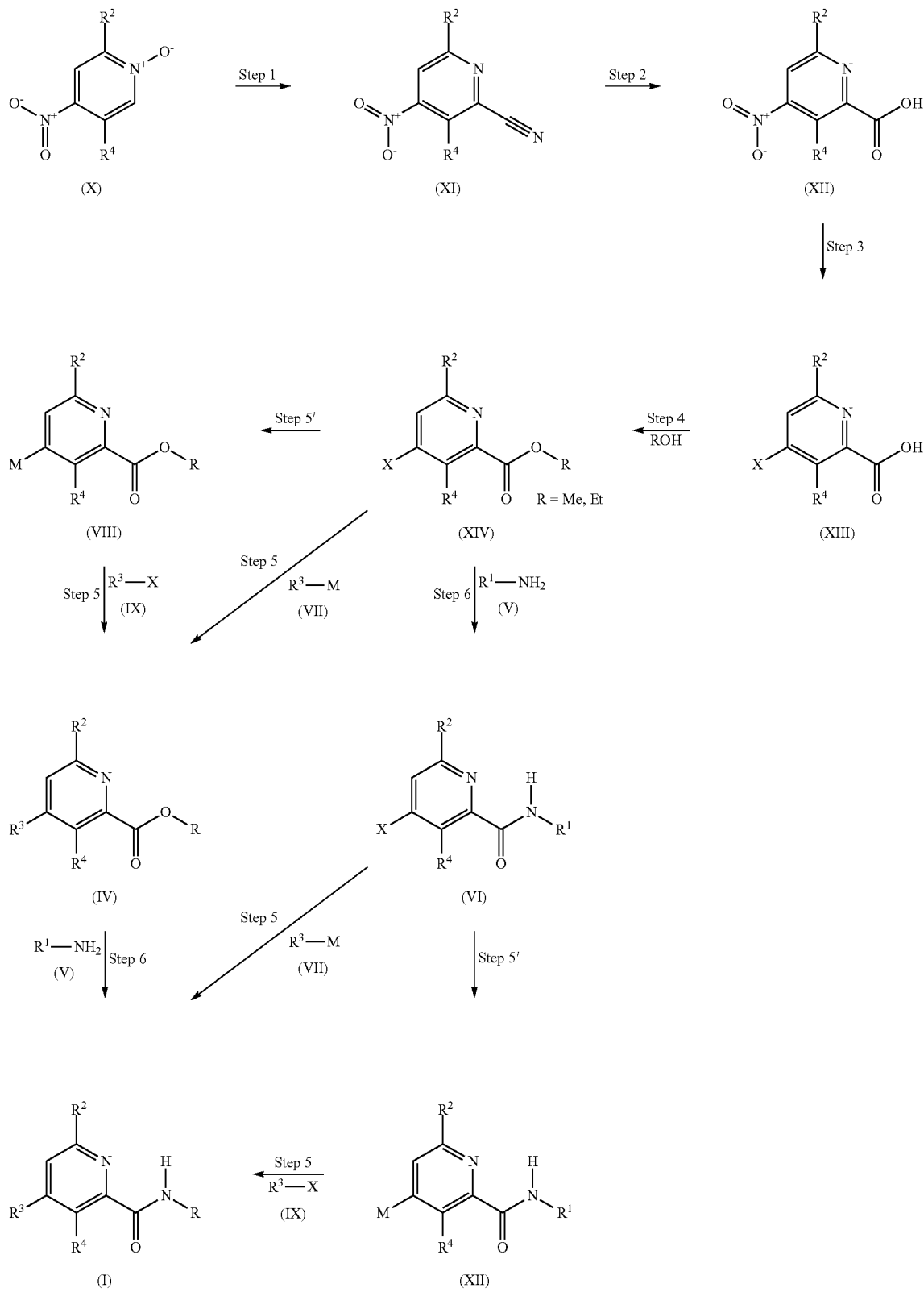

General Procedure I:

Step 1

According to a procedure described in the literature [Guery & al., Synth. Commun. 32(11), 1715(2002)] 1:1 mixture of compound (X) and dimethylsulfate is heated to 80° C. for one hour. The crude product is filtered, dissolved in water and added to an ice-cooled solution of potassium cyanide in water. The compound of formula (XI) can be isolated and purified using conventional methods.

Step 2

According to the procedure described by Guery & al., a solution of a compound of formula (XI) in 90% sulfuric acid is heated to 100° C. for two hours, cooled to room temperature, treated with sodium nitrite solution, and stirred for one hour at 80° C. The compound of formula (XII) can be isolated and purified using conventional methods.

Step 3

In analogy to the literature procedure described by Guery & al., Synth. Commun., 32(11), 1715 (2002); a solution of a compound of formula (XII) in concentrated mineral acid (HCl or HBr) is heated to 100° C. overnight. The compound of formula (XIII) can be isolated and purified using conventional methods.

Step 4

To a solution of a compound of formula (XIII) in an alcohol, preferably methanol or ethanol is added a small amount of sulfuric acid and the solution is refluxed overnight. The compound of formula (XIV) can be isolated and purified using conventional methods.

Step 5

The compound of formula (IV) can be obtained by a Palladium catalyzed coupling of the compound of formula (XIV) with a compound of formula (VII) using coupling conditions described in the chemical literature (e.g. Negishi, Hiyama, Suzuki, Stille, etc. . . . ). The compound of formula (IV) can then be isolated and purified using conventional methods.

Step 5'

The compounds of formula (IV) can also be obtained by a Palladium catalyzed coupling of the compound of formula (VIII) with a compound of formula (IX) using coupling conditions described in the chemical literature. The compound of formula (IV) can then be isolated and purified using conventional methods. The compound of formula (VIII) can be obtained from a compound of formula (XIV) using conditions described in the chemical literature. The compounds of formula (XIII) can either be isolated and purified using conventional methods, or generated in situ for the coupling step.

Step 6:

The compound of formula (I) can be obtained by reacting an amine of formula (V) with trimethylaluminium followed by treatment with a compound of formula (IV). Using the same procedure, transformation of ester (XIV) to amide (VI) is possible. It is also possible to react the carboxylic acid (XIII) directly with an amine of formula (V) in presence of a coupling reagent, or to convert the acid to its acid chloride and then react it with the amine in presence of base according to known procedures to obtain compounds of formula (VI). The compounds of formulae (I) or (VI) can then be isolated and purified using conventional methods.

As shown in scheme I, it is also possible to vary the sequence of steps 5, 5' and 6 in order to obtain the compound of formula (I). Ester (XIV) can also be transformed to the amide (VI), which is then coupled with (VII) to yield (I); or further transformed into (XII) which is then coupled with (IX) to form compound (I).

In the case where $R^4$ is not H or alkyl, the $R^4$ substituent can also be introduced at a later stage by chemical transformation of compounds of formula (I) or other suitable intermediates using procedures known to persons skilled in the art. Use of a suitable protecting group for $R^4$ which is cleaved off at the end of the synthesis is also a possible alternative for persons skilled in the art in order to obtain compounds of formula (I).

Compounds of formula (I) wherein Z is CH, and Y is C—$R^4$ can also be synthesized using procedures that are further described in details in scheme II and general procedure II hereafter.

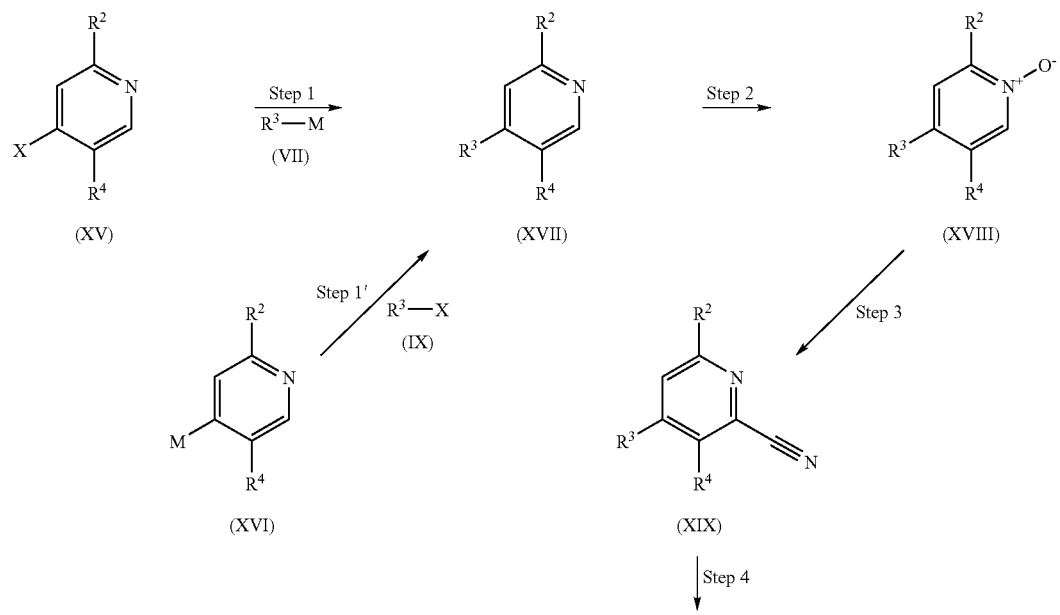

Scheme 2:

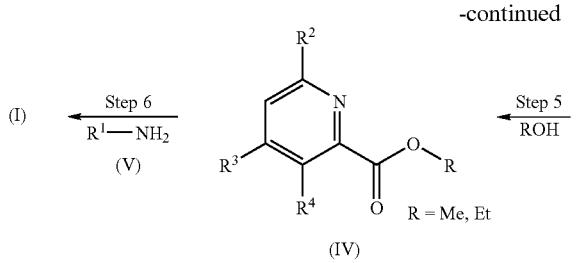

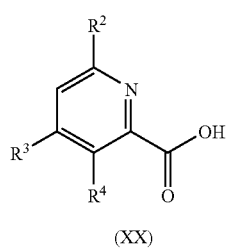

General Procedure II:

Step 1

The compound of formula (XVII) can be obtained by a Palladium catalyzed coupling of the compound of formula (XV) with a compound of formula (VII) using coupling conditions described in the chemical literature (e.g. Negishi, Hiyama, Suzuki, Stille, etc. . . . ). The compound of formula (XVII) can then be isolated and purified using conventional methods.

Step 1'

The compounds of formula (XVII) can also be obtained by a Palladium catalyzed coupling of the compound of formula (XVI) with a compound of formula (IX) using coupling conditions described in the chemical literature. The compound of formula (XVII) can then be isolated and purified using conventional methods. The compound of formula (XVI) can be obtained from a compound of formula (XV) using conditions described in the chemical literature. The compounds of formula (XVI) can either be isolated and purified using conventional methods, or generated in situ for the coupling step.

Step 2

Compounds of formula (XVII) can be oxidized to the corresponding N-oxides of formula (XVIII) using methods described in the chemical literature. Typical oxidizing agents are for example aromatic or aliphatic peracids such as m-chloroperbenzoic acid, trifluoroperacetic acid, performic acid, or peracetic acid.

Step 3

According to procedures described in the literature [Fife, J. Org. Chem. 48(8), 1375(1983); Fife, Heterocycles 22(1), 93(1984)], the compound of formula (XVIII) can be transformed into compounds of formula (XIX) using trimethylsilyl cyanide in presence of acylating agents such as N,N-dimethylcarbamoyl chloride or benzoyl chloride. The compounds of formula (XIX) can be isolated and purified using conventional methods.

Step 4

Nitriles of formula (XIX) can be hydrolysed to carboxylic acids of formula (XX) using acidic conditions such as concentrated hydrochloric or sulfuric acid, or basic conditions using sodium- or potassium hydroxide in presence or absence of an organic solvent.

Step 5

To a solution of a compound of formula (XX) in an alcohol, preferably methanol or ethanol is added a small amount of sulfuric acid and the solution is refluxed overnight. It is also possible to react the carboxylic acid (XX) directly with an alcohol in presence of a coupling reagent, or to convert the acid to its acid chloride and then react it with the alcohol in presence or absence of base according to known procedures to obtain compounds of formula (VI). The compound of formula (IV) can be isolated and purified using conventional methods. The compounds of formula (IV) can be transformed into compounds of formula (I) as described in general procedure 1.

In the case where $R^4$ is not H or alkyl, the group $R^4$ can also be introduced at a later stage by chemical transformation of compounds of formula (I) or other suitable intermediates using procedures known to persons skilled in the art. The person skilled in the art will be fully able to use a suitable protecting group for $R^4$ which will be cleaved off at the end of the synthesis as a possible alternative to obtain compounds of formula (I).

The compounds of formula (I) wherein Z is N and Y is C—$R^4$ can be prepared according to the following method of the invention which method comprises the steps of reacting a compound of formula (XXI):

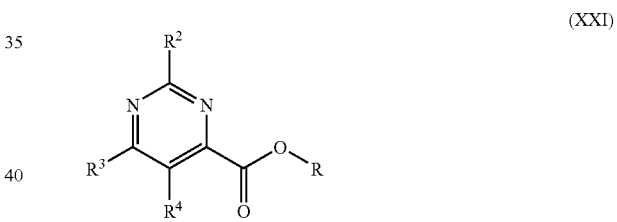

with a compound of formula (V):

R'—NH$_2$ (V)

to obtain a compound of formula (I) wherein Z is N and $R^1$ to $R^4$ are as defined hereinabove for formula (I) and R is $C_1$-$C_7$-alkyl or benzyl.

These methods are further described in details in scheme I and general procedure III hereafter.

Scheme 3:

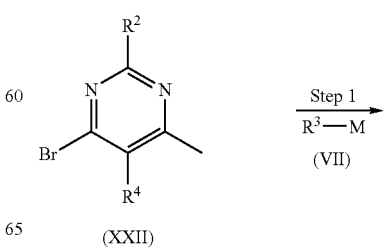

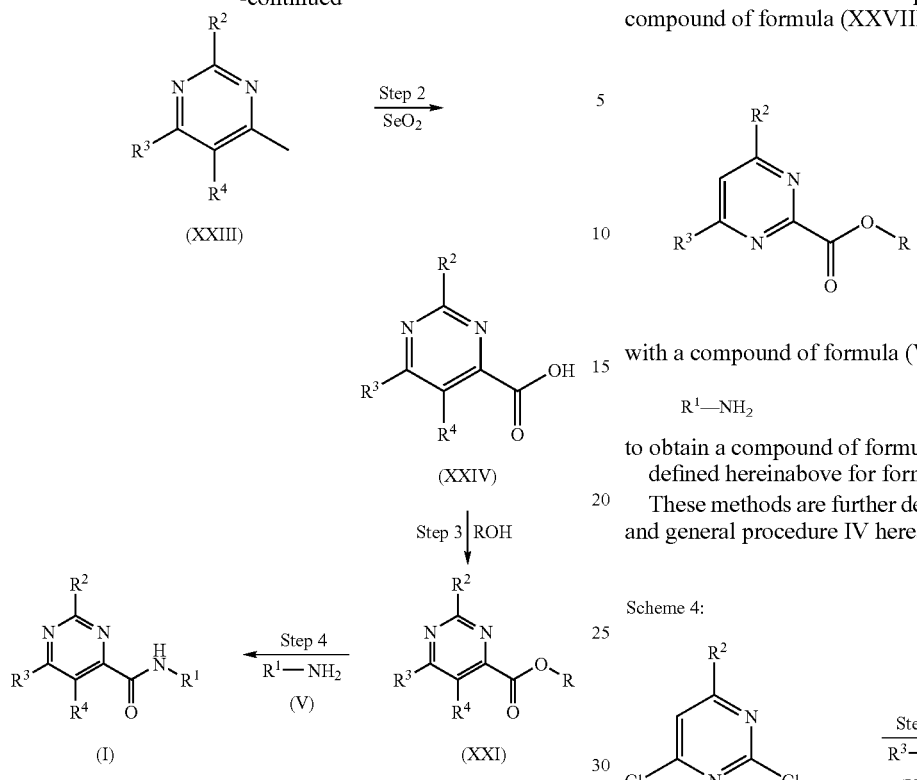

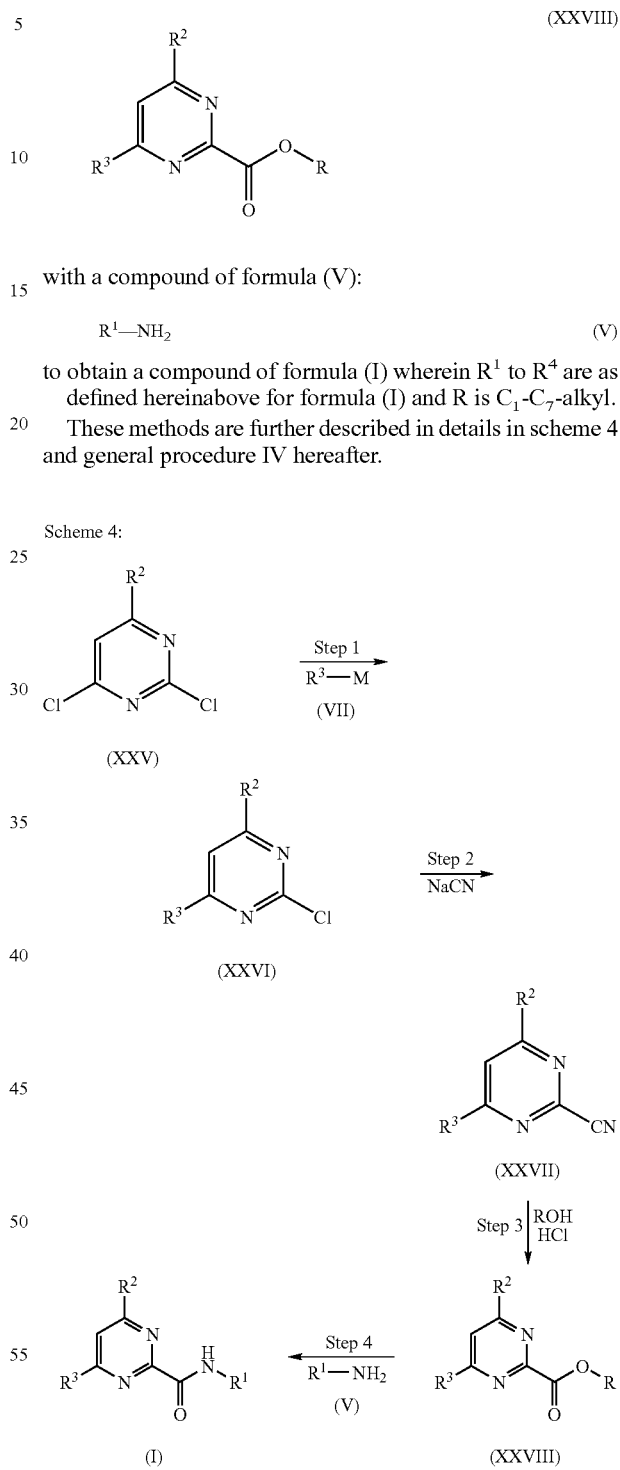

General Procedure III:
Step 1

The compound of formula (XXIII) can be obtained by a Palladium catalyzed coupling of the compound of formula (XXII) with a compound of formula (VII) using coupling conditions described in the chemical literature (e.g. Negishi, Hiyama, Suzuki, Stille, etc. . . . ). The compound of formula (XXIII) can then be isolated and purified using conventional methods.

Step 2

Compounds of formula (XVIII) can be oxidized to the corresponding carboxylic acids of formula (XXIV) using methods described in the chemical literature. Typical oxidizing agents are for example Selenium dioxide. The compounds of formula (XXIV) can then be isolated and purified using conventional methods or used directly in the next synthetic step.

Step 3

To a solution of a compound of formula (XXIV) in an alcohol, preferably methanol or ethanol is added a small amount of sulfuric acid or thionyl chloride and the solution is refluxed overnight. The compound of formula (XXI) can be isolated and purified using conventional methods.

Step 4

The compound of formula (I) can be obtained by reacting an amine of formula (V) with trimethylaluminium followed by treatment with compound (XXI). It is also possible to react the carboxylic acid (XXIV) directly with an amine of formula (V) in presence of a coupling reagent, or to convert the acid to its acid chloride and then react it with the amine in presence of base according to known procedures. The compounds of formulae (I) can then be isolated and purified using conventional methods.

The compounds of formula (I) wherein Z is CH and Y is N can be prepared according to the following method of the invention which method comprises the steps of reacting a compound of formula (XXVIII):

with a compound of formula (V):

$$R^1—NH_2 \quad (V)$$

to obtain a compound of formula (I) wherein $R^1$ to $R^4$ are as defined hereinabove for formula (I) and R is $C_1$-$C_7$-alkyl.

These methods are further described in details in scheme 4 and general procedure IV hereafter.

Scheme 4:

General Procedure IV:
Step 1

The compound of formula (XXVI) can be obtained by a Palladium catalyzed coupling of the compound of formula (XXV) with a compound of formula (VII) using coupling conditions described in the chemical literature (e.g. Negishi, Hiyama, Suzuki, Stille, etc. ...). The compound of formula (XXVI) can then be isolated and purified using conventional methods.

Step 2

In analogy to the procedure described by Goehring & al., Chimia, 50(11), 538(1996), a solution of a compound of formula (XXVI) in DMSO is treated with sodium cyanide in presence of a strong organic base such as a tertiary amine (Trimethylamine, Triethylamine, DABCO, Hünig's base and the like) to yield a compound of formula (XXVII). The compound of formula (XXVII) can be isolated and purified using conventional methods.

Step 3

Nitriles of formula (XXVII) can be transformed into carboxylic acid esters of formula (XXVIII) using acidic conditions such as saturated hydrochloric solution in an alcohol (Benzyl alcohol, Ethanol, Methanol, Isopropanol and the like, R is hence e.g. benzyl or $C_1$-$C_7$-alkyl). The compound of formula (XXVIII) can be isolated and purified using conventional methods.

Step 4

The compound of formula (I) can be obtained by reacting an amine of formula (V) with trimethylaluminium followed by treatment with an ester of formula (XXVIII). The compounds of formulae (I) can then be isolated and purified using conventional methods.

In the case where $R^4$ is not H or alkyl) the $R^4$ substituent can also be introduced at a later stage by chemical transformation of compounds of formula (I) or other suitable intermediates using procedures known to persons skilled in the art. Use of a suitable protecting group for $R^4$ which is cleaved off at the end of the synthesis is also a possible alternative for persons skilled in the art in order to obtain compounds of formula (I).

Pharmaceutically acceptable salts of compounds of formula I can be manufactured readily according to methods known per se and taking into consideration the nature of the compound to be converted into a salt. Inorganic or organic acids such as, for example, hydrochloric acid, hydrobromic acid, sulphuric acid, nitric acid, phosphoric acid or citric acid, formic acid, fumaric acid, maleic acid, acetic acid, succinic acid, tartaric acid, methanesulphonic acid, p-toluenesulphonic acid and the like are suitable for the formation of pharmaceutically acceptable salts of basic compounds of formula I. Compounds which contain the alkali metals or alkaline earth metals, for example sodium, potassium, calcium, magnesium or the like, basic amines or basic amino acids are suitable for the formation of pharmaceutically acceptable salts of acidic compounds.

As already mentioned above, the compounds of formula (I) and their pharmaceutically acceptable salts are metabotropic glutamate receptor antagonists and can be used for the treatment or prevention of mGluR5 receptor mediated disorders, such as acute and/or chronic neurological disorders, cognitive disorders and memory deficits, as well as acute and chronic pain. Treatable neurological disorders are for instance epilepsy, schizophrenia, anxiety, acute, traumatic or chronic degenerative processes of the nervous system, such as Alzheimer's disease, senile dementia, Huntington's chorea, ALS, multiple sclerosis, dementia caused by AIDS, eye injuries, retinopathy, idiopathic parkinsonism or parkinsonism caused by medicaments as well as conditions which lead to glutamate-deficient functions, such as e.g. muscle spasms, convulsions, migraine, urinary incontinence, ethanol addiction, nicotine addiction, psychoses, opiate addiction, anxiety, vomiting, dyskinesia and depression. Other treatable indications are restricted brain function caused by bypass operations or transplants, poor blood supply to the brain, spinal cord injuries, head injuries, hypoxia caused by pregnancy, cardiac arrest and hypoglycaemia. Furthermore restricted brain function leading to mental retardation due to abnormalities during pregnancy, retarded brain development or genetic anomalies such as Fragile-X syndrom, Down syndrom, or Autism spectrum disorders such as Kanner's syndrom, Pervasive developmental disorder (PDD), Attention deficit disorder (ADD) are also possible treatable indications.

The compounds of formula I and their pharmaceutically acceptable salts are especially useful as analgesics. Treatable kinds of pain include inflammatory pain such as arthritis and rheumatoid disease, vasculitis, neuropathic pain such as trigeminal or herpetic neuralgia, diabetic neuropathy pain, causalgia, hyperalgesia, severe chronic pain, post-operative pain and pain associated with various conditions like cancer, angina, renal or billiay colic, menstruation, migraine and gout.

The pharmacological activity of the compounds was tested using the following method: For binding experiments, cDNA encoding human mGlu 5a receptor was transiently transfected into EBNA cells using a procedure described by Schlaeger and Christensen [Cytotechnology 15:1-13 (1998)]. Cell membrane homogenates were stored at −80° C. until the day of assay where upon they were thawed and resuspended and polytronised in 15 mM Tris-HCl, 120 mM NaCl, 100 mM KCl, 25 mM $CaCl_2$, 25 mM $MgCl_2$ binding buffer at pH 7.4 to a final assay concentration of 20 µg protein/well.

Saturation isotherms were determined by addition of twelve [$^3$H] MPEP concentrations (0.04-100 nM) to these membranes (in a total volume of 200 µd) for 1 h at 4° C. Competition experiments were performed with a fixed concentration of [$^3$H]MPEP (2 nM) and $IC_{50}$ values of test compounds evaluated using 11 concentrations (0.3-10,000 nM). Incubations were performed for 1 h at 4° C.

At the end of the incubation, membranes were filtered onto unifilter (96-well white microplate with bonded GF/C filter preincubated 1 h in 0.1% PEI in wash buffer, Packard BioScience, Meriden, Conn.) with a Filtermate 96 harvester (Packard BioScience) and washed 3 times with cold 50 mM Tris-HCl, pH 7.4 buffer. Nonspecific binding was measured in the presence of 10 µM MPEP. The radioactivity on the filter was counted (3 min) on a Packard Top-count microplate scintillation counter with quenching correction after addition of 45 µl of microscint 40 (Canberra Packard S. A., Zürich, Switzerland) and shaking for 20 min.

For functional assays, [$Ca^{2+}$]i measurements were performed as described previously by Porter et al. [Br. J. Pharmacol. 128:13-20 (1999)] on recombinant human mGlu 5a receptors in HEK-293 cells. The cells were dye loaded using Fluo 4-AM (obtainable by FLUKA, 0.2 µM final concentration). [$Ca^{2+}$]i measurements were performed using a fluorometric imaging plate reader (FLIPR, Molecular Devices Corporation, La Jolla, Calif., USA). Antagonist evaluation was performed following a 5 min preincubation with the test compounds followed by the addition of a submaximal addition of agonist.

The inhibition (antagonists) curves were fitted with a four parameter logistic equation giving $IC_{50}$, and Hill coefficient using iterative non linear curve fitting software (Xcel fit).

For binding experiments the Ki values of the compounds tested are given. The Ki value is defined by the following formula:

$$K_i = IC_{50}/[1+L/K_d]$$

in which the $IC_{50}$ values are those concentrations of the compounds tested which cause 50% inhibition of the competing radioligand ([$^3$H]MPEP). L is the concentration of radioligand used in the binding experiment and the $K_d$ value of the radioligand is empirically determined for each batch of membranes prepared.

The compounds of the present invention are mGluR 5a receptor antagonists. The activities of compounds of formula I as measured in the assay described above are in the range of $K_i$<4 µM and preferably <150 nM.

| Ex. | Ki | Ex. | Ki [nM] | Ex. | Ki [nM] |
|---|---|---|---|---|---|
| 1  | 3    | 23 | 4   | 109 | 127 |
| 2  | 7    | 26 | 287 | 118 | 714 |
| 3  | 11   | 27 | 55  | 131 | 196 |
| 4  | 244  | 28 | 411 | 141 | 24  |
| 5  | 29   | 29 | 250 | 142 | 182 |
| 6  | 34   | 30 | 280 | 153 | 59  |
| 7  | 14   | 31 | 620 | 161 | 38  |
| 8  | 396  | 32 | 501 | 163 | 20  |
| 9  | 1203 | 33 | 14  | 167 | 79  |
| 10 | 23   | 34 | 36  | 169 | 30  |
| 11 | 10   | 35 | 51  | 170 | 576 |
| 12 | 253  | 36 | 113 | 173 | 33  |
| 13 | 25   | 37 | 90  | 174 | 39  |
| 14 | 4    | 50 | 213 | 177 | 111 |
| 15 | 17   | 56 | 29  | 180 | 364 |
| 16 | 17   | 64 | 8   | 185 | 290 |
| 17 | 2    | 67 | 37  | 192 | 110 |
| 18 | 124  | 86 | 929 | 194 | 221 |
| 19 | 25   | 87 | 20  | 198 | 181 |
| 20 | 6    | 95 | 411 | 199 | 14  |
|    |      |    |     | 200 | 81  |

The present invention also provides pharmaceutical compositions containing compounds of the invention, for example compounds of formula I and their pharmaceutically suitable acid addition salts, and a pharmaceutically acceptable carrier. Such pharmaceutical compositions can be in the form of tablets, coated tablets, dragées, hard and soft gelatine capsules, solutions, emulsions or suspensions. The pharmaceutical compositions also can be in the form of suppositories or injectable solutions.

The pharmaceutical compounds of the invention, in addition to one or more compounds of the invention, contain a pharmaceutically acceptable carrier. Suitable pharmaceutically acceptable carriers include pharmaceutically inert, inorganic and organic carriers. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula (I), but as a rule are not necessary. Suitable carriers for suppositories are, for example, natural or hardened oils, waxes, fats, semi-liquid or liquid polyols and the like.

In addition, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The invention also provides a method for preparing compositions of the invention which comprises bringing one or more compounds of formula I and/or pharmaceutically acceptable acid addition salts thereof and, if desired, one or more other therapeutically valuable substances into a galenical administration form together with one or more therapeutically inert carriers.

The dosage at which compounds of the invention can be administered can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

The following examples are provided to further elucidate the invention and are not intended to limit the invention to the sole compounds exemplified:

Example 1

4-(3-Fluoro-phenyl)-6-methyl-pyridine-2-carboxylic acid (4-methyl-thiazol-2-yl)-amide Step 1: 6-Methyl-4-nitro-pyridine-2-carbonitrile To 10.2 ml (13.5 g, 104 mmol, 1.1 equiv.) of dimethylsulfate were added 15.0 g (94.4 mmol) of 2-Methyl-4-nitropyridine-N-oxide at 60° C. The reaction mixture was then stirred for 90 min at 70° C., and allowed to cool to room temperature. The solidified residue was triturated with 30 ml of ether. The product was filtered, washed with 20 ml of ether, and dried. The product was then dissolved in 100 ml of water and added dropwise over a period of 30 min. to a at −8° C. cooled solution of 24.6 g (377 mmol, 4.0 equiv.) of potassium cyanide in 100 ml of water. The reaction mixture was stirred for a further 15 min. at −8° C. The product was filtered off, washed twice with 15 ml of water and dried in vaccuo to yield the title compound (11.1 g, 72%) as a light brown solid.

Step 2: 6-Methyl-4-nitro-pyridine-2-carboxlic acid

A solution of 10.9 g (66.8 mmol) of 6-Methyl-4-nitro-pyridine-2-carbonitrile in 60 ml of 90% sulfuric acid was heated at 120° C. for 2 h and then allowed to cool to room temperature. A solution of 12.2 g (69.0 mmol, 2.65 equiv.) of sodium nitrite in 22 ml of water was added dropwise over a period of 30 min maintaining the temperature between 12-15° C. The reaction was stirred for 30 min at room temperature and then for 1 h at 80° C. The solution was allowed to cool to room temperature and poured onto 150 g of crushed ice. After stirring the yellow solution for 10 min, 200 ml of water were added whereby precipitation occurs. The product is filtered, washed with a small amount of water and dried in vaccuo to yield the title compound as a light yellow crystalline solid (11.2 g, 92%), MS (ISP): m/e=183.1 (M+H)$^+$.

Step 3: 4-Bromo-6-methyl-pyridine-2-carboxylic acid

A solution of 3.6 g (19.6 mmol) of 6-Methyl-4-nitro-pyridine-2-carboxylic acid in 40 ml of 48% hydrobromic acid was heated at 100° C. overnight and then allowed to cool to room temperature. The solution was then evaporated to dryness in vaccuo. The crude material (10.5 g) containing inorganic salts was directly used in the next step.

Step 4: 4-Bromo-6-methyl-pyridine-2-carboxylic acid ethyl ester

The crude material (10.5) from the preceding step was suspended in 120 ml of Ethanol. Concentrated (95%) sulfuric acid (0.1 lml) was added to the yellow suspension which was refluxed for 8 h. The solution was concentrated in vaccuo. The residue was dissolved in 25 ml of water and the pH of the solution was adjusted to 7 by addition of sat. sodium carbonate solution. The aqueous phase was extracted with ethyl acetate (3×50 ml). The combined organic phases were washed with 30 ml of water, dried and concentrated in vaccuo to yield 2.8 g of a red oil which was purified by flash chromatography (heptane/ethyl acetate 1:1) to yield the title compound (2.1 g, 45%, steps 3+4) as a light yellow oil, MS (ISP): m/e=244.2, 246.2 (M+H)$^+$.

Step 5: 4-Bromo-6-methyl-pyridine-2-carboxylic acid (4-methyl-thiazol-2-yl)-amide To a solution of 3.72 g (32.6 mmol) of 2-Amino-4-methylthiazole in 40 ml of dry dioxane were added dropwise 15.9 ml (31.8 mmol, 4.0 equiv.) of a 2M solution of trimethylaluminium in hexane. The solution was stirred for 30 min at room temperature. Then a solution of 1.94 g (7.95 mmol) of 4-Bromo-6-methyl-pyridine-2-carboxylic acid ethyl ester in 6 ml of dry dioxane was added dropwise and the reaction was heated to 100° C. for 1.5 h. The reaction was quenched by cautious addition of 2.5 ml of water. Then approximately 10 g of anhydrous sodium sulfate were added to bind the water and the mixture was stirred vigorously for 5 min. The mixture was diluted by addition of 20 ml of methylene chloride and filtered over Speedex filteraid which was washed with methylene chloride. The filtrate was concentrated in vaccuo and the residue was purified by flash chromatography (heptane/ethyl acetate 4:1) to yield the title compound (1.95 g, 79%) as a yellow solid, MS (ISP): m/e=312.0, 314.0 (M+H)$^+$.

Step 6: 4-(3-Fluoro-phenyl)-6-methyl-pyridine-2-carboxylic acid (4-methyl-thiazol-2-yl)-amide To a suspension of 150 mg (0.48 mmol) of 4-Bromo-6-methyl-pyridine-2-carboxylic acid (4-methyl-thiazol-2-yl)-amide, 71 mg (0.5 mmol, 1.05 equiv.) of 3-Fluorophenyl-boronic acid in 2 ml of dioxane were added 0.5 ml of 2M sodium carbonate solution and the mixture was purged with Argon for 10 min. Then 25 mg (0.096 mmol, 0.2 equiv.) of Triphenylphosphine and 10.8 mg (0.048 mmol, 0.1 equiv.) of Palladium acetate were added and the mixture was stirred under Argon atmosphere for 24 h at 90° C. The reaction was allowed to cool to r.t., taken up in two times in ethyl acetate and evaporated to dryness. The residue was separated by flash chromatography on silicagel (heptane/ethyl acetate 4:1) to yield the title compound (111 mg, 71%) as a yellow solid, MS (ISP): m/e=328.0 (M+H)$^+$.

Example 2

4-(3,5-Difluoro-phenyl)-6-methyl-pyridine-2-carboxylic acid (4-methyl-thiazol-2-yl)-amide The title compound, light yellow solid, MS (ISP): m/e=346.1 (M+H)$^+$, was prepared from 4-Bromo-6-methyl-pyridine-2-carboxylic acid (4-methyl-thiazol-2-yl)-amide in accordance with the general method of example 1. Step 6 was performed using 3,5-Difluorophenyl-boronic acid instead of 3-Fluorophenyl-boronic acid.

Example 3

4-(3-Cyano-phenyl)-6-methyl-pyridine-2-carboxylic acid (4-methyl-thiazol-2-yl)-amide The title compound, white cristalline solid, MS (ISP): m/e=335.3 (M+H)$^+$, was prepared from 4-Bromo-6-methyl-pyridine-2-carboxylic acid (4-methyl-thiazol-2-yl)-amide in accordance with the general method of example 1. Step 6 was performed using 3-Cyanophenyl-boronic acid instead of 3-Fluorophenyl-boronic acid.

Example 4

6-Chloro-6'-methyl-[3,4']bipyridinyl-2'-carboxylic add (4-methyl-thiazol-2-yl)-amide The title compound, light brown solid, MS (ISP): m/e=345.0, 347.0 (M+H)$^+$, was prepared from 4-Bromo-6-methyl-pyridine-2-carboxylic acid (4-methyl-thiazol-2-yl)-amide in accordance with the general method of example 1. Step 6 was performed using 2-Chloropyridine-5-boronic acid instead of 3-Fluorophenyl-boronic acid.

Example 5

4-(2,5-Difluoro-phenyl)-6-methyl-pyridine-2-carboxylic acid (4-methyl-thiazol-2-yl)-amide The title compound, light yellow criastalline solid, MS (ISP): m/e=346.1 (M+H)$^+$, was prepared from 4-Bromo-6-methyl-pyridine-2-carboxylic acid (4-methyl-thiazol-2-yl)-amide in accordance with the general method of example 1. Step 6 was performed using 2,5-Difluorophenyl-boronic acid instead of 3-Fluorophenyl-boronic acid.

Example 6

4-(3-Methoxy-phenyl)-6-methyl-pyridine-2-carboxylic acid (4-methyl-thiazol-2-yl)-amide The title compound, white solid, MS (ISP): m/e=340.1 (M+H)$^+$, was prepared from 4-Bromo-6-methyl-pyridine-2-carboxylic acid (4-methyl-thiazol-2-yl)-amide in accordance with the general method of example 1. Step 6 was performed using 2-Methoxyphenyl-boronic acid instead of 3-Fluorophenyl-boronic acid.

Example 7

6-Methyl-4-(3-trifluoromethoxy-phenyl)-pyridine-2-carboxylic acid (4-methyl-thiazol-2-yl)-amide The title compound, white solid, MS (ISP): m/e=394.1 (M+H)$^+$, was prepared from 4-Bromo-6-methyl-pyridine-2-carboxylic acid (4-methyl-thiazol-2-yl)-amide in accordance with the general method of example 1. Step 6 was performed using 3-(Trifluoromethoxy)phenyl-boronic acid instead of 3-Fluorophenyl-boronic acid.

Example 8

4-(3-Methanesulfonyl-phenyl)-6-methyl-pyridine-2-carboxylic acid (4-methyl-thiazol-2-yl)-amide The title compound, white solid, MS (ISP): m/e=388.2 (M+H)$^+$, was prepared from 4-Bromo-6-methyl-pyridine-2- carboxylic acid (4-methyl-thiazol-2-yl)-amide in accordance with the general method of example 1. Step 6 was performed using 3-Methylsulfonylphenylboronic acid instead of 3-Fluorophenyl-boronic acid.

Example 9

4-(4-Methoxy-phenyl)-6-methyl-pyridine-2-carboxylic acid (4-methyl-thiazol-2-yl)-amide The title compound, white solid, MS (ISP): m/e=340.1 $(M+H)^+$, was prepared from 4-Bromo-6-methyl-pyridine-2-carboxylic acid (4-methyl-thiazol-2-yl)-amide in accordance with the general method of example 1. Step 6 was performed using 4-Methoxyphenyl-boronic acid instead of 3-Fluorophenyl-boronic acid.

Example 10

4-(3,4-Difluoro-phenyl)-6-methyl-pyridine-2-carboxylic acid (4-methyl-thiazol-2-yl)-amide The title compound, white solid, MS (ISP): m/e=346.1 $(M+H)^+$, was prepared from 4-Bromo-6-methyl-pyridine-2-carboxylic acid (4-methyl-thiazol-2-yl)-amide in accordance with the general method of example 1. Step 6 was performed using 3,4-Difluorophenyl-boronic acid instead of 3-Fluorophenyl-boronic acid.

Example 11

6-Methyl-4-(3,4,5-trifluoro-phenyl)-pyridine-2-carboxylic acid (4-methyl-thiazol-2-yl)-amide The title compound, white solid, MS (ISP): m/e=364.0 $(M+H)^+$, was prepared from 4-Bromo-6-methyl-pyridine-2-carboxylic acid (4-methyl-thiazol-2-yl)-amide in accordance with the general method of example 1. Step 6 was performed using 3,4,5-Trifluorophenyl-boronic acid instead of 3-Fluorophenyl-boronic acid.

Example 12

4-(4-Cyano-phenyl)-6-methyl-pyridine-2-carboxylic acid (4-methyl-thiazol-2-yl)-amide The title compound, white solid, MS (ISP): m/e=335.3 $(M+H)^+$, was prepared from 4-Bromo-6-methyl-pyridine-2-carboxylic acid (4-methyl-thiazol-2-yl)-amide in accordance with the general method of example 1. Step 6 was performed using 4-Cyanophenyl-boronic acid instead of 3-Fluorophenyl-boronic acid.

Example 13

4-(2-Methoxy-phenyl)-6-methyl-pyridine-2-carboxylic acid (4-methyl-thiazol-2-yl)-amide The title compound, white solid, MS (ISP): m/e=340.1 $(M+H)^+$, was prepared from 4-Bromo-6-methyl-pyridine-2-carboxylic acid (4-methyl-thiazol-2-yl)-amide in accordance with the general method of example 1. Step 6 was performed using 2-Methoxyphenyl-boronic acid instead of 3-Fluorophenyl-boronic acid.

Example 14

4-(2-Chloro-phenyl)-6-methyl-pyridine-2-carboxylic acid (4-methyl-thiazol-2-yl)-amide The title compound, white solid, MS (ISP): m/e=344.0, 346.0 $(M+H)^+$, was prepared from 4-Bromo-6-methyl-pyridine-2-carboxylic acid (4-methyl-thiazol-2-yl)-amide in accordance with the general method of example 1. Step 6 was performed using 2-Chlorophenyl-boronic acid instead of 3-Fluorophenyl-boronic acid.

Example 15

4-(3-Hydroxymethyl-phenyl)-6-methyl-pyridine-2-carboxylic acid (4-methyl-thiazol-2-yl)-amide The title compound, white solid, MS (ISP): m/e=340.1 $(M+H)^+$, was prepared from 4-Bromo-6-methyl-pyridine-2-carboxylic acid (4-methyl-thiazol-2-yl)-amide in accordance with the general method of example 1. Step 6 was performed using 3-(Hydroxymethyl)phenyl boronic acid instead of 3-Fluorophenyl-boronic acid.

Example 16

6'-Methyl-[3,4']bipyridinyl-2'-carboxylic acid (4-methyl-thiazol-2-yl)-amide

The title compound, white solid, MS (ISP): m/e=311.2 $(M+H)^+$, was prepared from 4-Bromo-6-methyl-pyridine-2-carboxylic acid (4-methyl-thiazol-2-yl)-amide in accordance with the general method of example 1. Step 6 was performed using 3-Pyridine-boronic acid instead of 3-Fluorophenyl-boronic acid.

Example 17

4-(3,5-Dichloro-phenyl)-6-methyl-pyridine-2-carboxylic acid (4-methyl-thiazol-2-yl)-amide The title compound, white solid, MS (ISP): m/e=378.1 $(M+H)^+$, was prepared from 4-Bromo-6-methyl-pyridine-2-carboxylic acid (4-methyl-thiazol-2-yl)-amide in accordance with the general method of example 1. Step 6 was performed using 3,5-Dichlorophenyl-boronic acid instead of 3-Fluorophenyl-boronic acid.

Example 18

6-Methyl-4-pyrimidin-5-yl-pyridine-2-carboxylic acid (4-methyl-thiazol-2-yl)-amide The title compound, yellow solid, MS (ISP): m/e=312.2 $(M+H)^+$, was prepared from 4-Bromo-6-methyl-pyridine-2-carboxylic acid (4-methyl-thiazol-2-yl)-amide in accordance with the general method of example 1. Step 6 was performed using Pyrimidine-5-boronic acid instead of 3-Fluorophenyl-boronic acid.

Example 19

5-Fluoro-6'-methyl-[3,4']bipyridinyl-2'-carboxylic acid (4-methyl-thiazol-2-yl)-amide The title compound, off-white solid, MS (ISP): m/e=329.2 (M+H)$^+$, was prepared from 4-Bromo-6-methyl-pyridine-2-carboxylic acid (4-methyl-thiazol-2-yl)-amide in accordance with the general method of example 1. Step 6 was performed using 3-Fluoro-5-(4,4,5,5-tetramethyl-[1,3,2]dioxaborolan-2-yl)pyridine instead of 3-Fluorophenyl-boronic acid.

Example 20

4-(3,5-Dichloro-phenyl)-6-methyl-pyridine-2-carboxylic acid (2-methyl-thiazol-4-yl)-amide Step 1: 4-Bromo-6-methyl-pyridine-2-carboxylic acid (2-methyl-thiazol-4-yl)-amide The title compound, white cristalline solid, MS (ISP): m/e=312.1, 314.1 (M+H)$^+$, was prepared from 4-Bromo-6-methyl-pyridine-2-carboxylic acid ethyl ester in accordance with the general method of example 1. Step 5 was performed using 4-Amino-2-methylthiazole instead of 2-Amino-4-methylthiazole.

Step 2: 4-(3,5-Dichloro-phenyl)-6-methyl-pyridine-2-carboxylic acid (2-methyl-thiazol-4-yl)-amide The title compound, white cristalline solid, MS (ISP): m/e=378.2 (M+H)$^+$, was prepared from 4-Bromo-6-methyl-pyridine-2-carboxylic acid (2-methyl-thiazol-4-yl)-amide in accordance with the general method of example 1. Step 6 was performed using 3,5-Dichlorophenyl-boronic acid instead of 3-Fluorophenyl-boronic acid.

Example 21

4-(3-Chloro-4-fluoro-phenyl)-6-methyl-pyridine-2-carboxylic acid (2-methyl-thiazol-4-yl)-amide The title compound, white cristalline solid, MS (ISP): m/e=362.2 (M+H)$^+$, was prepared from 4-Bromo-6-methyl-pyridine-2-carboxylic acid (2-methyl-thiazol-4-yl)-amide in accordance with the general method of example 1. Step 6 was performed using 3-Chloro-4-fluorophenyl-boronic acid instead of 3-Fluorophenyl-boronic acid.

Example 22

4-(3,4-Difluoro-phenyl)-6-methyl-pyridine-2-carboxylic acid (2-methyl-thiazol-4-yl)-amide The title compound, white cristalline solid, MS (ISP): m/e=346.1 (M+H)$^+$, was prepared from 4-Bromo-6-methyl-pyridine-2-carboxylic acid (2-methyl-thiazol-4-yl)-amide in accordance with the general method of example 1. Step 6 was performed using 3,4-Difluorophenyl-boronic acid instead of 3-Fluorophenyl-boronic acid.

Example 23

4-(3,5-Dichloro-phenyl)-6-methyl-pyridine-2-carboxylic acid (1-methyl-1H-pyrazol-3-yl)-amide Step 1: 4-Bromo-6-methyl-pyridine-2-carboxylic acid (1-methyl-1H-pyrazol-3-yl)-amide The title compound, white cristalline solid, MS (ISP): m/e=295.1, 297.1 (M+H)$^+$, was prepared from 4-Bromo-6-methyl-pyridine-2-carboxylic acid ethyl ester in accordance with the general method of example 1. Step 5 was performed using 3-Amino-1-methyl-1H-pyrazole instead of 2-Amino-4-methylthiazole.

Step 2: 4-(3,5-Dichloro-phenyl)-6-methyl-pyridine-2-carboxylic acid (2-methyl-thiazol-4-yl)-amide The title compound, white cristalline solid, MS (ISP): m/e=361.1 (M+H)$^+$, was prepared from 4-Bromo-6-methyl-pyridine-2-carboxylic acid (1-methyl-1H-pyrazol-3-yl)-amide in accordance with the general method of example 1. Step 6 was performed using 3,5-Dichlorophenyl-boronic acid instead of 3-Fluorophenyl-boronic acid.

Example 24

4-(3-Chloro-4-fluoro-phenyl)-6-methyl-pyridine-2-carboxylic acid (1-methyl-1H-pyrazol-3-yl)-amide The title compound, white cristalline solid, MS (ISP): m/e=345.2, 347.2 (M+H)$^+$, was prepared from 4-Bromo-6-methyl-pyridine-2-carboxylic acid (1-methyl-1H-pyrazol-3-yl)-amide in accordance with the general method of example 1. Step 6 was performed using 3-Chloro-4-fluorophenyl-boronic acid instead of 3-Fluorophenyl-boronic acid.

Example 25

4-(3,4-Difluoro-phenyl)-6-methyl-pyridine-2-carboxylic acid (1-methyl-1H-pyrazol-3-yl)-amide The title compound, white cristalline solid, MS (ISP): m/e=329.3 (M+H)$^+$, was prepared from 4-Bromo-6-methyl-pyridine-2-carboxylic acid (1-methyl-1H-pyrazol-3-yl)-amide in accordance with the general method of example 1. Step 6 was performed using 3,4-Difluorophenyl-boronic acid instead of 3-Fluorophenyl-boronic acid.

Example 26

4-(4-Fluoro-phenyl)-6-methyl-pyridine-2-carboxylic acid (3-chloro-phenyl)-amide

Step 1: 4-(4-Fluoro-phenyl)-2-methyl-pyridine

Argon was bubbled for 15 min through a suspension of 1.11 ml (1.276 g, 10.0 mmol) 4-Chloropicoline, 2.798 g (20.0 mmol, 2.0 equiv.) of 4-Fluorophenylboronic acid, and 1.917 g (33.0 mmol, 3.3 equiv.) of KF in 20 ml of Dioxane. Then 155 mg (0.15 mmol, 1.5 mol %)Pd2(dba)3×CHCl3 and 104 ul (93 mg, 0.45 mmol, 4.5 mol %) Tri-tert-butylphosphine were added. The mixture was then stirred for 1 h under argon at 100° C. The reaction was worked up in the usual manner with diethylether, water, and sodium carbonate solution. The combined organic phases were washed with 30 ml of water, dried and concentrated in vaccuo to yield 2.5 g of a light yellow oil which was purified by flash chromatography (heptane/ethyl acetate 1:1) to yield the title compound (1.81 g, 97%) as a white solid, MS (ISP): m/e=188.3 (M+H)$^+$.

Step 2: 4-(4-Fluoro-phenyl)-2-methyl-pyridine 1-oxide

To a solution of 1.50 g (8.0 mmol) of 4-(4-Fluoro-phenyl)-2-methyl-pyridine in 25 ml of methylene chloride were added 5.93 g (24 mmol, 3.0 equiv.) of 70% m-Chloroperbenzoic acid. The reaction was stirred for 6 h at room temperature. The reaction was worked up with 50 ml 5% sodium bicarbonate solution. The aqueous phase was extracted twice with 40 ml of methylene chloride. The combined organic phases were washed with 30 ml of brine, dried over magnesium sulfate, and concentrated in vaccuo to yield 3.3 g of a yellow oil which was purified by flash chromatography (ethyl acetate/methanol 9:1) to yield the title compound (1.31 g, 80%) as a crystalline light brown solid, MS (ISP): m/e=204.1 (M+H)$^+$.

Step 3: 4-(4-Fluoro-phenyl)-6-methyl-pyridine-2-carbonitrile

To a solution of 1.30 g (6.4 mmol) of 4-(4-Fluoro-phenyl)-2-methyl-pyridine 1-oxide in 20 ml of methylene chloride was added dropwise 1.00 ml (8.0 mmol, 1.25 equiv.) of Trimethylsilyl cyanide. Then 0.73 ml (0.86 g, 8.0 mmol, 1.25 equiv.) of Dimethylcarbamoyl chloride was added dropwise over a period of 5 min. After stirring overnight at room temperature, 8 ml of saturated sodium carbonate solution were added. The aqueous phase was extracted twice with 15 ml of methylene chloride. The combined organic phases were washed with 20 ml of brine, dried over magnesium sulfate, and concentrated in vaccuo to yield 2.2 g of a beige solid which was purified by flash chromatography (ethyl acetate/hexane 1:4) to yield the title compound (0.75 g, 55%) as a crystalline white solid, MS (ISP): m/e=213.1 (M+H)$^+$.

Step 4: 4-(4-Fluoro-phenyl)-6-methyl-pyridine-2-carboxylic acid ethyl ester

A suspension of 0.55 g (2.6 mmol) 4-(4-Fluoro-phenyl)-6-methyl-pyridine-2-carbonitrile in 11 ml of 25% potassium hydroxide solution was heated to 100° C. for 14 h. Water (5 ml) was added and the pH adjusted to 6 by addition of acetic acid, then 10 ml of ethanol was added and the mixture was evaporated to dryness. The crude material was suspended in 30 ml of ethanol. Concentrated sulfuric acid (2 ml) were added and the suspension was refluxed for 35 h. The solution was concentrated, taken up in 20 ml of water, neutralized (pH=7-8) by addition of 5% sodium bicarbonate solution, and extracted twice with 50 ml of ethyl acetate. The combined organic phases were washed with 20 ml of water, 20 ml of brine, dried over magnesium sulfate, and concentrated in vaccuo to yield 0.42 g (1.63 mmol, 63%) of a light yellow oil which is sufficiently pure for further use in the next step, MS (ISP): m/e=260.1 (M+H)$^+$.

Step 6: 4-(4-Fluoro-phenyl)-6-methyl-pyridine-2-carboxylic acid (3-chloro-phenyl)-amide To a solution of 113 µl (138 mg, 1.08 mmol, 4.0 equiv.) of 3-Chloroaniline in 7 ml of dry dioxane were added 540 µl (1.08 mmol, 4.0 equiv.) of a 2M solution of trimethylaluminium in hexane. The solution was stirred for 45 min at room temperature. Then a solution of 70.0 mg (0.27 mmol) of 4-(4-Fluoro-phenyl)-6-methyl-pyridine-2-carboxylic acid ethyl ester in 1 ml of dry dioxane was added and the reaction was heated to 100° C. for 1 h. The reaction was quenched by cautious addition of 0.7 ml of water. Then approximately 1 g of anhydrous sodium sulfate were added to bind the water and the mixture was stirred vigorously for 5 min. The mixture was diluted by addition of 10 ml of methylenene chloride and filtered over Speedex filter aid which was washed with methylene chloride. The filtrate was concentrated in vaccuo and the residue (248 mg orange solid) was purified by flash chromatography (heptane/ethyl acetate 4:1) to yield the title compound (68.0 mg, 74%) as a crystalline white solid, MS (ISP): m/e=341.0, 343.0 (M+H)$^+$.

Example 27

4-(4-Fluoro-phenyl)-6-methyl-pyridine-2-carboxylic acid (4-methyl-thiazol-2-yl)-amide The title compound, white cristalline solid, MS (ISP): m/e=327.9 (M+H)$^+$, was prepared from 4-(4-Fluoro-phenyl)-6-methyl-pyridine-2-carboxylic acid ethyl ester in accordance with the general method of example 26. Step 6 was performed using 2-Amino-4-methylthiazole instead of 3-Chloroaniline.

Example 28

4-(4-Fluoro-phenyl)-6-methyl-pyridine-2-carboxylic acid (2-methyl-pyridin-4-yl)-amide The title compound, white cristalline solid, MS (ISP): m/e=322.3 (M+H)$^+$, was prepared from 4-(4-Fluoro-phenyl)-6-methyl-pyridine-2-carboxylic acid ethyl ester in accordance with the general method of example 26. Step 6 was performed using 4-Amino-2-methylpyridine instead of 3-Chloroaniline.

Example 29

4-(4-Fluoro-phenyl)-6-methyl-pyridine-2-carboxylic acid (1-methyl-1H-pyrazol-3-yl)-amide The title compound, white cristalline solid, MS (ISP): m/e=311.4 (M+H)$^+$, was prepared from 4-(4-Fluoro-phenyl)-6-methyl-pyridine-2-carboxylic acid ethyl ester in accordance with the general method of example 26. Step 6 was performed using 3-Amino-1-methyl-1H-pyrazole instead of 3-Chloroaniline.

Example 30

4-(4-Fluoro-phenyl)-6-methyl-pyridine-2-carboxylic acid (5-fluoro-pyridin-2-yl)-amide The title compound, white cristalline solid, MS (ISP): m/e=326.1 (M+H)$^+$, was prepared from 4-(4-Fluoro-phenyl)-6-methyl-pyridine-2-carboxylic acid ethyl ester in accordance with the general method of example 26. Step 6 was performed using 2-Amino-5-fluoropyridine instead of 3-Chloroaniline.

Example 31

4-(4-Fluoro-phenyl)-6-methyl-pyridine-2-carboxylic acid (2-chloro-pyridin-4-yl)-amide The title compound, white cristalline solid, MS (ISP): m/e=342.0, 344.0 (M+H)⁺; was prepared from 4-(4-Fluoro-phenyl)-6-methyl-pyridine-2-carboxylic acid ethyl ester in accordance with the general method of example 26. Step 6 was performed using 4-Amino-2-chloropyridine instead of 3-Chloroaniline.

Example 32

4-(4-Fluoro-phenyl)-6-methyl-pyridine-2-carboxylic acid (2-methyl-pyrimidin-4-yl)-amide The title compound, white cristalline solid, MS (ISP): m/e=323.3 (M+H)⁺, was prepared from 4-(4-Fluoro-phenyl)-6-methyl-pyridine-2-carboxylic acid ethyl ester in accordance with the general method of example 26. Step 6 was performed using 4-Amino-2-methyl-pyrimidine instead of 3-Chloroaniline.

Example 33

6-(3,5-Difluoro-phenyl)-2-methyl-pyrimidine-4-carboxylic acid (4-methyl-thiazol-2-yl)-amide Step 1: 4-(3,5-Difluoro-phenyl)-2,6-dimethyl-pyrimidine To a suspension of 8.0 g, (43 mmol) of 4-Bromo-2,6-dimethyl-pyrimidine [CAS 354574-56-4], 8.1 g (51 mmol, 1.2 equiv.) of 3,5-Difluorophenylboronic acid, an 1.917 g (33.0 mmol, 3.3 equiv.) of KF in 80 ml of DME were added 20 ml of 2M sodium carbonate solution and the mixture was purged with Argon for 10 min. Then 2.24 g (8.6 mmol, 0.2 equiv.) of Triphenylphosphine and 0.96 g (4.3 mmol, 0.1 equiv.) of Palladium acetate were added and the mixture was stirred under Argon atmosphere for 18 h at 85° C. The reaction was allowed to cool to r.t., and worked up with ethyl acetate/water. The crude material was purified by flash chromatography on silicagel (heptane/ethyl acetate 1:1) to yield the title compound (1.96 g, 21%) as a red solid, MS (ISP): m/e=221.2 (M+H)⁺.

Step 2: 6-(3,5-Difluoro-phenyl)-2-methyl-pyrimidine-4-carboxylic acid methyl ester To a solution of 1.95 g, (9 mmol) of 4-(3,5-Difluoro-phenyl)-2,6-dimethyl-pyrimidine in 10 ml of Pyridine were added 1.08 g (10 mmol, 1.1 equiv.) of Selenium dioxide and the mixture was refluxed for 4 h. The black mixture was filtered to remove precipitated selenium, treated with 4 ml of 3N sodium hydroxide solution and evaporated to dryness. The residue was taken up in 15 ml of methanol. Thionyl chloride (1.5 ml) was added and the mixture was stirred for 2 days at room temperature, and worked up with methylene chloride and sodium bicarbonate solution; dried over magnesium sulfate, and concentrated in vaccuo. The crude material was purified by flash chromatography on silicagel (heptane/ethyl acetate 2:1) to yield the title compound (1.12 g, 48%) as a dark brown solid, MS (ISP): m/e=265.1 (M+H)⁺.

Step 3: 6-(3,5-Difluoro-phenyl)-2-methyl-pyrimidine-4-carboxylic acid (4-methyl-thiazol-2-yl)-amide To a solution of 156 mg (1.37 mmol, 1.8 equiv.) of 2-Amino-4-methylthiazole in 4 ml of dry dioxane were added 0.68 μl (1.37 mmol, 1.8 equiv.) of a 2M solution of trimethylaluminium in hexane. The solution was stirred for 1 h at room temperature. Then 200.0 mg (0.76 mmol) of 6-(3,5-Difluoro-phenyl)-2-methyl-pyrimidine-4-carboxylic acid methyl ester were added and the reaction was heated to 90° C. for 4 h. The reaction was quenched by cautious addition of 0.2 ml of water. Then approximately 1 g of anhydrous sodium sulfate were added to bind the water and the mixture was stirred vigorously for 5 min. The mixture was diluted by addition of 10 ml of methylenene chloride and filtered over Speedex filter aid which was washed with methylene chloride. The filtrate was concentrated in vaccuo and the residue was purified by flash chromatography (heptane/ethyl acetate 4:1) and recristallised from diisopropyl ether to yield the title compound (152.0 mg, 58%) as a white solid, MS (ISP): m/e=347.1 (M+H)⁺.

Example 34

6-(3,5-Difluoro-phenyl)-2-methyl-pyrimidine-4-carboxylic acid (2-methyl-thiazol-4-yl)-amide The title compound, light yellow solid, MS (ISP): m/e=347.1 (M+H)⁺, was prepared from 6-(3,5-Difluoro-phenyl)-2-methyl-pyrimidine-4-carboxylic acid methyl ester in accordance with the general method of example 33. Step 3 was performed using 4-Amino-2-methyl-thiazole instead of 2-Amino-4-methylthiazole.

Example 35

6-(3,5-Difluoro-phenyl)-2-methyl-pyrimidine-4-carboxylic acid (1-methyl-1H-pyrazol-3-yl)-amide The title compound, white solid, MS (ISP): m/e=330.2 (M+H)⁺, was prepared from 6-(3,5-Difluoro-phenyl)-2-methyl-pyrimidine-4-carboxylic acid methyl ester in accordance with the general method of example 33. Step 3 was performed using 3-Amino-1-methyl-1H-pyrazole instead of 2-Amino-4-methylthiazole.

Example 36

6-(3,5-Difluoro-phenyl)-2-methyl-pyrimidine-4-carboxylic acid (2-chloro-pyridin-4-yl)-amide The title compound, yellow solid, MS (ISP): m/e=361.1, 363.1 (M+H)⁺, was prepared from 6-(3,5-Difluoro-phenyl)-2-methyl-pyrimidine-4-carboxylic acid methyl ester in accordance with the general method of example 33. Step 3 was performed using 4-Amino-2-chloropyridine instead of 2-Amino-4-methylthiazole.

Example 37

6-(3,5-Difluoro-phenyl)-2-methyl-pyrimidine-4-carboxylic acid (2-methyl-pyridin-4-yl)-amide The title compound, yellow solid, MS (ISP): m/e=341.1 (M+H)⁺, was prepared from 6-(3,5-Difluoro-phenyl)-2-methyl-pyrimidine-4-carboxylic acid methyl ester in accordance with the general method of example 33. Step 3 was performed using 4-Amino-2-methylpyridine instead of 2-Amino-4-methylthiazole.

Example 38

2-Methyl-6-pyridin-3-yl-pyrimidine-4-carboxylic acid (4-methyl-thiazol-2-yl)-amide

Step 1: 2,4-Dimethyl-6-pyridin-3-yl-pyridine

The title compound, was prepared from 4-Bromo-2,6-dimethyl-pyrimidine and 3-Pyridineboronic acid in accordance with the general method of example 33, step 1 to yield the final compound as a brown oil, MS (ISP): m/e=186.3 (M+H)$^+$.

Step 2: 6-Methyl-4-pyrimidin-5-yl-pyridine-2-carboxylic acid methyl ester

The title compound, was prepared from 2,4-Dimethyl-6-pyridin-3-yl-pyrimidine by oxidation to the carboxylic acid followed by esterification in accordance with the general method of example 33, step 2 to yield the final compound as a white solid, MS (ISP): m/e=230.3 (M+H)$^+$.

Step 3: 2-Methyl-6-pyridin-3-yl-pyrimidine-4-carboxylic acid (4-methyl-thiazol-2-yl)-amide The title compound, was prepared from 6-Methyl-4-pyrimidin-5-yl-pyridine-2-carboxylic acid methyl ester in accordance with the general method of example 33, step 3 using 2-Amino-4-methylthiazole instead of 3-chloroaniline to yield the final compound as a light yellow solid, MS (ISP): m/e=312.1 (M+H)$^+$.

Example 39

4-(2,5-Dimethyl-2H-pyrazol-3-yl)-6-methyl-pyridine-2-carboxylic acid (4-methyl-thiazolyl)-amide The title compound, was prepared from 4-Bromo-6-methyl-pyridine-2-carboxylic acid (4-methyl-thiazol-2-yl)-amide in accordance with the general method of example 1, step 6; using 1,4-Dimethyl-1H-pyrazole-2-boronic acid instead of 3-Fluorophenyl-boronic acid to yield the final compound as a white solid, MS (ISP): m/e=328.1 (M+H)$^+$.

Example 40

2'-Chloro-6-methyl-[4,4']bipyridinyl-2-carboxylic-acid (4-methyl-thiazol-2-yl)-amide The title compound, was prepared from 4-Bromo-6-methyl-pyridine-2-carboxylic acid (4-methyl-thiazol-2-yl)-amide in accordance with the general method of example 1, step 6; using 2-Chloro-4-boronic acid instead of 3-Fluorophenyl-boronic acid to yield the final compound as a light yellow solid, MS (ISP): m/e=345 (M+H)$^+$.

Example 41

6'-Methyl-[2,4']bipyridinyl-2'-carboxylic acid (4-methyl-thiazol-2-yl)-amide The title compound, was prepared from 4-Bromo-6-methyl-pyridine-2-carboxylic acid (4-methyl-thiazol-2-yl)-amide in accordance with the general method of example 1, step 6; using 2-Iodopyridine (one pot two step) instead of 3-Fluorophenyl-boronic acid to yield the final compound as a white solid, MS (ISP): m/e=311.2 (M+H)$^+$.

Example 42

6-Methyl-4-(3-trifluoromethyl-phenyl)-pyridine-2-carboxylic acid (4-methyl-thiazol-2-yl)-amide The title compound, was prepared from 4-Bromo-6-methyl-pyridine-2-carboxylic acid (4-methyl-thiazol-2-yl)-amide in accordance with the general method of example 1, step 6; using 3-(Trifluoromethyl)phenylboronic acid instead of 3-Fluorophenyl-boronic acid to yield the final compound as a white solid, MS (ISP): m/e=378.2 (M+H)$^+$.

Example 43

2-Chloro-6'-methyl-[3,4']bipyridinyl-2'-carboxylic acid (4-methyl-thiazol-2-yl)-amide The title compound, was prepared from 4-Bromo-6-methyl-pyridine-2-carboxylic acid (4-methyl-thiazol-2-yl)-amide in accordance with the general method of example 1, step 6; using 2-Chloro-3-pyridineboronic acid instead of 3-Fluorophenyl-boronic acid to yield the final compound as a light yellow solid, MS (ISP): m/e=345.0, 346.1 (M+H)$^+$.

Example 44

5-Cyano-6'-methyl-[3,4']bipyridinyl-2'-carboxylic acid (4-methyl-thiazol-2-yl)-amide The title compound, was prepared from 4-Bromo-6-methyl-pyridine-2-carboxylic acid (4-methyl-thiazol-2-yl)-amide in accordance with the general method of example 1, step 6; using 5-(4,4,5,5-Tetramethyl-[1,3,2]dioxaborolan-2-yl)-nicotinonitrile instead of 3-Fluorophenyl-boronic acid to yield the final compound as a off-white solid, MS (ISP): m/e=336.2 (M+H)$^+$.

Example 45

4-(3,5-Dimethyl-isoxazol-4-yl)-6-methyl-pyridine-2-carboxylic acid (4-methyl-thiazol-2-yl)-amide The title compound, was prepared from 4-Bromo-6-methyl-pyridine-2-carboxylic acid (4-methyl-thiazol-2-yl)-amide in accordance with the general method of example 1, step 6; using 3,5-Dimethyl-isoxazole-4-boronic acid instead of 3-Fluorophenyl-boronic acid to yield the final compound as a white solid, MS (ISP): m/e=329.4 (M+H)$^+$.

Example 46

4,6'-Dimethyl-[3,4']bipyridinyl-2'-carboxylic acid (4-methyl-thiazol-2-yl)-amide The title compound, was prepared from 4-Bromo-6-methyl-pyridine-2-carboxylic acid (4-methyl-thiazol-2-yl)-amide in accordance with the general method of example 1, step 6; using 6-Methyl-3-pyridineboronic acid instead of

Example 47

5-Methoxy-6'-methyl-[3,4']bipyridinyl-2'-carboxylic acid (4-methyl-thiazol-2-yl)-amide The title compound, was prepared from 4-Bromo-6-methyl-pyridine-2-carboxylic acid (4-methyl-thiazol-2-yl)-amide in accordance with the general method of example 1, step 6; using 5-Methoxy-3-pyridineboronic acid instead of 3-Fluorophenyl-boronic acid to yield the final compound as a white solid, MS (ISP): m/e=341.1 (M+H)$^+$.

Example 48

6-Fluoro-6'-methyl-[3,4']bipyridinyl-2'-carboxylic acid (4-methyl-thiazol-2-yl)-amide The title compound, was prepared from 4-Bromo-6-methyl-pyridine-2-carboxylic acid (4-methyl-thiazol-2-yl)-amide in accordance with the general method of example 1, step 6; using 4-Fluoro-3-pyridineboronic acid instead of 3-Fluorophenyl-boronic acid to yield the final compound as a white solid, MS (ISP): m/e=329.1 (M+H)$^+$.

Example 49

2'-Chloro-6-methyl-[4,4']bipyridinyl-2-carboxylic acid (4-methyl-thiazol-2-yl)-amide The title compound, was prepared from 4-Bromo-6-methyl-pyridine-2-carboxylic acid (4-methyl-thiazol-2-yl)-amide in accordance with the general method of example 1, step 6; using 2-Chloropyridine-4-boronic acid instead of 3-Fluorophenyl-boronic acid to yield the final compound as a white solid, MS (ISP): m/e=344.9 (M+H)$^+$.

Example 50

5-Methoxy-6'-methyl-[3,4']bipyridinyl-2'-carboxylic acid (1-methyl-1H-pyrazol-3-yl)-amide The title compound, was prepared from 4-Bromo-6-methyl-pyridine-2-carboxylic acid (1-methyl-1H-pyrazol-3-yl)-amide (example 23, step 1) in accordance with the general method of example 1, step 6; using 3-Methoxy-5-pyridineboronic acid instead of 3-Fluorophenyl-boronic acid to yield the final compound as a white crystalline solid, MS (ISP): m/e=324.3 (M+H)$^+$.

Example 51

6'-Methyl-[3,4']bipyridinyl-2'-carboxylic acid (1-methyl-1H-pyrazol-3-yl)-amide

The title compound, was prepared from 4-Bromo-6-methyl-pyridine-2-carboxylic acid (1-methyl-1H-pyrazol-3-yl)-amide in accordance with the general method of example 1, step 6; using 3-Pyridineboronic acid instead of 3-Fluorophenyl-boronic acid to yield the final compound as a white crystalline solid, MS (ISP): m/e=294.2 (M+H)$^+$.

Example 52

5-Fluoro-6'-methyl-[3,4']bipyridinyl-2'-carboxylic acid (1-methyl-1H-pyrazol-3-yl)-amide The title compound, was prepared from 4-Bromo-6-methyl-pyridine-2-carboxylic acid (1-methyl-1H-pyrazol-3-yl)-amide in accordance with the general method of example 1, step 6; using 3-Fluoro-5-(4,4,5,5-tetramethyl-[1,3,2]dioxaborolan-2-yl)pyridine instead of 3-Fluorophenyl-boronic acid to yield the final compound as a white crystalline solid, MS (ISP): m/e=312.2 (M+H)$^+$.

Example 53

4-(3,5-Difluorophenyl)-6-methyl-pyridine-2-carboxylic acid (1-methyl-1H-pyrazol-3-yl)-amide The title compound, was prepared from 4-Bromo-6-methyl-pyridine-2-carboxylic acid (1-methyl-1H-pyrazol-3-yl)-amide in accordance with the general method of example 1, step 6; using 3,5-Difluorophenylboronic acid instead of 3-Fluorophenyl-boronic acid to yield the final compound as a white crystalline solid, MS (ISP): m/e=329.3 (M+H)$^+$.

Example 54

2'-Chloro-6-methyl-[4,4']bipyridinyl-2-carboxylic acid (1-methyl-1H-pyrazol-3-yl)-amide The title compound, was prepared from 4-Bromo-6-methyl-pyridine-2-carboxylic acid (1-methyl-1H-pyrazol-3-yl)-amide in accordance with the general method of example 1, step 6; using 2-Chloropyridine-4-boronic acid instead of 3-Fluorophenyl-boronic acid to yield the final compound as a white crystalline solid, MS (ISP): m/e=328.1, 330.2 (M+H)$^+$.

Example 55

4-(4-Fluoro-3-trifluoromethyl-phenyl)-6-methyl-pyridine-2-carboxylic acid (1-methyl-1H-pyrazol-3-yl)-amide The title compound, was prepared from 4-Bromo-6-methyl-pyridine-2-carboxylic acid (1-methyl-1H-pyrazol-3-yl)-amide in accordance with the general method of example 1, step 6; using 4-Fluoro-3-trifluoromethylphenylboronic acid instead of 3-Fluorophenyl-boronic acid to yield the final compound as a white crystalline solid, MS (ISP): m/e=379.3 (M+H)$^+$.

Example 56

5-Methoxy-6'-methyl-[3,4']bipyridinyl-2'-carboxylic acid (2-methyl-thiazol-4-yl)-amide Step 1: 4-Bromo-6-methyl-pyridine-2-carboxylic acid (2-methyl-thiazol-4-yl)-amide The title compound, white crystalline solid, MS (ISP): m/e=312.1, 314.1 (M+H)$^+$, was prepared from 4-Bromo-6-methyl-pyridine-2-carboxylic acid ethyl ester in accordance with the general method of example 1. Step 5 was performed using 4-Amino-2-methylthiazole instead of 2-Amino-4-methylthiazole.

Step 2: 5-Methoxy-6'-methyl-[3,4']bipyridinyl-2'-carboxylic acid (2-methyl-thiazol-4-yl)-amide The title compound, was prepared from 4-Bromo-6-methyl-pyridine-2-carboxylic acid (2-methyl-thiazol-4-yl)-amide in accordance with the general method of example 1, step 6; using 3-Methoxy-5-pyridineboronic acid instead of 3-Fluorophenyl-boronic acid to yield the final compound as a white crystalline solid, MS (ISP): m/e=341.1 (M+H)$^+$.

Example 57

6'-Methyl-[3,4']bipyridinyl-2'-carboxylic acid (2-methyl-thiazol-4-yl)-amide

The title compound, was prepared from 4-Bromo-6-methyl-pyridine-2-carboxylic acid (2-methyl-thiazol-4-yl)-amide in accordance with the general method of example 1, step 6; using 3-Pyridineboronic acid instead of 3-Fluorophenyl-boronic acid to yield the final compound as a white crystalline solid, MS (ISP): m/e=311.2 (M+H)$^+$.

Example 58

5-Fluoro-6'-methyl-[3,4']bipyridinyl-2'-carboxylic acid (2-methyl-thiazol-4-yl)-amide The title compound, was prepared from 4-Bromo-6-methyl-pyridine-2-carboxylic acid (2-methyl-thiazol-4-yl)-amide in accordance with the general method of example 1, step 6; using 5-Fluoropyridine-3-boronic acid instead of 3-Fluorophenyl-boronic acid to yield the final compound as a white crystalline solid, MS (ISP): m/e=329.1 (M+H)$^+$.

Example 59

4-(4-Fluoro-phenyl)-6-methyl-pyridine-2-carboxylic acid (2-methyl-thiazol-4-yl)-amide The title compound, was prepared from 4-Bromo-6-methyl-pyridine-2-carboxylic acid (2-methyl-thiazol-4-yl)-amide in accordance with the general method of example 1, step 6; using 4-Fluorophenylboronic acid instead of 3-Fluorophenyl-boronic acid to yield the final compound as a white crystalline solid, MS (ISP): m/e=328.1 (M+H)$^+$.

Example 60

4-(3,5-Difluorophenyl)-6-methyl-pyridine-2-carboxylic acid (2-methyl-thiazol-4-yl)-amide The title compound, was prepared from 4-Bromo-6-methyl-pyridine-2-carboxylic acid (2-methyl-thiazol-4-yl)-amide in accordance with the general method of example 1, step 6; using 3,5-Difluorophenylboronic acid instead of 3-Fluorophenyl-boronic acid to yield the final compound as a white crystalline solid, MS (ISP): m/e=346.1 (M+H)$^+$.

Example 61

2'-Chloro-6-methyl-[4,4']bipyridinyl-2-carboxylic acid (2-methyl-thiazol-4-yl)-amide The title compound, was prepared from 4-Bromo-6-methyl-pyridine-2-carboxylic acid (2-methyl-thiazol-4-yl)-amide in accordance with the general method of example 1, step 6; using 2-Chloropyridine-4-boronic acid instead of 3-Fluorophenyl-boronic acid to yield the final compound as a white crystalline solid, MS (ISP): m/e=345.1, 347.0 (M+H)$^+$.

Example 62

4-(2,5-Dimethyl-2H-pyrazol-3-yl)-6-methyl-pyridine-2-carboxylic acid (2-methyl-thiazol-4-yl)-amide The title compound, was prepared from 4-Bromo-6-methyl-pyridine-2-carboxylic acid (2-methyl-thiazol-4-yl)-amide in accordance with the general method of example 1, step 6; using 1,4-Dimethyl-1H-pyrazole-2-boronic acid instead of 3-Fluorophenyl-boronic acid to yield the final compound as a light yellow crystalline solid, MS (ISP): m/e=328.2 (M+H)$^+$.

Example 63

4-(4-Fluoro-3-trifluoromethyl-phenyl)-6-methyl-pyridine-2-carboxylic acid (2-methyl-thiazol-4-yl)-amide The title compound, was prepared from 4-Bromo-6-methyl-pyridine-2-carboxylic acid (2-methyl-thiazol-4-yl)-amide in accordance with the general method of example 1, step 6; using 4-Fluoro-3-trifluoromethylphenylboronic acid instead of 3-Fluorophenyl-boronic acid to yield the final compound as a white crystalline solid, MS (ISP): m/e=405.9 (M+H)$^+$.

Example 64

4-(3,5-Difluorophenyl)-6-methyl-pyridine-2-carboxylic acid (2-methyl-pyrimidin-4-yl)-amide Step 1: 4-Bromo-6-methyl-pyridine-2-carboxylic acid (2-methyl-pyrimidin-4-yl)-amide The tide compound, white solid, MS (ISP): m/e=307.1, 309.2 (M+H)$^+$, was prepared from 4-Bromo-6-methyl-pyridine-2-carboxylic acid ethyl ester in accordance with the general method of example 1. Step 5 was performed using 4-Amino-2-methylpyrimidine instead of 2-Amino-4-methylthiazole.

Step 2: 4-(3,5-Difluorophenyl)-6-methyl-pyridine-2-carboxylic acid (2-methyl-pyrimidin-4-yl)-amide The title compound, was prepared from 4-Bromo-6-methyl-pyridine-2-carboxylic acid (2-methyl-pyrimidin-4-yl)-amide in accordance with the general method of example 1, step 6; using 3,5-Difluorophenyl boronic acid instead of 3-Fluorophenyl-boronic acid to yield the final compound as a white solid, MS (ISP): m/e=341.1 (M+H)$^+$.

Example 65

6'-Methyl-[3,4']bipyridinyl-2'-carboxylic acid (2-methyl-pyrimidin-4-yl)-amide

The title compound, was prepared from 4-Bromo-6-methyl-pyridine-2-carboxylic acid (2-methyl-pyrimidin-4-yl)-amide in accordance with the general method of example 1, step 6; using 3-Pyridine boronic acid instead of 3-Fluorophenyl-boronic acid to yield the final compound as a white solid, MS (ISP): m/e=306.2 (M+H)$^+$.

Example 66

5-Fluoro-6'-methyl-[3,4']bipyridinyl-2'-carboxylic acid (2-methyl-pyrimidin-4-yl)-amide The title compound, was prepared from 4-Bromo-6-methyl-pyridine-2-carboxylic acid (2-methyl-pyrimidin-4-yl)-amide in accordance with the general method of example 1, step 6; using 3-Fluoropyridine-5-boronic acid instead of 3-Fluorophenyl-boronic acid to yield the final compound as a white crystalline solid, MS (ISP): m/e=324.3 (M+H)$^+$.

Example 67

5-Fluoro-6'-methyl-[3,4']bipyridinyl-2'-carboxylic acid (2-chloro-pyridin-4-yl)-amide Step 1: 4-Bromo-6-methyl-pyridine-2-carboxylic acid (2-chloro-pyridin-4-yl)-amide The title compound, white crystalline solid, MS (ISP): m/e=326.1, 328.0 (M+H)$^+$, was prepared from 4-Bromo-6-methyl-pyridine-2-carboxylic acid ethyl ester in accordance with the general method of example 1. Step 5 was performed using 4-Amino-2-chloropyridine instead of 2-Amino-4-methylthiazole.

Step 2: 5-Fluoro-6'-methyl-[3,4']bipyridinyl-2'-carboxylic acid (2-chloro-pyridin-4-yl)-amide The title compound, was prepared from 4-Bromo-6-methyl-pyridine-2-carboxylic acid (2-chloro-pyridin-4-yl)-amide in accordance with the general method of example 1, step 6; using 5-Fluoropyridine-3-boronic acid instead of 3-Fluorophenyl-boronic acid to yield the final compound as a white crystalline solid, MS (ISP): m/e=343.0, 345.2 (M+H)$^+$.

Example 68

4-(3,4-Difluorophenyl)-6-methyl-pyridine-2-carboxylic acid (2-chloro-pyridin-4-yl)-amide The title compound, was prepared from 4-Bromo-6-methyl-pyridine-2-carboxylic acid (2-chloro-pyridin-4-yl)-amide in accordance with the general method of example 1, step 6; using 3,4-Difluorophenylboronic acid instead of 3-Fluorophenyl-boronic acid to yield the final compound as a white crystalline solid, MS (ISP): m/e=360.1, 362.2 (M+H)$^+$.

Example 69

6'-Methyl-[3,4']bipyridinyl-2'-carboxylic acid (2-chloro-pyridin-4-yl)-amide

The title compound, was prepared from 4-Bromo-6-methyl-pyridine-2-carboxylic acid (2-chloro-pyridin-4-yl)-amide in accordance with the general method of example 1, step 6; using 3-Pyridineboronic acid instead of 3-Fluorophenyl-boronic acid to yield the final compound as a white crystalline solid, MS (ISP): m/e=325.2, 327.1 (M+H)$^+$.

Example 70

4-(3,5-Difluorophenyl)-6-methyl-pyridine-2-carboxylic acid (2-chloro-pyridin-4-yl)-amide The title compound, was prepared from 4-Bromo-6-methyl-pyridine-2-carboxylic acid (2-chloro-pyridin-4-yl)-amide in accordance with the general method of example 1, step 6; using 3,5-Difluorophenylboronic acid-instead of 3-Fluorophenyl-boronic acid to yield the final compound as a white crystalline solid, MS (ISP): m/e=360.1, 362.2 (M+H)$^+$.

Example 71

4-(3-Chloro-4-fluoro-phenyl)-6-methyl-pyridine-2-carboxylic acid (2-chloro-pyridin-4-yl)-amide The title compound, was prepared from 4-Bromo-6-methyl-pyridine-2-carboxylic acid (2-chloro-pyridin-4-yl)-amide in accordance with the general method of example 1, step 6; using 3-Chloro-4-fluorophenylboronic acid instead of 3-Fluorophenyl-boronic acid to yield the final compound as a white crystalline solid, MS (ISP): m/e=376.2, 378.2 (M+H)$^+$.

Example 72

4-(3,4-Difluorophenyl)-6-methyl-pyridine-2-carboxylic acid (2-methyl-pyridin-4-yl)-amide Step 1: 4-Bromo-6-methyl-pyridine-2-carboxylic acid (2-methyl-pyridin-4-yl)-amide The title compound, white crystalline solid, MS (ISP): m/e 306.1, 308.1 (M+H)$^+$, was prepared from 4-Bromo-6-methyl-pyridine-2-carboxylic acid ethyl ester in accordance with the general method of example 1. Step 5 was performed using 4-Amino-2-methylpyridine instead of 2-Amino-4-methylthiazole.

Step 2: 4-(3,4-Difluorophenyl)-6-methyl-pyridine-2-carboxylic acid (2-methyl-pyridin-4-yl)-amide The title compound, was prepared from 4-Bromo-6-methyl-pyridine-2-carboxylic acid (2-methyl-pyridin-4-yl)-amide in accordance with the general method of example 1, step 6; using 3,4-Difluorophenylboronic acid instead of 3-Fluorophenyl-boronic acid to yield the final compound as a white waxy solid, MS (ISP): m/e=340.2 (M+H)$^+$.

Example 73

5-Fluoro-6'-methyl-[3,4']bipyridinyl-2'-carboxylic acid (2-methyl-pyridin-4-yl)-amide The title compound, was prepared from 4-Bromo-6-methyl-pyridine-2-carboxylic acid (2-methyl-pyridin-4-yl)-amide in accordance with the general method of example 1, step 6; using 5-Fluoropyridine-3-boronic acid instead of

Example 74

4-(3-Chloro-4-fluoro-phenyl)-6-methyl-pyridine-2-carboxylic acid (2-methyl-pyridin-4-yl)-amide The title compound, was prepared from 4-Bromo-6-methyl-pyridine-2-carboxylic acid (2-methyl-pyridin-4-yl)-amide in accordance with the general method of example 1, step 6; using 3-Chloro-4-fluorophenylboronic acid instead of 3-Fluorophenyl-boronic acid to yield the final compound as a white waxy solid, MS (ISP): m/e=356.0, 358.2 (M+H)$^+$.

Example 75

6'-Methyl-[3,4']bipyridinyl-2'-carboxylic acid (2-methyl-pyridin-4-yl)-amide

The title compound, was prepared from 4-Bromo-6-methyl-pyridine-2-carboxylic acid (2-methyl-pyridin-4-yl)-amide in accordance with the general method of example 1, step 6; using 3-Pyridineboronic acid instead of 3-Fluorophenyl-boronic acid to yield the final compound as a white crystalline solid, MS (ISP): m/e=305.2 (M+H)$^+$.

Example 76

4-(3,5-Difluorophenyl)-6-methyl-pyridine-2-carboxylic acid (2-methyl-pyridin-4-yl)-amide The title compound, was prepared from 4-Bromo-6-methyl-pyridine-2-carboxylic acid (2-methyl-pyridin-4-yl)-amide in accordance with the general method of example 1, step 6; using 3,5-Difluorophenylboronic acid instead of 3-Fluorophenyl-boronic acid to yield the final compound as a light yellow solid, MS (ISP): m/e=340.2 (M+H)$^+$.

Example 77

5-Cyano-6'-methyl-[3,4']bipyridinyl-2'-carboxylic acid (2-methyl-pyridin-4-yl)-amide The title compound, was prepared from 4-Bromo-6-methyl-pyridine-2-carboxylic acid (2-methyl-pyridin-4-yl)-amide in accordance with the general method of example 1, step 6; using 5-(4,4,5,5-Tetramethyl-[1,3,2]dioxaborolan-2-yl)-nicotinonitrile instead of 3-Fluorophenyl-boronic acid to yield the final compound as a white solid, MS (ISP): m/e=330.2 (M+H)$^+$.

Example 78

4-(3,5-Difluorophenyl)-6-methyl-pyridine-2-carboxylic acid (4-trifluoromethyl-thiazol-2-yl)-amide Step 1: 4-Bromo-6-methyl-pyridine-2-carboxylic acid (4-trifluoromethyl-thiazol-2-yl)-amide The title compound, white solid, MS (ISP): m/e=365.9, 368.0 (M+H)$^+$, was prepared from 4-Bromo-6-methyl-pyridine-2-carboxylic acid ethyl ester in accordance with the general method of example 1. Step 5 was performed using 2-Amino-4-trifluoromethylthiazole instead of 2-Amino-4-methylthiazole.

Step 2: 4-(3,5-Difluorophenyl)-6-methyl-pyridine-2-carboxylic acid (4-trifluoromethyl-thiazol-2-yl)-amide The title compound, was prepared from 4-Bromo-6-methyl-pyridine-2-carboxylic acid (4-trifluoromethyl-thiazol-2-yl)-amide in accordance with the general method of example 1, step 6; using 3,5-Difluorophenylboronicacid instead of 3-Fluorophenyl-boronic acid to yield the final compound as a white oil, MS (ISP): m/e=410.1 (M+H)$^+$.

Example 79

5-Fluoro-6'-methyl-[3,4']bipyridinyl-2'-carboxylic acid (4-trifluoromethyl-thiazol-2-yl)-amide The title compound, was prepared from 4-Bromo-6-methyl-pyridine-2-carboxylic acid (4-trifluoromethyl-thiazol-2-yl)-amide in accordance with the general method of example 1, step 6; using 5-Fluoro-3-pyridineboronicacid instead of 3-Fluorophenyl-boronic acid to yield the final compound as a light yellow solid, MS (ISP): m/e=393.1 (M+H)$^+$.

Example 80

4-(3-Fluoro-phenyl)-6-methyl-pyridine-2-carboxylic acid (4-trifluoromethyl-thiazol-2-yl)-amide The title compound, was prepared from 4-Bromo-6-methyl-pyridine-2-carboxylic acid (4-trifluoromethyl-thiazol-2-yl)-amide in accordance with the general method of example 1, step 6; using 3-Fluorophenylboronic acid instead of 3-Fluorophenyl-boronic acid to yield the final compound as a white solid, MS (ISP): m/e=392.1 (M+H)$^+$.

Example 81

4-(3-Cyanophenyl)-6-methyl-pyridine-2-carboxylic acid (4-trifluoromethyl-thiazol-2-yl)-amide The title compound, was prepared from 4-Bromo-6-methyl-pyridine-2-carboxylic acid (4-trifluoromethyl-thiazol-2-yl)-amide in accordance with the general method of example 1, step 6; using 3-Cyanophenylboronic acid instead of 3-Fluorophenyl-boronic acid to yield the final compound as a white solid, MS (ISP): m/e=399.2 (M+H)$^+$.

Example 82

4-(2-Chloro-phenyl)-6-methyl-pyridine-2-carboxylic acid (4-trifluoromethyl-thiazol-2-yl)-amide The title compound, was prepared from 4-Bromo-6-methyl-pyridine-2-carboxylic acid (4-trifluoromethyl-thiazol-2-yl)-amide in accordance with the general method of example 1, step 6; using 2-Chlorophenylboronic acid instead of 3-Fluorophenyl-boronic acid to yield the final compound as a white solid, MS (ISP): m/e=408.1 (M+H)$^+$.

Example 83

6'-Methyl-[3,4']bipyridinyl-2'-carboxylic acid (4-trifluoromethyl-thiazol-2-yl)-amide The title compound, was prepared from 4-Bromo-6-methyl-pyridine-2-carboxylic acid (4-trifluoromethyl-thiazol-2-yl)-amide in accordance with the general method of (continued: 3-Fluorophenyl-boronic acid to yield the final compound as a white crystalline solid, MS (ISP): m/e=323.2 (M+H)$^+$.)

example 1, step 6; using 3-Pyridineboronic acid instead of 3-Fluorophenyl-boronic acid to yield the final compound as a white solid, MS (ISP): m/e=365 (M+H)⁺.

Example 84

2'-Chloro-6-methyl-[4,4']bipyridinyl-2-carboxylic acid (4-trifluoromethyl-thiazol-2-yl)-amide The title compound, was prepared from 4-Bromo-6-methyl-pyridine-2-carboxylic acid (4-trifluoromethyl-thiazol-2-yl)-amide in accordance with the general method of example 1, step 6; using 2-Chloropyridine-4-boronic acid instead of 3-Fluorophenyl-boronic acid to yield the final compound as a white solid, MS (ISP): m/e=409.1 (M+H)⁺.

Example 85

4-(2,5-Dimethyl-2H-pyrazol-3-yl)-6-methyl-pyridine-2-carboxylic acid (4-trifluoro-methyl-thiazol-2-yl)-amide The tide compound, was prepared from 4-Bromo-6-methyl-pyridine-2-carboxylic acid (4-trifluoromethyl-thiazol-2-yl)-amide in accordance with the general method of example 1, step 6; using 1,4-Dimethyl-1H-pyrazole-2-boronic acid instead of 3-Fluorophenyl-boronic acid to yield the final compound as a white solid, MS (ISP): m/e=392.1 (M+H)⁺.

Example 86

4-(3,5-Difluorophenyl)-6-methyl-pyridine-2-carboxylic acid (5-methyl-thiazol-2-yl)-amide Step 1: 4-Bromo-6-methyl-pyridine-2-carboxylic acid (5-methyl-thiazol-2-yl)-amide The title compound, light yellow solid, MS (ISP): m/e=312.1, 314.1 (M+H)⁺, was prepared from 4-Bromo-6-methyl-pyridine-2-carboxylic acid ethyl ester in accordance with the general method of example 1. Step 5 was performed using 2-Amino-5-methylthiazole instead of 2-Amino-4-methylthiazole.

Step 2: 4-(3,5-Difluorophenyl)-6-methyl-pyridine-2-carboxylic acid (5-methyl-thiazol-2-yl)-amide The title compound, was prepared from 4-Bromo-6-methyl-pyridine-2-carboxylic acid (5-methyl-thiazol-2-yl)- in accordance with the general method of example 1, step 6;. using 3,5-Difluorophenylboronic acid instead of 3-Fluorophenyl-boronic acid to yield the final compound as a white solid, MS (ISP): m/e=346.1 (M+H)⁺.

Example 87

6'-Methyl-[3,4']bipyridinyl-2'-carboxylic acid (6-methyl-pyridin-2-yl)-amide

Step 1: 4-Bromo-6-methyl-pyridine-2-carboxylic acid (6-methyl-pyridin-2-yl)-amide The title compound, white solid, MS (ISP): m/e=306.1, 308.1 (M+H)⁺, was prepared from 4-Bromo-6-methyl-pyridine-2-carboxylic acid ethyl ester in accordance with the general method of example 1. Step 5 was performed using 2-Amino-6-methylpyridine instead of 2-Amino-4-methylthiazole.

Step 2: 6'-Methyl-[3,4']bipyridinyl-2'-carboxylic acid (6-methyl-pyridin-2-yl)-amide The title compound, was prepared from 4-Bromo-6-methyl-pyridine-2-carboxylic acid (6-methyl-pyridin-2-yl)-amide in accordance with the general method of example 1, step 6; using 3-Pyridineboronic acid instead of 3-Fluorophenyl-boronic acid to yield the final compound as a white solid, MS (ISP): m/e=305.2 (M+H)⁺.

Example 88

6'-Methyl-[3,4']bipyridinyl-2'-carboxylic acid (6-chloro-pyridin-2-yl)-amide

Step 1: 4-Bromo-6-methyl-pyridine-2-carboxylic acid (6-chloro-pyridin-2-yl)-amide The title compound, white solid, MS (ISP): m/e=326.1, 328.0 (M+H)⁺, was prepared from 4-Bromo-6-methyl-pyridine-2-carboxylic acid ethyl ester in accordance with the general method of example 1. Step 5 was performed using 2-Amino-6-chloropyridine instead of 2-Amino-4-methylthiazole.

Step 2: 6'-Methyl-[3,4']bipyridinyl-2'-carboxylic acid (6-chloro-pyridin-2-yl)-amide The title compound, was prepared from 4-Bromo-6-methyl-pyridine-2-carboxylic acid (6-chloro-pyridin-2-yl)-amide in accordance with the general method of example 1, step 6; using 3-Pyridineboronic acid instead of 3-Fluorophenyl-boronic acid to yield the final compound as a white solid, MS (ISP): m/e=325.2, 327.1 (M+H)⁺.

Example 89

6'-Methyl-[3,4']bipyridinyl-2'-carboxylic acid (4-difluoromethyl-thiazol-2-yl)-amide Step 1: (4-Difluoromethylthiazol-2-yl)-carbamic acid tert-butyl ester To a solution of 1.25 g (5.5 mmol) (4-formyl-thiazol-2-yl)-carbamic acid tert-butyl ester (CAS: [494769-34-5]) in 30 ml of dry methylene chloride were added 2.15 ml (16.4 mmol) diethylaminosulfur trifluoride (DAST). The mixture was stirred at room temperature for 16 hours. The reaction mixture was quenched with sat. NaHCO3- solution and extracted with water and methylene chloride. The combined organic extracts were dried with sodium sulfate, filtered and evaporated. The crude product was purified by flash chromatography on silica gel (heptane/ethyl acetate 4:1). The desired compound was obtained as a yellow solid (810 mg, 60%), MS: m/e=251.2 (M+H)⁺.

Step 2: 2-Amino-4-difluoromethylthiazole (2-Difluoromethyl-thiazol-4-yl)-carbamic acid tert-butyl ester (1.0 g, 4.0 mmol) was dissolved in 10 ml ethyl acetate and 8M HCl in ethanol (10.0 ml, 81 mmol) was added. The reaction mixture was stirred for 2 hrs at room temperature.

The reaction mixture was evaporated and extracted carefully with sat. NaHCO₃— solution and two times ethyl acetate. The combined organic extracts were washed with brine, dried with sodium sulfate, filtered and evaporated. The desired compound was obtained as a light brown solid (410 mg, 69%), MS: m/e=152.1 (M+H)⁺.

Step 3: 4-Bromo-6-methyl-pyridine-2-carboxylic acid (4-difluoromethyl-thiazol-2-yl)-amide The title compound, light brown solid, MS (ISP): m/e=348.1, 350.1 (M+H)⁺, was prepared from 4-Bromo-6-methyl-pyridine-2-carboxylic acid ethyl ester in accordance with the general method of example 1. Step 5 was performed using 2-Amino-4-difluoromethylthiazole instead of 2-Amino-4-methylthiazole.

Step 4: 6'-Methyl-[3,4']bipyridinyl-2'-carboxylic acid (4-difluoromethyl-thiazol-2-yl)-amide The title compound, was prepared from 4-Bromo-6-methyl-pyridine-2-carboxylic acid (4-difluoromethyl-thiazol-2-yl)-amide in accordance with the general method of example 1, step 6; using 3-Pyridineboronic acid instead of 3-Fluorophenyl-boronic acid to yield the final compound as a white solid, MS (ISP): m/e=347.2 (M+H)⁺.

Example 90

2'-Chloro-6-methyl-[4,4']bipyridinyl-2-carboxylic acid (4-difluoromethyl-thiazol-2-yl)-amide The title compound, was prepared from 4-Bromo-6-methyl-pyridine-2-carboxylic acid (4-difluoromethyl-thiazol-2-yl)-amide in accordance with the general method of example 1, step 6; using 2-Chloropyridine-4-boronic acid instead of 3-Fluorophenyl-boronic acid to yield the final compound as a white solid, MS (ISP): m/e=391.0 (M+H)⁺.

Example 91

4-(2,5-Dimethyl-2H-pyrazol-3-yl)-6-methyl-pyridine-2-carboxylic acid (5-chloro-pyridin-2-yl)-amide Step 1: 4-Bromo-6-methyl-pyridine-2-carboxylic acid (5-chloro-pyridin-2-yl)-amide The title compound, light yellow solid, MS (ISP): m/e=326.1, 328.1 (M+H)⁺, was prepared from 4-Bromo-6-methyl-pyridine-2-carboxylic acid ethyl ester in accordance with the general method of example 1. Step 5 was performed using 2-Amino-5-chloropyridine instead of 2-Amino-4-methylthiazole.

Step 2: 4-(2,5-Dimethyl-2H-pyrazol-3-yl)-6-methyl-pyridine-2-carboxylic acid (5-chloro-pyridin-2-yl)-amide The title compound, was prepared from 4-Bromo-6-methyl-pyridine-2-carboxylic acid (5-chloro-pyridin-2-yl)-amide in accordance with the general method of example 1, step 6; using 1,4-Dimethyl-1H-pyrazole-2-boronic acid instead of 3-Fluorophenyl-boronic acid to yield the final compound as a light yellow solid, MS: m/e=342.1, 344.0 (M+H)⁺.

Example 92

4-(3,5-Difluorophenyl)-6-methyl-pyridine-2-carboxylic acid (5-chloro-pyridin-2-yl)-amide The title compound, was prepared from 4-Bromo-6-methyl-pyridine-2-carboxylic acid (5-chloro-pyridin-2-yl)-amide in accordance with the general method of example 1, step 6; using 3,5-Diphenyl boronic acid instead of 3-Fluorophenyl-boronic acid to yield the final compound as a white solid, MS (ISP): m/e=360.1, 362.0 (M+H)⁺.

Example 93

4-(3-Chloro-4-fluoro-phenyl)-6-methyl-pyridine-2-carboxylic acid (5-chloro-pyridin-2-yl)-amide The title compound, was prepared from 4-Bromo-6-methyl-pyridine-2-carboxylic acid (5-chloro-pyridin-2-yl)-amide in accordance with the general method of example 1, step 6; using 3-Chloro-4-fluorophenyl boronic acid instead of 3-Fluorophenyl-boronic acid to yield the final compound as a white solid, MS (ISP): m/e=376.2, 378.3 (M+H)⁺.

Example 94

6'-Methyl-[3,4']bipyridinyl-2'-carboxylic acid (5-chloro-pyridin-2-yl)-amide

The title compound, was prepared from 4-Bromo-6-methyl-pyridine-2-carboxylic acid (5-chloro-pyridin-2-yl)-amide in accordance with the general method of example 1, step 6; using 3-Pyridylboronic acid instead of 3-Fluorophenyl-boronic acid to yield the final compound as a light yellow solid, MS (ISP): m/e=325.2 (M+H)⁺.

Example 95

6'-Methyl-[3,4']bipyridinyl-2'-carboxylic acid (3-cyanophenyl)-amide

Step 1: 4-Bromo-6-methyl-pyridine-2-carboxylic acid (3-cyanophenyl)-amide

The title compound, white solid, MS (ISP): m/e=316.0, 318.0 (M+H)⁺, was prepared from 4-Bromo-6-methyl-pyridine-2-carboxylic acid ethyl ester in accordance with the general method of example 1. Step 5 was performed using 3-Aminobenzonitrile instead of 2-Amino-4-methylthiazole.

Step 2: 6'-Methyl-[3,4']bipyridinyl-2'-carboxylic acid (3-cyanophenyl)-amide

The title compound, was prepared from 4-Bromo-6-methyl-pyridine-2-carboxylic acid (3-cyanophenyl)-amide in accordance with the general method of example 1, step 6; using 3-Pyridineboronic acid instead of 3-Fluorophenyl-boronic acid to yield the final compound as a white solid, MS (ISP): m/e=315.1 (M+H)⁺.

Example 96

4-(3,5-Difluorophenyl)-6-methyl-pyridine-2-carboxylic acid (3-cyanophenyl)-amide The title compound, was prepared from 4-Bromo-6-methyl-pyridine-2-carboxylic acid (3-cyanophenyl)-amide in

Example 97

5-Fluoro-6'-methyl-[3,4']bipyridinyl-2'-carboxylic acid (3-cyanophenyl)-amide

The title compound, was prepared from 4-Bromo-6-methyl-pyridine-2-carboxylic acid (3-cyanophenyl)-amide in accordance with the general method of example 1, step 6; using 5-Fluoropyridine-3-boronic acid instead of 3-Fluorophenyl-boronic acid to yield the final compound as a off-white solid, MS (ISP): m/e=333.2 (M+H)$^+$.

Example 98

6,2'-Dimethyl-[4,4']bipyridinyl-2-carboxylic acid (3-cyanophenyl)-amide

The title compound, was prepared from 4-Bromo-6-methyl-pyridine-2-carboxylic acid (3-cyanophenyl)-amide in accordance with the general method of example 1, step 6; using RO5135690-000-001 instead of 3-Fluorophenyl-boronic acid to yield the final compound as a white solid, MS (ISP): m/e=329.1 (M+H)$^+$.

Example 99

4-(3-Chloro-4-fluoro-phenyl)-3,6-dimethyl-pyridine-2-carboxylic acid (4-methyl-thiazol-2-yl)-amide Step 1: 3,6-Dimethyl-4-nitro-pyridine-2-carbonitrile The title compound, was prepared by treatment of 2,5-Dimethyl-4-nitropyridine-N-oxide (CAS: [21816-42-2], J. Heterocyclic Chem. 34(3), 727(1997)) with Dimethylsulfate and Potassium cyanide in accordance with the general method of example 1, step 1 to yield the title compound as a brown solid.

Step 2: 3,6-Dimethyl-4-nitro-pyridine-2-carboxylic acid

The title compound, was prepared by acidic hydrolysis of 3,6-Dimethyl-4-nitro-pyridine-2-carbonitrile with 91% sulfuric acid and sodium nitrite in accordance with the general method of example 1, step 2 to yield the title compound as a light yellow solid, MS (ISP): m/e=197.1 (M+H)$^+$.

Step 3: 4-Bromo-3,6-dimethyl-pyridine-2-carboxylic acid

The title compound, was prepared by treatment of 3,6-Dimethyl-4-nitro-pyridine-2-carboxylic acid with 49% hydrobrornic acid at 101° C. in accordance with the general method of example 1, step 3 to yield the title compound as an amorphous yellow solid, which is directly used in the next step without further purification.

Step 4: 4-Bromo-3,6-dimethyl-pyridine-2-carboxylic acid ethyl ester

The crude material from the preceding step was esterified in Ethanol/sulfuric acid in accordance with the general method of example 1, step 4 to yield the title compound as a light yellow oil, MS (ISP): m/e=258.1, 260.2 (M+H)$^+$.

Step 5: 4-Bromo-3,6-dimethyl-pyridine-2-carboxylic acid (4-methyl-thiazol-2-yl)-amide The title compound, white solid, MS (ISP): m/e=326.1, 328.0 (M+H)$^+$, was prepared from 4-Bromo-3,6-dimethyl-pyridine-2-carboxylic acid ethyl ester and 2-Amino-4-methylthiazole in accordance with the general method of example 1, step 5.

Step 6: 4-(3-Chloro-4-fluoro-phenyl)-3,6-dimethyl-pyridine-2-carboxylic acid (4-methyl-thiazol-2-yl)-amide The title compound, was prepared from 4-Bromo-3,6-dimethyl-pyridine-2-carboxylic acid (4-methyl-thiazol-2-yl)-amide and 3-Chloro-4-fluorophenylboronic acid in accordance with the general method of example 1, step 6 to yield the final compound as a light yellow solid, MS (ISP): m/e=376.2, 378.2 (M+H)$^+$.

Example 100

4-(3,5-Difluorophenyl)-3,6-dimethyl-pyridine-2-carboxylic acid (4-methyl-thiazol-2-yl)-amide The title compound, was prepared from 4-Bromo-3,6-dimethyl-pyridine-2-carboxylic acid (4-methyl-thiazol-2-yl)-amide in accordance with the general method of example 1, step 6; using 3,5-Difluorophenylboronic acid to yield the final compound as a light brown solid, MS (ISP): m/e=360.1 (M+H)$^+$.

Example 101

5-Fluoro-3',6'-dimethyl-[3,4']bipyridinyl-2'-carboxylic acid (4-methyl-thiazol-2-yl)-amide The title compound, was prepared from 4-Bromo-3,6-dimethyl-pyridine-2-carboxylic acid (4-methyl-thiazol-2-yl)-amide in accordance with the general method of example 1, step 6; using 3,5-Difluorophenylboronic acid to yield the final compound as a white solid, MS (ISP): m/e=343.0 (M+H)$^+$.

Example 102

4-(4-Fluoro-phenyl)-3,6-dimethyl-pyridine-2-carboxylic acid (4-methyl-thiazol-2-yl)-amide The title compound, was prepared from 4-Bromo-3,6-dimethyl-pyridine-2-carboxylic acid (4-methyl-thiazol-2-yl)-amide in accordance with the general method of example 1, step 6; using 4-Fluorophenylboronic acid to yield the final compound as a off-white solid, MS (ISP): m/e=342.1 (M+H)$^+$.

Example 103

3',6'-Dimethyl-[3,4']bipyridinyl-2'-carboxylic acid (4-methyl-thiazol-2-yl)-amide The title compound, was prepared from 4-Bromo-3,6-dimethyl-pyridine-2-carboxylic acid (4-methyl-thiazol-2-yl)-amide in accordance with the general method of example 1, step 6; using 3-Pyridineboronic acid to yield the final compound as a white solid, MS (ISP): m/e=325.3 (M+H)+.

Example 104

3,6-Dimethyl-4-pyrimidin-5-yl-pyridine-2-carboxylic acid (4-methyl-thiazol-2-yl)-amide The title compound, was prepared from 4-Bromo-3,6-dimethyl-pyridine-2-carboxylic acid (4-methyl-thiazol-2-yl)-amide in accordance with the general method of example 1, step 6; using Pyrimidin-5-boronic acid to yield the final compound as a white solid, MS (ISP): m/e=326.2 (M+H)+.

Example 105

4-(3,4-Difluorophenyl)-3,6-dimethyl-pyridine-2-carboxylic acid (4-methyl-thiazol-2-yl)-amide The title compound, was prepared from 4-Bromo-3,6-dimethyl-pyridine-2-carboxylic acid (4-methyl-thiazol-2-yl)-amide in accordance with the general method of example 1, step 6; using 3-4-Difluorophenylboronic acid to yield the final compound as a light yellow solid, MS (ISP): m/e=360.1 (M+H)+.

Example 106

4-(2,5-Dimethyl-2H-pyrazol-3-yl)-3,6-dimethyl-pyridine-2-carboxylic acid (4-methyl-thiazol-2-yl)-amide The title compound, was prepared from 4-Bromo-3,6-dimethyl-pyridine-2-carboxylic acid (4-methyl-thiazol-2-yl)-amide in accordance with the general method of example 1, step 6; using 1,4-Dimethyl-1H-pyrazole-2-boronic acid to yield the final compound as a light yellow solid, MS (ISP): m/e=342.1 (M+H)+.

Example 107

2'-Chloro-3,6-dimethyl-[4,4']bipyridinyl-2-carboxylic acid (4-methyl-thiazol-2-yl)-amide The title compound, was prepared from 4-Bromo-3,6-dimethyl-pyridine-2-carboxylic acid (4-methyl-thiazol-2-yl)-amide in accordance with the general method of example 1, step 6; using 2-Chloropyridine-4-boronic acid to yield the final compound as a white solid, MS (ISP): m/e=359.1, 361.1 (M+H)+.

Example 108

3,6,2'-Trimethyl-[4,4']bipyridinyl-2-carboxylic acid (4-methyl-thiazol-2-yl)-amide The title compound, was prepared from 4-Bromo-3,6-dimethyl-pyridine-2-carboxylic acid (4-methyl-thiazol-2-yl)-amide in accordance with the general method of example 1, step 6; using RO5135690-000-001 to yield the final compound as a light yellow waxy solid, MS (ISP): M/e=339.1 (M+H)+.

Example 109

4-(2,5-Dimethyl-2H-pyrazol-3-yl)-3,6-dimethyl-pyridine-2-carboxylic acid (2-methyl-thiazol-4-yl)-amide The title compound, was prepared from 4-Bromo-3,6-dimethyl-pyridine-2-carboxylic acid (2-methyl-thiazol-4-yl)-amide (from ester, Analog, Ex 99) in accordance with the general method of example 1, step 6; using 1,4-Dimethyl-1H-pyrazole-2-boronic acid to yield the final compound as a light brown solid, MS (ISP): m/e=342.1 (M+H)+.

Example 110

2'-Chloro-3,6-dimethyl-[4,4']bipyridinyl-2-carboxylic acid (2-methyl-thiazol-4-yl)-amide The title compound, was prepared from 4-Bromo-3,6-dimethyl-pyridine-2-carboxylic acid (2-methyl-thiazol-4-yl)-amide in accordance with the general method of example 1, step 6; using 2-Chloropyridine-4-boronic acid to yield the final compound as a off-white solid, MS (ISP): m/e=359.1, 361.1 (M+H)+.

Example 111

4-(3,5-Difluorophenyl)-3,6-dimethyl-pyridine-2-carboxylic acid (2-methyl-thiazol-4-yl)-amide The title compound, was prepared from 4-Bromo-3,6-dimethyl-pyridine-2-carboxylic acid (2-methyl-thiazol-4-yl)-amide in accordance with the general method of example 1, step 6; using 3,5-Difluorophenylboronic acid to yield the final compound as a off-white solid, MS (ISP): m/e=360.1 (M+H)+.

Example 112

3',6'-Dimethyl-[3,4']bipyridinyl-2'-carboxylic acid (2-methyl-thiazol-4-yl)-amide The title compound, was prepared from 4-Bromo-3,6-dimethyl-pyridine-2-carboxylic acid (2-methyl-thiazol-4-yl)-amide in accordance with the general method of example 1, step 6; using 3-Pyridineboronic acid to yield the final compound as a white solid, MS, (ISP): m/e=325.2 (M+H)+.

Example 113

4-(3-Chloro-4-fluoro-phenyl)-3,6-dimethyl-pyridine-2-carboxylic acid (2-methyl-thiazol-4-yl)-amide The title compound, was prepared from 4-Bromo-3,6-dimethyl-pyridine-2-carboxylic acid (2-methyl-thiazol-4-yl)-amide in accordance with the general method of example 1, step 6; using 3-Chloro-4-fluorophenylboronic acid to yield the final compound as a white solid, MS (ISP): m/e=376.2, 378.2 (M+H)+.

Example 114

5-Fluoro-3',6'-dimethyl-[3,4']bipyridinyl-2'-carboxylic acid (2-methyl-thiazol-4-yl)-amide The title compound, was prepared from 4-Bromo-3,6-dimethyl-pyridine-2-carboxylic acid (2-methyl-thiazol-4-yl)- amide in accordance with the general method of example 1, step 6; using 5-Fluoropyridine-3-boronic acid to yield the final compound as a white solid, MS (ISP): m/e=343 (M+H)$^+$.

Example 115

3,6-Dimethyl-4-pyrimidin-5-yl-pyridine-2-carboxylic acid (2-methyl-thiazol-4-yl)-amide The title compound, was prepared from 4-Bromo-3,6-dimethyl-pyridine-2-carboxylic acid (2-methyl-thiazol-4-yl)-amide in accordance with the general method of example 1, step 6; using Pyrimidin-5-boronic acid to yield the final compound as a white solid, MS (ISP): m/e=326.2 (M+H)$^+$.

Example 116

4-(4-Fluoro-phenyl)-3,6-dimethyl-pyridine-2-carboxylic acid (2-methyl-thiazol-4-yl)-amide The title compound, was prepared from 4-Bromo-3,6-dimethyl-pyridine-2-carboxylic acid (2-methyl-thiazol-4-yl)-amide in accordance with the general method of example 1, step 6; using 4-Fluorophenylboronic acid to yield the final compound as a white solid, MS (ISP): m/e=342.1 (M+H)$^+$.

Example 117

4-(3,4-Difluorophenyl)-3,6-dimethyl-pyridine-2-carboxylic acid (2-methyl-thiazol-4-yl)-amide The title compound, was prepared from 4-Bromo-3,6-dimethyl-pyridine-2-carboxylic acid (2-methyl-thiazol-4-yl)-amide in accordance with the general method of example 1, step 6; using 3-4-Difluorophenylboronic acid to yield the final compound as a white solid, MS (ISP): m/e=360.1 (M+H)$^+$.

Example 118

4-(4-Fluoro-phenyl)-3,6-dimethyl-pyridine-2-carboxylic acid (1-methyl-1H-pyrazol-3-yl)-amide The title compound, was prepared from 4-Bromo-3,6-dimethyl-pyridine-2-carboxylic acid (1-methyl-1H-pyrazol-3-yl)-amide (from ester, Analog, Ex 99) in accordance with the general method of example 1, step 6; using 4-Fluorophenylboronic acid to yield the final compound as a white solid, MS (ISP): m/e=325.3, 326.2 (M+H)$^+$.

Example 119

4-(3,5-Difluorophenyl)-3,6-dimethyl-pyridine-2-carboxylic acid (1-methyl-1H-pyrazol-3-yl)-amide The title compound, was prepared from 4-Bromo-3,6-dimethyl-pyridine-2-carboxylic acid (1-methyl-1H-pyrazol-3-yl)-amide in accordance with the general method of example 1, step 6; using 3,5-Difluorophenylboronic acid to yield the final compound as a white solid, MS (ISP): m/e=343.1 (M+H)$^+$.

Example 120

3',6'-Dimethyl-[3,4']bipyridinyl-2'-carboxylic acid (1-methyl-1H-pyrazol-3-yl)-amide The title compound, was prepared from 4-Bromo-3,6-dimethyl-pyridine-2-carboxylic acid (1-methyl-1H-pyrazol-3-yl)-amide in accordance with the general method of example 1, step 6; using 3-Pyridineylboronic acid to yield the final compound as a white solid, MS (ISP): m/e=308.3 (M+H)$^+$.

Example 121

3,6-Dimethyl-4-pyrimidin-5-yl-pyridine-2-carboxylic acid (1-methyl-1H-pyrazol-3-yl)-amide The title compound, was prepared from 4-Bromo-3,6-dimethyl-pyridine-2-carboxylic acid (1-methyl-1H-pyrazol-3-yl)-amide in accordance with the general method of example 1, step 6; using Pyrimidin-5-boronic acid to yield the final compound as a off-white solid, MS (ISP): m/e=309.3 (M+H)$^+$.

Example 122

4-(3,4-Difluorophenyl)-3,6-dimethyl-pyridine-2-carboxylic acid (1-methyl-1H-pyrazol-3-yl)-amide The title compound, was prepared from 4-Bromo-3,6-dimethyl-pyridine-2-carboxylic acid (1-methyl-1H-pyrazol-3-yl)-amide in accordance with the general method of example 1, step 6; using 3,4-Difluorophenylboronic acid to yield the final compound as a white solid, MS (ISP): m/e=343.1 (M+H)$^+$.

Example 123

5-Fluoro-3',6'-dimethyl-[3,4']bipyridinyl-2'-carboxylic acid (1-methyl-1H-pyrazol-3-yl)-amide The title compound, was prepared from 4-Bromo-3,6-dimethyl-pyridine-2-carboxylic acid (1-methyl-1H-pyrazol-3-yl)-amide in accordance with the general method of example 1, step 6; using 5-Fluoropyridine-3-boronic acid to yield the final compound as a white solid, MS (ISP): m/e=326.2 (M+H)$^+$.

Example 124

4-(2,5-Dimethyl-2H-pyrazol-3-yl)-3,6-dimethyl-pyridine-2-carboxylic acid (1-methyl-1H-pyrazol-3-yl)-amide The title compound, was prepared from 4-Bromo-3,6-dimethyl-pyridine-2-carboxylic acid (1-methyl-1H-pyrazol-3-yl)-amide in accordance with the general method of example 1, step 6; using 1,4-Dimethyl-1H-pyrazole-2-boronic acid to yield the final compound as a white waxy solid, MS (ISP): m/e=325.3 (M+H)$^+$.

Example 125

2'-Chloro-3,6-dimethyl-[4,4']bipyridinyl-2-carboxylic acid (1-methyl-1H-pyrazol-3-yl)-amide The title compound, was prepared from 4-Bromo-3,6-dimethyl-pyridine-2-carboxylic acid (1-methyl-1H-pyrazol-3-yl)-amide in accordance with the general method of example 1, step 6; using 2-Chloropyridine-4-boronic acid to yield the final compound as a light brown solid, MS (ISP): m/e=342.1, 344.2 (M+H)$^+$.

Example 126

4-(3,5-Difluorophenyl)-3,6-dimethyl-pyridine-2-carboxylic acid (2-methyl-pyridin-4-yl)-amide The title compound, was prepared from 4-Bromo-3,6-dimethyl-pyridine-2-carboxylic acid (2-methyl-pyridin-4-yl)-amide (from ester, Analog, Ex 99) in accordance with the general method of example 1, step 6; using 3-5-Difluoroboronic acid to yield the final compound as a off-white solid, MS (ISP): m/e=354.2 (M+H)$^+$.

Example 127

5-Fluoro-3',6'-dimethyl-[3,4']bipyridinyl-2'-carboxylic acid (2-methyl-pyridin-4-yl)-amide The title compound, was prepared from 4-Bromo-3,6-dimethyl-pyridine-2-carboxylic acid (2-methyl-pyridin-4-yl)-amide in accordance with the general method of example 1, step 6; using 5-Fluoropyridine-3-boronic acid to yield the final compound as a white solid, MS (ISP): m/e=337.3 (M+H)$^+$.

Example 128

3',6'-Dimethyl-[3,4']bipyridinyl-2'-carboxylic acid (2-methyl-pyridin-4-yl)-amide The title compound, was prepared from 4-Bromo-3,6-dimethyl-pyridine-2-carboxylic acid (2-methyl-pyridin-4-yl)-amide in accordance with the general method of example 1, step 6; using 3-Pyridineboronic acid to yield the final compound as a off-white solid, MS (ISP): m/e=319.2 (M+H)$^+$.

Example 129

4-(3-Chloro-4-fluoro-phenyl)-3,6-dimethyl-pyridine-2-carboxylic acid (2-methyl-pyridin-4-yl)-amide The title compound, was prepared from 4-Bromo-3,6-dimethyl-pyridine-2-carboxylic acid (2-methyl-pyridin-4-yl)-amide in accordance with the general method of example 1, step 6; using 3-Chloro-4-fluorophenylboronic acid to yield the final compound as a white solid, MS (ISP): m/e=370.1, 372.2 (M+H)$^+$.

Example 130

4-(3,5-Difluorophenyl)-3,6-dimethyl-pyridine-2-carboxylic acid (2-chloro-pyridin-4-yl)-amide The title compound, was prepared from 4-Bromo-3,6-dimethyl-pyridine-2-carboxylic acid (2-chloro-pyridin-4-yl)-amide (from ester, Analog, Ex 99) in accordance with the general method of example 1, step 6; using 3-5-Difluoroboronic acid to yield the final compound as a white solid, MS (ISP): m/e=374.1, 376.2 (M+H)$^+$.

Example 131

6'-Methyl-5-trifluoromethyl-[3,4']bipyridinyl-2'-carboxylic acid (4-methyl-thiazol-2-yl)-amide Step 1: 6-Methyl-4-(4,4,5,5-tetramethyl-[1,3,2]dioxaborolan-2-yl)-pyridine-2-carboxylic acid (4-methyl-thiazol-2-yl)-amide To a solution of 610 mg of 4-Bromo-6-methyl-pyridine-2-carboxylic acid (4-methyl-thiazol-2-yl)-amide in 20 ml of dioxane were added 576 mg of potassium acetate and 68.5 mg of Dichloro-bis(triphenylphosphine)palladium. After stirring for 5 min under an Argon atmosphere, 596 mg of Bis(pinacolato)diboron were added and the reaction was stirred for 36 h at 101° C. The mixture was allowed to cool to room temperature, extracted with ethyl acetate/water, and dried over magnesium sulfate. After concentration, the crude orange solid was dissolved in a minimal amount of methylene chloride to which diisopropyl ether was added and allowed to crystallize at 0° C. One obtains 413 mg of the title compound as a light yellow solid, MS (ISP): m/e=360.2 (M+H)$^+$.

Step 2: 6'-Methyl-5-trifluoromethyl-[3,4']bipyridinyl-2'-carboxylic acid (4-methyl-thiazol-2-yl)-amide The title compound, was prepared from 3-Trifluoromethyl-5-bromopyridine and 6-Methyl-4-(4,4,5,5-tetramethyl-[1,3,2]dioxa-borolan-2-yl)-pyridine-2-carboxylic acid (4-methyl-thiazol-2-yl)-amide in accordance with the general method of example 1, step 6 to yield the final compound as a white solid, MS (ISP): m/e=379.2 (M+H)$^+$.

Example 132

2'-Fluoro-6-methyl-[4,4']bipyridinyl-2-carboxylic acid (4-methyl-thiazol-2-yl)-amide The title compound, was prepared from 6-Methyl-4-(4,4,5,5-tetramethyl-[1,3,2]dioxaborolan-2-yl)-pyridine-2-carboxylic acid (4-methyl-thiazol-2-yl)-amide in accordance with the general method of example 131, step 2 using 2-Fluoro-4-bromopyridine instead of 3-Trifluoromethyl-5-bromopyridine to yield the final compound as a white solid, MS (ISP): m/e=329.1 (M+H)$^+$.

Example 133

6-Methyl-4-pyrazin-2-yl-pyridine-2-carboxylic acid (4-methyl-thiazol-2-yl)-amide The title compound, was prepared from 6-Methyl-4-(4,4,5,5-tetramethyl-[1,3,2]dioxaborolan-2-yl)-pyridine-2-carboxylic acid (4-methyl-thiazol-2-yl)-amide in accordance with the general method of example 131, step 2 using 2-iodopyrazine instead of 3-Trifluoromethyl-5-bromopyridine to yield the final compound as a white solid, MS (ISP): m/e=312.1 (M+H)$^+$.

Example 134

2,6'-Dimethyl-[3,4']bipyridinyl-2'-carboxylic acid (4-methyl-thiazol-2-yl)-amide The title compound, was prepared from 6-Methyl-4-(4,4,5,5-tetramethyl-[1,3,2]dioxa-borolan-2-yl)-pyridine-2-carboxylic acid (4-methyl-thiazol-2-yl)-amide in accordance with the general method of example 131, step 2 using 3-Bromo-2-methylpyridine instead of 3-Trifluoromethyl-5-bromopyridine to yield the final compound as a white solid, MS (ISP): m/e=325.2 (M+H)+.

Example 135

6,2'-Dimethyl-[4,4']bipyridinyl-2-carboxylic acid (4-methyl-thiazol-2-yl)-amide

The title compound, was prepared from 6-Methyl-4-(4,4,5,5-tetramethyl-[1,3,2]dioxaborolan-2-yl)-pyridine-2-carboxylic acid (4-methyl-thiazol-2-yl)-amide in accordance with the general method of example 131, step 2 using 4-Iodo-2-methyl-pyridine instead of 3-Trifluoromethyl-5-bromopyridine to yield the final compound as a white solid, MS (ISP): m/e=325.2 (M+H)+.

Example 136

6-Methyl-2-trifluoromethyl-[4,4]bipyridinyl-2-carboxylic acid (4-methyl-thiazol-2-yl)-amide The title compound, was prepared from 6-Methyl-4-(4,4,5,5-tetramethyl-[1,3,2]dioxaborolan-2-yl)-pyridine-2-carboxylic acid (4-methyl-thiazol-2-yl)-amide in accordance with the general method of example 131, step 2 using 4-Bromo-2-trifluoromethyl-pyridine instead of 3-Trifluoromethyl-5-bromopyridine to yield the final compound as a yellow oil, MS (ISP): m/e=379.2 (M+H)+.

Example 137

2'-Cyano-6-methyl-[4,4']bipyridinyl-2-carboxylic acid (4-methyl-thiazol-2-yl)-amide The title compound, was prepared from 6-Methyl-4-(4,4,5,5-tetramethyl-[1,3,2]dioxaborolan-2-yl)-pyridine-2-carboxylic acid (4-methyl-thiazol-2-yl)-amide in accordance with the general method of example 131, step 2 using 4-Bromo-2-cyanopyridine instead of 3-Trifluoromethyl-5-bromopyridine to yield the final compound as a off-white solid, MS (ISP): m/e=336.3 (M+H)+.

Example 138

6'-Cyano-6,2'-dimethyl-[4,4']bipyridinyl-2-carboxylic acid (4-methyl-thiazol-2-yl)-amide The title compound, was prepared from 6-Methyl-4-(4,4,5,5-tetramethyl-[1,3,2]dioxa-borolan-2-yl)-pyridine-2-carboxylic acid (4-methyl-thiazol-2-yl)-amide in accordance with the general method of example 131, step 2 using 4-Bromo-6-methyl-pyridine-2-carbonitrile instead of 3-Trifluoromethyl-5-bromopyridine to yield the final compound as a yellow solid, MS (ISP): m/e=350.3 (M+H)+.

Example 139

2'-Chloro-5'-fluoro-6-methyl-[4,4']bipyridinyl-2-carboxylic acid (4-methyl-thiazol-2-yl)-amide The title compound, was prepared from 6-Methyl-4-(4,4,5,5-tetramethyl-[1,3,2]dioxaborolan-2-yl)-pyridine-2-carboxylic acid (4-methyl-thiazol-2-yl)-amide in accordance with the general method of example 131, step 2 using 2-Chloro-5-fluoro-4-iodopyridine instead of 3-Trifluoromethyl-5-bromopyridine to yield the final compound as a off-white solid, MS (ISP): m/e=363.2, 365.1 (M+H)+.

Example 140

5,6'-Dimethyl-[3,4']bipyridinyl-2'-carboxylic acid (4-methyl-thiazol-2-yl)-amide The title compound, was prepared from 6-Methyl-4-(4,4,5,5-tetramethyl-[1,3,2]dioxaborolan-2-yl)-pyridine-2-carboxylic acid (4-methyl-thiazol-2-yl)-amide in accordance with the general method of example 131, step 2 using 5-Bromo-3-picolin instead of 3-Trifluoromethyl-5-bromopyridine to yield the final compound as a white solid, MS (ISP): m/e=325.3 (M+H)+.

Example 141

2'-Fluoro-6-methyl-[4,4']bipyridinyl-2-carboxylic acid (2-methyl-thiazol-4-yl)-amide Step 1: 6-Methyl-4-(4,4,5,5-tetramethyl-[1,3,2]dioxaborolan-2-yl)-pyridine-2-carboxylic acid (2-methyl-thiazol-4-yl)-amide The title compound, was prepared in accordance with the general method of example 131, step 1 from 4-Bromo-6-methyl-pyridine-2-carboxylic acid (2-methyl-thiazol-4-yl)-amide and Bis(pinacolato)diboron to yield the desired intermediate as a light yellow crystalline solid, MS (ISP): m/e=278.1 [M(B(OH)$_2$)+H]+.

Step 2: 2'-Cyano-6-methyl-[4,4']bipyridinyl-2-carboxylic acid (2-methyl-thiazol-4-yl)-amide The title compound, was prepared from 6-Methyl-4-(4,4,5,5-tetramethyl-[1,3,2]dioxaborolan-2-yl)-pyridine-2-carboxylic acid (2-methyl-thiazol-4-yl)-amide in accordance with the general method of example 131, step 2 using 2-Bromo-5-fluoropyridine instead of 3-Trifluoromethyl-5-bromopyridine to yield the final compound as a white crystalline, MS (ISP): m/e=329.2 (M+H)+.

Example 142

2'-Cyano-6-methyl-[4,4']bipyridinyl-2-carboxylic acid (2-methyl-pyridin-4-yl)-amide Step 1: 6-Methyl-4-(4,4,5,5-tetramethyl-[1,3,2]dioxaborolan-2-yl)-pyridine-2-carboxylic acid (2-methyl-pyridin-4-yl)-amide The title compound, was prepared in accordance with the general method of example 131, step 1 from 4-Bromo-6-methyl-pyridine-2-carboxylic acid (2-methyl-pyridin-4-yl)-amide and Bis(pinacolato)diboron to yield the desired intermediate as an off-white solid, MS (ISP): m/e=272.3 [M(B(OH)$_2$)+H]+.

Step 2: 2'-Cyano-6-methyl-[4,4']bipyridinyl-2-carboxylic acid (2-methyl-pyridin-4-yl)-amide The title compound, was prepared from 6-Methyl-4-(4,4,5,5-tetramethyl-[1,3,2]dioxaborolan-2-yl)-pyridine-2-carboxylic acid (2-methyl-pyridin-4-yl)-amide in accordance with the general method of example 131, step 2 using 4-Bromo-2-cyanopyridine instead of 3-Trifluoromethyl-5-bromopyridine to yield the final compound as a white solid, MS (ISP): m/e=330.2 (M+H)$^+$.

Example 143

6'-Cyano-6,2'-dimethyl-[4,4']bipyridinyl-2-carboxylic acid (2-methyl-pyridin-4-yl)-amide The title compound, was prepared from 6-Methyl-4-(4,4,5,5-tetramethyl-[1,3,2]dioxaborolan-2-yl)-pyridine-2-carboxylic acid (2-methyl-pyridin-4-yl)-amide in accordance with the general method of example 131, step 2 using 4-Bromo-6-methyl-pyridine-2-carbonitrile instead of 3-Trifluoromethyl-5-bromopyridine to yield the final compound as a off-white solid, MS (ISP): m/e=344.2 (M+H)$^+$.

Example 144

6,2'-Dimethyl-[4,4']bipyridinyl-2-carboxylic acid (2-methyl-pyridin-4-yl)-amide

The title compound, was prepared from 6-Methyl-4-(4,4,5,5-tetramethyl-[1,3,2]dioxaborolan-2-yl)-pyridine-2-carboxylic acid (2-methyl-pyridin-4-yl)-amide in accordance with the general method of example 131, step 2 using 4-Bromo-2-methylpyridine instead of 3-Trifluoromethyl-5-bromopyridine to yield the final compound as a colorless amorphous, MS (ISP): m/e=319.2 (M+H)$^+$.

Example 145

2'-Chloro-6-methyl-[4,4']bipyridinyl-2-carboxylic acid (2-methyl-pyridin-4-yl)-amide The title compound, was prepared from 6-Methyl-4-(4,4,5,5-tetramethyl-[1,3,2]dioxaborolan-2-yl)-pyridine-2-carboxylic acid (2-methyl-pyridin-4-yl)-amide in accordance with the general method of example 131, step 2 using 2-Chloro-4-bromopyridine instead of 3-Trifluoromethyl-5-bromopyridine to yield the final compound as a white amorphous, MS (ISP): m/e=339.1, 341.1 (M+H)$^+$.

Example 146

6'-Cyano-6,2'-dimethyl-[4,4']bipyridinyl-2-carboxylic acid (2-chloro-pyridin-4-yl)-amide Step 1: 6-Methyl-4-(4,4,5,5-tetramethyl-[1,3,2]dioxaborolan-2-yl)-pyridine-2-carboxylic acid (2-chloro-pyridin-4-yl)-amide The title compound, was prepared in accordance with the general method of example 131, step 1 from 4-Bromo-6-methyl-pyridine-2-carboxylic acid (2-choro-pyridin-4-yl)-amide and Bis(pinacolato)diboron to yield the desired intermediate as a light brown solid, MS (ISP): m/e=292.1, 294.1 [M(B(OH)$_2$)+H]$^+$.

Step 2: 2'-Cyano-6-methyl-[4,4']bipyridinyl-2-carboxylic acid (2-methyl-pyridin-4-yl)-amide The title compound, was prepared from 6-Methyl-4-(4,4,5,5-tetramethyl-[1,3,2]dioxa-borolan-2-yl)-pyridine-2-carboxylic acid (2-chloro-pyridin-4-yl)-amide in accordance with the general method of example 131, step 2 using 4-Bromo-2-cyanopyridine instead of 3-Trifluoromethyl-5-bromopyridine to yield the final compound as a white solid, MS (ISP): m/e=364.1 (M+H)$^+$.

Example 147

2'-Cyano-6-methyl-[4,4']bipyridinyl-2-carboxylic acid (2-chloro-pyridin-4-yl)-amide The title compound, was prepared from 6-Methyl-4-(4,4,5,5-tetramethyl-[1,3,2]dioxaborolan-2-yl)-pyridine-2-carboxylic acid (2-chloro-pyridin-4-yl)-amide in accordance with the general method of example 131, step 2 using 4-Bromo-2-cyanopyridine instead of 3-Trifluoromethyl-5-bromopyridine to yield the final compound as a white solid, MS (ISP): m/e=350.2, 352.2 (M+H)$^+$.

Example 148

6,2'-Dimethyl-[4,4']bipyridinyl-2-carboxylic acid (2-chloro-pyridin-4-yl)-amide

The title compound, was prepared from 6-Methyl-4-(4,4,5,5-tetramethyl-[1,3,2]dioxaborolan-2-yl)-pyridine-2-carboxylic acid (2-chloro-pyridin-4-yl)-amide in accordance with the general method of example 131, step 2 using 4-Bromo-2-methylpyridine instead of 3-Trifluoromethyl-5-bromopyridine to yield the final compound as a white solid, MS (ISP): m/e=339.1, 341.1 (M+H)$^+$.

Example 149

6,2',6'-Trimethyl-[4,4']bipyridinyl-2-carboxylic acid (2-chloro-pyridin-4-yl)-amide The title compound, was prepared from 6-Methyl-4-(4,4,5,5-tetramethyl-[1,3,2]dioxaborolan-2-yl)-pyridine-2-carboxylic acid (2-chloro-pyridin-4-yl)-amide in accordance with the general method of example 131, step 2 using 4-Bromo-2,6-dimethylpyridine instead of 3-Trifluoromethyl-5-bromopyridine to yield the final compound as a white solid, MS (ISP): m/e=353.2, 355.1 (M+H)$^+$.

Example 150

5,6'-Dimethyl-[3,4']bipyridinyl-2'-carboxylic acid (2-chloro-pyridin-4-yl)-amide The title compound, was prepared from 6-Methyl-4-(4,4,5,5-tetramethyl-[1,3,2]dioxaborolan-2-yl)-pyridine-2-carboxylic acid (2-chloro-pyridin-4-yl)-amide in accordance with the general method of example 131, step 2 using 3-Bromo-5-methylpyridine instead of 3-Trifluoromethyl-5-bromopyridine to yield the final compound as a white solid, MS (ISP): m/e=339.1, 341.1 (M+H)$^+$.

Example 151

2'-Chloro-6-methyl-[4,4']bipyridinyl-2-carboxylic acid (2-chloro-pyridin-4-yl)-amide The title compound, was prepared from 6-Methyl-4-(4,4,5,5-tetramethyl-[1,3,2]dioxaborolan-2-yl)-pyridine-2-carboxylic acid (2-chloro-pyridin-4-yl)-amide in accordance with the general method of example 131, step 2 using 4-Bromo-2-chloropyridine instead of 3-Trifluoromethyl-5- bromopyridine to yield the final compound as a white solid, MS (ISP): m/e=359.1, 361.1 (M+H)$^+$.

Example 152

6,2',5'-Trimethyl-[4,4']bipyridinyl-2-carboxylic acid (2-chloro-pyridin-4-yl)-amide The title compound, was prepared from 6-Methyl-4-(4,4,5,5-tetramethyl-[1,3,2]dioxaborolan-2-yl)-pyridine-2-carboxylic acid (2-chloro-pyridin-4-yl)-amide in accordance with the general method of example 131, step 2 using RO4509094-000-001 instead of 3-Trifluoromethyl-5-bromopyridine to yield the final compound as a white solid, MS (ISP): m/e=353.2, 355.1 (M+H)$^+$.

Example 153

2'-Chloro-6-methyl-[4,4']bipyridinyl-2-carboxylic acid (1-methyl-1H-pyrazol-3-yl)-amide Step 1: 6-Methyl-4-(4,4,5,5-tetramethyl-[1,3,2]dioxaborolan-2-yl)-pyridine-2-carboxylic acid (1-methyl-1H-pyrazol-3-yl)-amide The title compound, was prepared in accordance with the general method of example 131, step 1 from 4-Bromo-6-methyl-pyridine-2-carboxylic acid (1-methyl-1H-pyrazol-3-yl)-amide and Bis(pinacolato)diboron to yield the desired intermediate as an off-white solid, MS (ISP): m/e=261.2 [M(B(OH)$_2$)+H]$^+$.

Step 2: 2'-Cyano-6-methyl-[4,4']bipyridinyl-2-carboxylic acid (1-methyl-1H-pyrazol-3-yl)-amide The title compound, was prepared from 6-Methyl-4-(4,4,5,5-tetramethyl-[1,3,2]dioxaborolan-2-yl)-pyridine-2-carboxylic acid (1-methyl-1H-pyrazol-3-yl)-amide in accordance with the general method of example 131, step 2 using 4-Bromo-2-chloropyridine instead of 3-Trifluoromethyl-5-bromopyridine to yield the final compound as a white solid, MS (ISP): m/e=328.2, 330.2 (M+H)$^+$.

Example 154

6,2'-Dimethyl-[4,4']bipyridinyl-2-carboxylic acid (1-methyl-1H-pyrazol-3-yl)-amide The title compound, was prepared from 6-Methyl-4-(4,4,5,5-tetramethyl-[1,3,2]dioxaborolan-2-yl)-pyridine-2-carboxylic acid (1-methyl-1H-pyrazol-3-yl)-amide in accordance with the general method of example 131, step 2 using 4-Bromo-2-methylpyridine instead of 3-Trifluoromethyl-5-bromopyridine to yield the final compound as a white amorphous, MS (ISP): m/e=308.4 (M+H)$^+$.

Example 155

6,2',6'-Trimethyl-[4,4']bipyridinyl-2-carboxylic acid (1-methyl-1H-pyrazol-3-yl)-amide The title compound, was prepared from 6-Methyl-4-(4,4,5,5-tetramethyl-[1,3,2]dioxaborolan-2-yl)-pyridine-2-carboxylic acid (1-methyl-1H-pyrazol-3-yl)-amide in accordance with the general method of example 131, step 2 using RO4477367-000-001 instead of 3-Trifluoromethyl-5-bromopyridine to yield the final compound as a white solid, MS (ISP): m/e=322.3 (M+H)$^+$.

Example 156

2'-Chloro-5'-fluoro-6-methyl-[4,4']bipyridinyl-2-carboxylic acid (1-methyl-1H-pyrazol-3-yl)-amide The title compound, was prepared from 6-Methyl-4-(4,4,5,5-tetramethyl-[1,3,2]dioxaborolan-2-yl)-pyridine-2-carboxylic acid (1-methyl-1H-pyrazol-3-yl)-amide in accordance with the general method of example 131, step 2 using 2-Chloro-5-fluoro-4-iodpyridine instead of 3-Trifluoromethyl-5-bromopyridine to yield the final compound as a white solid, MS (ISP): m/e=346.1, 348.2 (M+H)$^+$.

Example 157

5,6'-Dimethyl-[3,4']bipyridinyl-2'-carboxylic acid (1-methyl-1H-pyrazol-3-yl)-amide The title compound, was prepared from 6-Methyl-4-(4,4,5,5-tetramethyl-[1,3,2]dioxaborolan-2-yl)-pyridine-2-carboxylic acid (1-methyl-1H-pyrazol-3-yl)-amide in accordance with the general method of example 131, step 2 using 5-Bromo-3-picolin instead of 3-Trifluoromethyl-5-bromopyridine to yield the final compound as a white solid, MS (ISP): m/e=308.3 (M+H)$^+$.

Example 158

6,2',5'-Trimethyl-[4,4']bipyridinyl-2-carboxylic acid (1-methyl-1H-pyrazol-3-yl)-amide The title compound, was prepared from 6-Methyl-4-(4,4,5,5-tetramethyl-[1,3,2]dioxaborolan-2-yl)-pyridine-2-carboxylic acid (1-methyl-1H-pyrazol-3-yl)-amide in accordance with the general method of example 131, step 2 using RO4509094-000-001 instead of 3-Trifluoromethyl-5-bromopyridine to yield the final compound as a white amorphous, MS (ISP): m/e=322.3 (M+H)$^+$.

Example 159

6'-Cyano-6,2'-dimethyl-[4,4']bipyridinyl-2-carboxylic acid (1-methyl-1H-pyrazol-3-yl)-amide The title compound, was prepared from 6-Methyl-4-(4,4,5,5-tetramethyl-[1,3,2]dioxaborolan-2-yl)-pyridine-2-carboxylic acid (1-methyl-1H-pyrazol-3-yl)-amide in accordance with the general method of example 131, step 2 using 34869B0741M instead of 3-Trifluoromethyl-5-bromopyridine to yield the final compound as a white solid, MS (ISP): m/e=333.2 (M+H)$^+$.

Example 160

2'-Cyano-6-methyl-[4,4']bipyridinyl-2-carboxylic acid (1-methyl-1H-pyrazol-3-yl)-amide The title compound, was prepared from 6-Methyl-4-(4,4,5,5-tetramethyl-[1,3,2]dioxaborolan-2-yl)-pyridine-2-carboxylic acid (1-methyl-1H-pyrazol-3-yl)-amide in accordance with the general method of example 131, step 2 using 4-Bromo-2-cyanopyridine instead of 3-Trifluoromethyl-5- bromopyridine to yield the final compound as a white solid, MS (ISP): m/e=319.2 (M+H)+.

Example 161

4-(3,5-Difluorophenyl)-6-methyl-pyridine-2-carboxylic acid (5-cyano-pyridin-2-yl)-amide Step 1: 4-(3,5-Difluorophenyl)-6-methyl-pyridine-2-carboxylic acid ethyl ester The title compound, was prepared from 4-Bromo-6-methyl-pyridine-2-carboxylic acid ethyl ester (example 1, step 4) in accordance with the general method of example 1, step 6 using 3,5-Difluorophenylboronic acid instead of 3-Fluorophenylboronic acid to yield the final compound as a white crystalline solid, MS (ISP): m/e=278.1 (M+H)+.

Step 2: 4-(3,5-Difluorophenyl)-6-methyl-pyridine-2-carboxylic acid (5-cyano-pyridin-2-yl)-amide The title compound, was prepared from 4-(3,5-Difluorophenyl)-6-methyl-pyridine-2-carboxylic acid ethyl ester in accordance with the general method of example 26, step 6 using 2-Amino-4-cyanopyridine instead of 3-chloroaniline to yield the final compound as a white crystalline, MS (ISP): m/e=351.3 (M+H)+.

Example 162

4-(3,5-Difluorophenyl)-6-methyl-pyridine-2-carboxylic acid (5-methyl-pyridin-2-yl)-amide The title compound, was prepared from 4-(3,5-Difluorophenyl)-6-methyl-pyridine-2-carboxylic acid ethyl ester in accordance with the general method of example 26, step 6 using 2-Amino-5-methylpyridine instead of 3-chloroaniline to yield the final compound as a white crystalline, MS (ISP): m/e=340.2 (M+H)+.

Example 163

4-(3,5-Difluorophenyl)-6-methyl-pyridine-2-carboxylic acid (4-cyanomethyl-thiazol-2-yl)-amide Step 1: 2-(2-Amino-thiazol-4-yl)-acetamide A solution of 2.5 g (15.0 mmol) (2-Amino-thiazol-4-yl)-acetic acid ethyl ester in 70 ml of 7N ammonia solution in methanol was stirred for 6 days at room temperature. After concentration in vacuo, one obtains 2.0 g (95%) of the title compound as a light brown solid, which was directly used in the next step without further purification.

Step 2: (2-Amino-thiazol-4-yl)-acetonitrile

To a solution of 2.0 g (13.0 mmol) of 2-(2-Amino-thiazol-4-yl)-acetamide in 30 ml of dry DMF was added Phosphorus oxychloride (2.3 ml, 25.0 mmol, 2.0 equiv.) dropwise at 0° C.
After stirring for 5 min at 0° C., the mixture was allowed to warm up to room temperature and stirred for 1 h, and then for 15 min at 80° C. After workup (1 N HCl, sat. Na$_2$CO$_3$ solution, Ethyl acetate, H$_2$O), drying and concentration in vacuo, the crude material was purified by chromatography on silica-gel with ethyl acetate/heptane 1:9 as eluant to yield the title compound as a light yellow solid.

Step 3: 4-(3,5-Difluorophenyl)-6-methyl-pyridine-2-carboxylic acid (4-cyanomethyl-thiazol-2-yl)-amide The title compound, was prepared from 4-(3,5-Difluorophenyl)-6-methyl-pyridine-2-carboxylic acid ethyl ester in accordance with the general method of example 26, step 6 using (2-Amino-thiazol-4-yl)-acetonitrile instead of 3-chloroaniline to yield the final compound as a off-white solid, MS (ISP): m/e=371.2 (M+H)+.

Example 164

4-(3,5-Difluorophenyl)-6-methyl-pyridine-2-carboxylic acid (4-difluoromethyl-thiazol-2-yl)-amide The title compound, was prepared from 4-(3,5-Difluorophenyl)-6-methyl-pyridine-2-carboxylic acid ethyl ester in accordance with the general method of example 26, step 6 using 4-Difluoromethyl-thiazol-2-ylamine instead of 3-chloroaniline to yield the final compound as a white solid, MS (ISP): m/e=382 [M]+.

Example 165

4-(3,5-Difluorophenyl)-6-methyl-pyridine-2-carboxylic acid (4-cyano-thiazol-2-yl)-amide The title compound, was prepared from 4-(3,5-Difluorophenyl)-6-methyl-pyridine-2-carboxylic acid ethyl ester in accordance with the general method of example 26, step 6 using 2-Amino-4-thiazolecarbonitrile instead of 3-chloroaniline to yield the final compound as a off-white solid, MS (ISP): m/e=356.9 (M+H)+.

Example 166

4-(3,5-Difluorophenyl)-6-methyl-pyridine-2-carboxylic acid (4-methoxymethyl-thiazol-2-yl)-amide The title compound, was prepared from 4-(3,5-Difluorophenyl)-6-methyl-pyridine-2-carboxylic acid ethyl ester in accordance with the general method of example 26, step 6 using 4-Methoxymethyl-thiazol-2-ylamine (CAS: [640768-40-7]) instead of 3-chloro-aniline to yield the final compound as a light brown solid, MS (ISP): m/e=376.3 (M+H)+.

Example 167

4-(3,5-Difluorophenyl)-6-methyl-pyridine-2-carboxylic acid (4-chloro-pyrimidin-2-yl)-amide The title compound, was prepared from 4-(3,5-Difluorophenyl)-6-methyl-pyridine-2-carboxylic acid ethyl ester in accordance with the general method of example 26, step 6 using 4-Chloro-pyrimidin-2-ylamine instead of 3-chloroaniline to yield the final compound as a light brown solid, MS (ISP): m/e=361.1, 363.2 (M+H)+.

Example 168

4-(3,5-Difluorophenyl)-6-methyl-pyridine-2-carboxylic acid (2-chloro-pyrimidin-4-yl)-amide The title compound, was prepared from 4-(3,5-Difluorophenyl)-6-methyl-pyridine-2-carboxylic acid ethyl ester in accordance with the general method of example 26, step 6 using 4-Chloro-pyrimidin-2-ylamine instead of 3-chloroaniline to yield the final compound as a white solid, MS (ISP): m/e=361.0, 363.2 (M+H)+.

Example 169

4-(3,5-Difluorophenyl)-6-methyl-pyridine-2-carboxylic acid (2-cyano-pyridin-4-yl)-amide The title compound, was prepared from 4-(3,5-Difluorophenyl)-6-methyl-pyridine-2-carboxylic acid ethyl ester in accordance with the general method of example 26, step 6 using 4-Amino-pyridine-2-carbonitrile instead of 3-chloroaniline to yield the final compound as a white crystalline, MS (ISP): m/e=351.2 (M+H)+.

Example 170

(3-{[4-(3,5-Difluorophenyl)-6-methyl-pyridine-2-carbonyl]-amino}-pyrazol-1-yl)-acetic acid ethyl ester The title compound, was prepared from 4-(3,5-Difluorophenyl)-6-methyl-pyridine-2-carboxylic acid ethyl ester in accordance with the general method of example 26, step 6 using Ethyl (3-Amino-1-pyrazolyl)acetate instead of 3-chloroaniline to yield the final compound as a white crystalline, MS (ISP): m/e=401.2 (M+H)+.

Example 171

4-(3,5-Difluorophenyl)-6-methyl-pyridine-2-carboxylic acid [1-(2,2,2-trifluoro-ethyl)-1H-pyrazol-3-yl]-amide The title compound, was prepared from 4-(3,5-Difluorophenyl)-6-methyl-pyridine-2-carboxylic acid ethyl ester in accordance with the general method of example 26, step 6 using 3-Amino-1-(2-trifluoroethyl)pyrazole instead of 3-chloroaniline to yield the final compound as a off-white crystalline, MS (ISP): m/e=397.2 (M+H)+.

Example 172

6-Methyl-4-pyrimidin-5-yl-pyridine-2-carboxylic acid (1-methyl-1H-pyrazol-3-yl)-amide Step 1:
6-Methyl-4-pyrimidin-5-yl-pyridine-2-carboxylic acid ethyl ester The title compound, was prepared from 4-Bromo-6-methyl-pyridine-2-carboxylic acid ethyl ester (example 1, step 4) and 5-Pyrimidineboronic acid in accordance with the general method of example 1, step 6 to yield the final compound as a white solid, MS (ISP): m/e=244.3 (M+H)+.

Step 2: 6-Methyl-4-pyrimidin-5-yl-pyridine-2-carboxylic acid (1-methyl-1H-pyrazol-3-yl)-amide The title compound, was prepared from 6-Methyl-4-pyrimidin-5-yl-pyridine-2-carboxylic acid ethyl ester in accordance with the general method of example 26, step 6 using 3-Amino-1-methylpyrazole instead of 3-chloroaniline to yield the final compound as a gray crystalline, MS (ISP): m/e=295.2 (M+H)+.

Example 173

5-Fluoro-6'-methyl-[3,4']bipyridinyl-2'-carboxylic acid (5-chloro-pyridin-2-yl)-amide Step 1: 5-Fluoro-6'-methyl-[3,4']bipyridinyl-2'-carboxylic acid ethyl ester The title compound, was prepared from 4-Bromo-6-methyl-pyridine-2-carboxylic acid ethyl ester (example 1, step 4) and 5-Fluoropyridine-3-boronic acid in accordance with the general method of example 1, step 6 to yield the final compound as a light yellow oil, MS (ISP): m/e=261.2 (M+H)+.

Step 2: 5-Fluoro-6'-methyl-[3,4']bipyridinyl-2'-carboxylic acid (5-chloro-pyridin-2-yl)-amide The title compound, was prepared from 5-Fluoro-6'-methyl-[3,4']bipyridinyl-2'-carboxylic acid ethyl ester in accordance with the general method of example 26, step 6 using 2-Amino-5-chloropyridine instead of 3-chloroaniline to yield the final compound as a white solid, MS (ISP): m/e=343.1, 345.0 (M+H)+.

Example 174

5-Fluoro-6'-methyl-[3,4']bipyridinyl-2'-carboxylic acid (4-difluoromethyl-thiazol-2-yl)-amide The title compound, was prepared from 5-Fluoro-6'-methyl-[3,4']bipyridinyl-2'-carboxylic acid ethyl ester in accordance with the general method of example 26, step 6 using RO5027431-000-001 instead of 3-chloroaniline to yield the final compound as a white solid, MS (ISP): m/e=365 (M+H)+.

Example 175

5-Fluoro-6'-methyl-[3,4']bipyridinyl-2'-carboxylic acid (4-cyano-thiazol-2-yl)-amide The title compound, was prepared from 5-Fluoro-6'-methyl-[3,4']bipyridinyl-2'-carboxylic acid ethyl ester in accordance with the general method of example 26, step 6 using RO0199885-000-001 instead of 3-chloroaniline to yield the final compound as a light yellow crystalline, MS (ISP): m/e=340.2 (M+H)+.

Example 176

5-Fluoro-6'-methyl-[3,4']bipyridinyl-2'-carboxylic acid (4-cyclopentyl-thiazol-2-yl)-amide The title compound, was prepared from 5-Fluoro-6'-methyl-[3,4']bipyridinyl-2'-carboxylic acid ethyl ester in accordance with the general method of example 26, step 6 using 4-Cyclopentyl-thiazol-2-ylamine, hydrochloride instead of 3-chloroaniline to yield the final compound as a white solid, MS (ISP): m/e=383 [M]+.

Example 177

5-Fluoro-6'-methyl-[3,4']bipyridinyl-2'-carboxylic acid (3-chloro-phenyl)-amide

The title compound, was prepared from 5-Fluoro-6'-methyl-[3,4']bipyridinyl-2'-carboxylic acid ethyl ester in accordance with the general method of example 26, step 6 using 3-Chloroaniline instead of 3-chloroaniline to yield the final compound as a white solid, MS (ISP): m/e=342.0, 344.1 (M+H)$^+$.

Example 178

5-Fluoro-6'-methyl-[3,4']bipyridinyl-2'-carboxylic acid pyridin-3-ylamide

The title compound, was prepared from 5-Fluoro-6'-methyl-[3,4']bipyridinyl-2'-carboxylic acid ethyl ester in accordance with the general method of example 26, step 6 using 3-Aminopyridine instead of 3-chloroaniline to yield the final compound as a white crystalline, MS (ISP): m/e=309.3 (M+H)$^+$.

Example 179

5-Fluoro-6'-methyl-[3,4']bipyridinyl-2'-carboxylic acid (4-fluoro-phenyl)-amide

The title compound, was prepared from 5-Fluoro-6'-methyl-[3,4']bipyridinyl-2'-carboxylic acid ethyl ester in accordance with the general method of example 26, step 6 using 4-Fluoroaniline instead of 3-chloroaniline to yield the final compound as a gray solid, MS (ISP): m/e=324.9, 326.2 (M+H)$^+$.

Example 180

5-Fluoro-6'-methyl-[3,4']bipyridinyl-2'-carboxylic acid phenylamide

The title compound, was prepared from 5-Fluoro-6'-methyl-[3,4']bipyridinyl-2'-carboxylic acid ethyl ester in accordance with the general method of example 26, step 6 using Aniline instead of 3-chloroaniline to yield the final compound as a white solid, MS (ISP): m/e=308.3, 309.3 (M+H)$^+$.

Example 181

2'-Chloro-6-methyl-[4,4']bipyridinyl-2-carboxylic acid (6-methyl-pyridin-2-yl)-amide Step 1: 2'-Chloro-6-methyl-[4,4']bipyridinyl-2-carboxylic acid ethyl ester The title compound, was prepared from 4-Bromo-6-methyl-pyridine-2-carboxylic acid ethyl ester (example 1, step 4) and 2-Chloropyridine-4-boronic acid in accordance with the general method of example 1, step 6 to yield the final compound as a light yellow oil, MS (ISP): m/e=277.1 (M+H)$^+$.

Step 2: 2'-Chloro-6-methyl-[4,4']bipyridinyl-2-carboxylic acid (6-methyl-pyridin-2-yl)-amide The title compound, was prepared from 2'-Chloro-6-methyl-[4,4']bipyridinyl-2-carboxylic acid ethyl ester in accordance with the general method of example 26, step 6 using 2-amino-6methylpyridine instead of 3-chloroaniline to yield the final compound as a white crystalline, MS (ISP): m/e=339.2, 341.1 (M+H)$^+$.

Example 182

2'-Chloro-6-methyl-[4,4']bipyridinyl-2-carboxylic acid (5-chloro-pyridin-2-yl)-amide The title compound, was prepared from 2'-Chloro-6-methyl-[4,4']bipyridinyl-2-carboxylic acid ethyl ester in accordance with the general method of example 26, step 6 using 2-amino-5chloropyridine instead of 3-chloroaniline to yield the final compound as a white crystalline, MS (ISP): m/e=359.0, 361.1 (M+H)$^+$.

Example 183

2'-Chloro-6-methyl-[4,4']bipyridinyl-2-carboxylic acid (5-methyl-pyridin-2-yl)-amide The title compound, was prepared from 2'-Chloro-6-methyl-[4,4']bipyridinyl-2-carboxylic acid ethyl ester in accordance with the general method of example 26, step 6 using 2-amino-5methylpyridine instead of 3-chloroaniline to yield the final compound as a white crystalline, MS (ISP): m/e=339.2, 341.1 (M+H)$^+$.

Example 184

2'-Chloro-6-methyl-[4,4']bipyridinyl-2-carboxylic acid (2-methyl-pyrimidin-4-yl)-amide The title compound, was prepared from 2'-Chloro-6-methyl-[4,4']bipyridinyl-2-carboxylic acid ethyl ester in accordance with the general method of example 26, step 6 using RO0049272-000-001 instead of 3-chloroaniline to yield the final compound as a white crystalline, MS (ISP): m/e=340.2, 342.0 (M+H)$^+$.

Example 185

6,2'-Dimethyl-[4,4']bipyridinyl-2-carboxylic acid (4-cyano-thiazol-2-yl)-amide

Step 1: 6,2-Dimethyl-[4,4]bipyridinyl-2-carboxylic acid ethyl ester

The title compound, was prepared from 4-Bromo-6-methyl-pyridine-2-carboxylic acid ethyl ester (example 1, step 4) in accordance with the general method of example 1, step 6 using 2-Methyl-4-(4,4,5,5-tetramethyl-[1,3,2]dioxaborolan-2-yl)-pyridine instead of 3-Fluorophenylboronic acid to yield the final compound as a light yellow oil, MS (ISP): m/e=257.3 (M+H)$^+$.

Step 2: 6,2'-Dimethyl-[4,4']bipyridinyl-2-carboxylic acid (4-cyano-thiazol-2-yl)-amide The title compound, was prepared from 6,2-Dimethyl-[4,4]bipyridinyl-2-carboxylic acid ethyl ester in accordance with the general method of example 26, step 6 using 2-Amino-4-thiazolecarbonitrile instead of 3-chloroaniline to yield the final compound as a off-white solid, MS (ISP): m/e=336.3 (M+H)$^+$.

Example 186

6,2'-Dimethyl-[4,4']bipyridinyl-2-carboxylic acid (4-methoxymethyl-thiazol-2-yl)-amide The title compound, was prepared from 6,2-Dimethyl-[4,4]bipyridinyl-2-carboxylic acid ethyl ester in accordance with the general method of example 26, step 6 using 4-Methoxymethyl-thiazol-2-ylamine instead of 3-chloroaniline to yield the final compound as a orange oil, MS (ISP): m/e=355.3 (M+H)+.

Example 187

6,2'-Dimethyl-[4,4']bipyridinyl-2-carboxylic acid (4-methyl-thiazol-2-yl)-amide

The title compound, was prepared from 6,2-Dimethyl-[4,4]bipyridinyl-2-carboxylic acid ethyl ester in accordance with the general method of example 26, step 6 using 2-Amino-4-methylthiazole instead of 3-Chloroaniline to yield the final compound as a light yellow oil, MS (ISP): m/e=325.2 (M+H)+.

Example 188

2-{[4-(3,5-Difluoro-phenyl)-6-methyl-pyridine-2-carbonyl]-amino}-thiazole-4-carboxylic acid methyl ester Step 1: 4-(3,5-Difluorophenyl)-6-methyl-pyrimidine-2-carboxylic acid To solution of 700 mg (2.5 mmol) 4-(3,5-Difluorophenyl)-6-methyl-pyridine-2-carboxylic acid ethyl ester in 15 ml of Methanol were added 10 ml of water and 0.58 ml 32% sodium hydroxide solution. After stirring for 2 h at room temperature, 25 ml of water were added to the reaction, the pH was adjusted to 3 by dropwise addition of 3N HCl solution; and the mixture was stirred for 2 h at room temperature. The precipitate was filtered off, taken up in Ethyl acetate and refiltered. One obtains 550 mg (87%) of the title compound as a crystalline white solid, MS (ISP): m/e=250.2 (M+H)+.

Step 2: 2-{[4-(3,5-Difluoro-phenyl)-6-methyl-pyridine-2-carbonyl]-amino}-thiazole-4-carboxylic acid methyl ester To a solution of 100 mg (0.40 mmol) of 4-(3,5-Difluorophenyl)-6-methyl-pyrimidine-2-carboxylic acid, and 2-Amino-thiazole-4-carboxylic acid methyl ester in 5 ml of dry Dimethylacetamide were added 0.34 ml N-Ethyldiisopropylamine and 141.7 mg (0.44 mmol) of o-(Benzotriazol-1-yl)-1,1,3,3-tetramethyluronium tetrafluoroborate (TBTU). After stirring overnight at room temperature, the mixture was diluted with 15 ml of methylene chloride, and worked up according to standard procedures. The crude material was purified by flash chromatography on silicagel using an Ethyl acetate/Heptane 1:4 mixture as eluant to yield the title compound as a light yellow crystalline solid, MS (ISP): m/e=390.2 (M+H)+.

Example 189

4-(3,5-Difluoro-phenyl)-6-methyl-pyridine-2-carboxylic acid (4-methylcarbamoyl-thiazol-2-yl)-amide The title compound, was prepared from 2-{[4-(3,5-Difluorophenyl)-6-methyl-pyridine-2-carbonyl]-amino}-thiazole-4-carboxylic acid methyl ester in accordance with the general method of example 26, step 6 using ammonium chloride instead of 3-Chloroaniline to yield the final compound as a white crystalline solid, MS (ISP): m/e=389.4 (M+H)+.

Example 190

4-(3,5-Difluoro-phenyl)-6-methyl-pyridine-2-carboxylic acid (1-carbamoylmethyl-1H-pyrazol-3-yl)-amide Step 1: (3-{[4-(3,5-Difluoro-phenyl)-6-methyl-pyridine-2-carbonyl]-amino}-pyrazol-1-yl)-acetic acid ethyl ester The title compound, was prepared from 4-(3,5-Difluorophenyl)-6-methyl-pyrimidine-2-carboxylic acid and (3-Amino-pyrazol-1-yl)-acetic acid ethyl ester (CAS: [895571-89-8]) in accordance with the general method of example 188, step 2 to yield the title compound as a white crystalline solid, MS (ISP): m/e=401.2 (M+H)+.

Step 2: 4-(3,5-Difluoro-phenyl)-6-methyl-pyridine-2-carboxylic acid (1-carbamoylmethyl-1H-pyrazol-3-yl)-amide The title compound, was prepared from in accordance with the general method of example 163, step 1 by ammonolysis of (3-{[4-(3,5-Difluoro-phenyl)-6-methyl-pyridine-2-carbonyl]-amino}-pyrazol-1-yl)-acetic acid ethyl ester to yield the final compound as a white crystalline solid, MS (ISP): m/e=372.2 (M+H)+.

Example 191

4-(3,5-Difluoro-phenyl)-6-methyl-pyridine-2-carboxylic acid (1-cyanomethyl-1H-pyrazol-3-yl)-amide The title compound, was prepared by treatment of 4-(3,5-Difluorophenyl)-6-methyl-pyridine-2-carboxylic acid (1-carbamoylmethyl-1H-pyrazol-3-yl)-amide with POCl₃ in accordance with the general method of example 163, step 2 to yield the final compound as a white solid, MS (ISP): m/e=354.2 (M+H)+.

Example 192

4-(3,5-Difluoro-phenyl)-6-methyl-pyrimidine-2-carboxylic acid (4-methyl-thiazol-2-yl)-amide Step 1: 2-Chloro-4-(3,5-difluoro-phenyl)-6-methyl-pyrimidine A suspension of 1.50 g (9.20 mmol) of 2,4-Dichloro-6-methyl-pyrimidine, 241 mg of Triphenylphosphine, 1.52 g (9.66 mmol) of 3-Fluorophenyl-boronic acid and 5 ml of 2M Na₂CO₃ solution in 20 ml of DME was degassed with a stream of Argon, treated with 103 mg (0.46 mmol) of Palladium(II) acetate and heated to 90° C. for 5 h under Argon in a dosed vessel. The resulting dark red solution was worked up in the usual manner and the crude product was purified by flash chromatography using a gradient of 0-15% Ethyl acetate in hexane as eluant to yield the title compound as a white crystalline solid, MS (ISP): m/e=239.2, 241.3 (M+H)+.

Step 2: 4-(3,5-Difluoro-phenyl)-6-methyl-pyrimidine-2-carbonitrile

To a solution and 13 mg of 1,4-Diazabicyclo[2.2.2]octane (DABCO) in 5 ml of DMSO and 60 mg (1.22 mmol) of sodium cyanide were added 280 mg (1.16 mmol) of 2-Chloro-4-(3,5-difluoro-phenyl)-6-methyl-pyrimidine. After stirring for 3 h at 30-35° C., the mixture was worked according to standard procedures to yield the title compound (142 mg, 53%) as a light yellow crystalline solid, negative-ion MS (ISP): m/e=230.4 [M–H]⁻.

Step 3: 4-(3,5-Difluoro-phenyl)-6-methyl-pyrimidine-2-carboxylic acid methyl ester To 10 ml of a saturated solution of hydrochloric acid in methanol were added 140 mg (0.01 mmol) of 4-(3,5-Difluoro-phenyl)-6-methyl-pyrimidine-2-carbonitrile. The mixture was heated for 5 h at 70° C., and worked up using standard procedures. The crude material, sufficiently pure for the next step, was obtained as a light yellow crystalline solid, MS (ISP): m/e=265.2 (M+H)⁺.

Step 4: 4-(3,5-Difluoro-phenyl)-6-methyl-pyrimidine-2-carboxylic acid (4-methyl-thiazol-2-yl)-amide The title compound, was prepared from 4-(3,5-Difluoro-phenyl)-6-methyl-pyrimidine-2-carboxylic acid methyl ester in accordance with the general method of example 26, step 6, using 2-Amino-4-methylthiazole instead of 3-Chloroaniline to yield the final compound as a white solid, MS (ISP): m/e=347.1 (M+H)⁺.

Example 193

4-(3,5-Difluoro-phenyl)-6-methyl-pyrimidine-2-carboxylic acid (2-methyl-pyrimidin-4-yl)-amide The title compound, was prepared from 4-(3,5-Difluoro-phenyl)-6-methyl-pyrimidine-2-carboxylic acid methyl ester in accordance with the general method of example 26, step 6, using 4-Amino-2-methylpyrimidine instead of 3-Fluorophenylboronic acid to yield the final compound as a off-white crystalline solid, MS (ISP): m/e=342 (M+H)⁺.

Example 194

4-(3,5-Difluoro-phenyl)-6-methyl-pyrimidine-2-carboxylic acid (2-chloro-pyridin-4-yl)-amide The title compound, was prepared from 4-(3,5-Difluoro-phenyl)-6-methyl-pyrimidine-2-carboxylic acid methyl ester in accordance with the general method of example 26, step 6, using 4-Amino-2-chloropyridine instead of 3-Fluorophenylboronic acid to yield the final compound as a white crystalline solid, MS (ISP): m/e=361 (M+H)⁺.

Example 195

4-(3,5-Difluoro-phenyl)-6-methyl-pyrimidine-2-carboxylic acid (2-methyl-pyridin-4-yl)-amide The title compound, was prepared from 4-(3,5-Difluoro-phenyl)-6-methyl-pyrimidine-2-carboxylic acid methyl ester in accordance with the general method of example 26, step 6, using 4-Amino-2-methylpyridine instead of 3-Fluorophenylboronic acid to yield the final compound as a light yellow crystalline solid, MS (ISP): m/e=341.2 (M+H)⁺.

Example 196

4-(3,5-Difluoro-phenyl)-6-methyl-pyrimidine-2-carboxylic acid (2-cyano-pyridin-4-yl)-amide The title compound, was prepared from 4-(3,5-Difluoro-phenyl)-6-methyl-pyrimidine-2-carboxylic acid methyl ester in accordance with the general method of example 26, step 6, using 2-Amino-4-methylthiazole instead of 3-Fluorophenylboronic acid to yield the final compound as a white crystalline solid, MS (ISP): m/e=352.2 (M+H)⁺.

Example 197

4-(3,5-Difluoro-phenyl)-6-methyl-pyrimidine-2-carboxylic acid (2-methyl-thiazol-4-yl)-amide The title compound, was prepared from 4-(3,5-Difluoro-phenyl)-6-methyl-pyrimidine-2-carboxylic acid methyl ester in accordance with the general method of example 26, step 6, using 4-Amino-2-methylthiazole instead of 3-Fluorophenylboronic acid to yield the final compound as a light brown solid, MS (ISP): m/e=347.1 (M+H)⁺.

Example 198

4-(3,5-Difluoro-phenyl)-6-methyl-pyrimidine-2-carboxylic acid (1-methyl-1H-pyrazol-3-yl)-amide The title compound, was prepared from 4-(3,5-Difluoro-phenyl)-6-methyl-pyrimidine-2-carboxylic acid methyl ester in accordance with the general method of example 26, step 6, using 3-Amino-1-methylpyrazole instead of 3-Fluorophenylboronic acid to yield the final compound as a white crystalline solid, MS (ISP): m/e=330.2 (M+H)⁺.

Example 199

4-(3,5-Difluoro-phenyl)-6-methyl-pyridine-2-carboxylic acid (5-fluoro-4-methyl-thiazol-2-yl)-amide

Step 1: (5-Bromo-4-methyl-thiazol-2-yl)-carbamic acid tert-butyl ester

To a solution of 6.46 g (33 mmol) of 5-bromo-4-methyl-thiazol-2-ylamine (CAS [3034-57-9], Kaye & al., J. C. S. Perkin I, 2338 (1981) in 80 ml of dry dichloromethane were added 8.03 g (37 mmol) of di-tert-butyldicarbonate and 0.21 g (2.1 mmol) of 4-dimethylamino-pyridine (DMAP). The reaction was stirred for 20 h at room temperature. After standard workup and purification by flash chromatography (ethyl acetate/heptane 1:2), one obtains the title compound (6.45 g, 64%) as a light brown solid, MS (ISP): m/e=236.9, 238.9 (M+H)⁺.

Step 2: Step 1: (5-Fluoro-4-methyl-thiazol-2-yl)-carbamic acid tert-butyl ester A solution of 6.36 g (22 mmol) of 5-bromo-4-methyl-thiazol-2-yl)-carbamic acid tert-butyl ester in 90 ml of dry THF was cooled to –75° C. Then 41 ml (65 mmol, 3 equiv.) of Butyllithium solution (1.6 M in heptane) were added dropwise maintaining the temperature below –70° C. The yellow suspension was stirred for 30 min. at −75° C. A solution of 9.6 g (30 mmol, 1.4 equiv.) of N-fluorobenzenesulfonimide in 70 ml of dry THF was added dropwise over a period of 35 min. maintaining the temperature below −75° C. After 2 h of stirring at −78° C., the reaction was quenched by addition of 20 ml of saturated ammonium chloride solution. After standard workup and purification by flash chromatography (ethyl acetate/heptane 1:4), one obtains the title compound (3.58 g, 50%) as an off-white semi-solid, MS (ISP): m/e=233.1 $(M+H)^+$.

Step 3: 5-Fluoro-thiazol-2-ylamine

To a solution Of 500 mg (1.5 mmol) of 5-fluoro-4-methyl-thiazol-2-yl)-carbamic acid tert-butyl ester in 10 ml of dichloromethane were added 1.7 ml (15 mmol, 10 equiv.) of trifluoroacetic acid. The orange solution was stirred for 3 h at room temperature. After standard workup, one obtains the crude title compound as a yellow liquid which was directly used in the next step.

Step 4: 4-(3,5-Difluoro-phenyl)-6-methyl-pyridine-2-carboxylic acid (5-fluoro-4-methyl-thiazol-2-yl)-amide The title compound, was prepared from 4-(3,5-Difluoro-phenyl)-6-methyl-pyridine-2-carboxylic acid ethyl ester in accordance with the general method of example 26, step 6 using 5-Fluoro-4-methyl-thiazol-2-ylamine instead of 3-Chloroaniline acid to yield the final compound as an orange solid, MS (ISP): m/e=364.2 $(M+H)^+$.

Example 200

4-(3,5-Difluoro-phenyl)-6-methyl-pyridine-2-carboxylic acid (5-fluoro-thiazol-2-yl)-amide The title compound, was prepared from 4-(3,5-Difluoro-phenyl)-6-methyl-pyridine-2-carboxylic acid ethyl ester in accordance with the general method of example 26, step 6 using 5-Fluoro-thiazol-2-ylamine (CAS: [64588-82-5], WO2006016178 instead of 3-Chloroaniline to yield the final compound as a light yellow crystalline solid, MS (ISP): m/e=350.2 $(M+H)^+$.

Example 201

6,2'-Dimethyl-[4,4']bipyridinyl-2-carboxylic acid (5-fluoro-4-methyl-thiazol-2-yl)-amide Step 4: 6,2'-Dimethyl-[4,4']bipyridinyl-2-carboxylic acid (5-fluoro-4-methyl-thiazol-2-yl)-amide The title compound, was prepared from 6,2-Dimethyl-[4,4]bipyridinyl-2-carboxylic acid ethyl ester in accordance with the general method of example 26, step 6 using 5-Fluoro-4-methyl-thiazol-2-ylamine instead of 3-Chloroaniline to yield the final compound as a light brown solid, MS (ISP): m/e=343.0 $(M+H)^+$.

Example 202

6,2'-Dimethyl-[4,4']bipyridinyl-2-carboxylic acid (5-fluoro-thiazol-2-yl)-amide

The title compound, was prepared from 6,2-Dimethyl-[4,4]bipyridinyl-2-carboxylic acid ethyl ester in accordance with the general method of example 26, step 6 using 5-Fluoro-thiazol-2-ylamine instead of 3-Chloroaniline to yield the final compound as an off-white crystalline solid, MS (ISP): m/e=329.2 $(M+H)^+$.

Example 203

5-Fluoro-6'-methyl-[3,4']bipyridinyl-2'-carboxylic acid (4-methoxymethyl-thiazol-2-yl)-amide The title compound, was prepared from 5-Fluoro-6'-methyl-[3,4']bipyridinyl-2'-carboxylic acid ethyl ester in accordance with the general method of example 26, step 6 using 4-Methoxymethyl-thiazol-2-ylamine instead of 3-Chloroaniline to yield the final compound as a off-white solid, MS (ISP): m/e=359.1 $(M+H)^+$.

Example 204

5-Fluoro-6'-methyl-[3,4']bipyridinyl-2'-carboxylic acid (4-cyanomethyl-thiazol-2-yl)-amide The title compound, was prepared from 5-Fluoro-6'-methyl-[3,4']bipyridinyl-2'-carboxylic acid ethyl ester in accordance with the general method of example 26, step 6 using (2-Amino-thiazol-4-yl)-acetonitrile instead of 3-Chloroaniline to yield the final compound as a light yellow solid, MS (ISP): m/e=354.1 $(M+H)^+$.

Example 205

5-Fluoro-6'-methyl-[3,4']bipyridinyl-2'-carboxylic acid (5-fluoro-thiazol-2-yl)-amide The title compound, was prepared from 5-Fluoro-6'-methyl-[3,4']bipyridinyl-2'-carboxylic acid ethyl ester in accordance with the general method of example 26, step 6 using 5-Fluoro-thiazol-2-ylamine instead of 3-Chloroaniline to yield the final compound as a light yellow crystalline solid, MS (ISP): m/e=333.1 $(M+H)^+$.

Preparation of Pharmaceutical Compositions Comprising Compounds of the Invention Example I Tablets of the following composition are produced in a conventional manner:

|  | mg/Tablet |
|---|---|
| Active ingredient | 100 |
| Powdered. lactose | 95 |
| White corn starch | 35 |
| Polyvinylpyrrolidone | 8 |
| Na carboxymethylstarch | 10 |
| Magnesium stearate | 2 |
| Tablet weight | 250 |

Example II

Tablets of the following composition are produced in a conventional manner:

|  | mg/Tablet |
| --- | --- |
| Active ingredient | 200 |
| Powdered. lactose | 100 |
| White corn starch | 64 |
| Polyvinylpyrrolidone | 12 |
| Na carboxymethylstarch | 20 |
| Magnesium stearate | 4 |
| Tablet weight | 400 |

Example III

Capsules of the following composition are produced:

|  | mg/Capsule |
| --- | --- |
| Active ingredient | 50 |
| Crystalline. lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatine capsules of suitable size.

The invention claimed is:
1. A compound of formula (I)

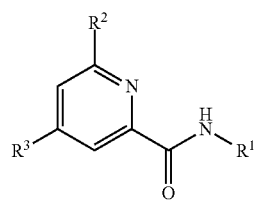

(I)

wherein
$R^1$ is a 5-member ring of formula (II):

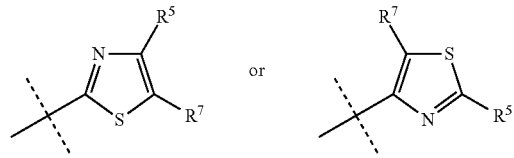

(II)

$R^2$ is $C_1$-$C_7$-alkyl;
$R^3$ is aryl or is heteroaryl selected from the group consisting of imidazolyl, oxazolyl, thiazolyl, pyrazinyl, pyrrolyl, pyridinyl, pyrimidinyl, indolyl, isoquinolinyl, carbazol-9-yl, furanyl, benzofuranyl, benzo[1,2,3]thiadiazolyl, benzo[b]thiophenyl, 9H-thioxanthenyl, and thieno[2,3-c]pyridinyl
each of which is optionally substituted by one or more substituents selected from the group consisting of CN, Cl, F, Br, $CF_3$, $CHF_2$, $C_1$-$C_7$alkyl, —O—$C_1$-$C_7$-alkyl, —(CO)—$R^b$, —$(CH_2)_m$—$R^c$, —NH—(CO)—$C_1$-$C_7$-alkyl, —O—$CH_2$F, —O—$CHF_2$, —S(O)$_2$—$R^d$, and —$NR^gR^h$ or wherein the heteroaryl is optionally substituted by $C_1$-$C_7$-alkyl;
$R^5$ is H, —OH, Cl, F, Br, CN, $CF_3$, $CHF_2$, $C_1$-$C_7$-alkyl, —$C_3$-$C_6$-cycloalkyl, —O—(CO)—$C_1$-$C_7$-alkyl, —$(CH_2)_m$—$R^e$, or —(CO)—$NR^iR^j$;
$R^7$ is H, Cl, F, CN or $C_1$-$C_7$-alkyl;
$R^b$ is $C_1$-$C_7$-alkyl, $NR^gR^h$ or —O—$C_1$-$C_7$-alkyl;
$R^c$ is —OH, —$NR^gR^h$ or NH—(CO)—O—$C_1$-$C_7$-alkyl;
$R^d$ is $C_1$-$C_7$-alkyl, —$NR^gR^h$, —NH—$C_1$-$C_7$-alkyl or —N-di($C_1$-$C_7$-alkyl);
$R^e$ is —OH, $CH_2$F, $CHF_2$, $CF_3$, CN, $C_1$-$C_7$-alkyl, $C_1$-$C_7$-alkoxy, —(CO)—$NR^iR^j$ or —O—(CO)—$C_1$-$C_7$-alkyl;
$R^g$ and $R^h$ are each independently H, $C_1$-$C_7$-alkyl, $C_3$-$C_6$-cycloalkyl, $C_3$-$C_8$-alkenyl, phenyl, benzyl, or —(CO)—$R^i$ or $R^g$ and $R^h$ can also, together with the nitrogen atom to which they are attached, form a 5- to 7-membered heterocyclic or heteroaryl ring optionally substituted with 1 or 2 OH;
$R^i$ and $R^j$ are each independently H or $C_1$-$C_7$alkyl;
R' is —$NR^gR^h$, —NH—$C_1$-$C_7$-alkyl, $C_1$-$C_7$-alkyl, or $C_1$-$C_7$-alkoxy;
m is 1 to 4;
or a pharmaceutically acceptable salt thereof.

2. A compound of formula (I')

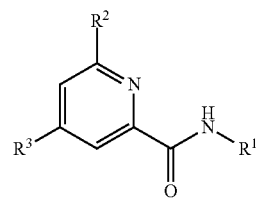

(I')

wherein
$R^1$ is a 5-membered ring of formula (II'):

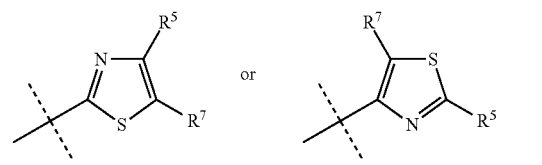

(II')

$R^2$ is $C_1$-$C_7$-alkyl;
$R^3$ is aryl or is heteroaryl selected from the group consisting of imidazolyl, oxazolyl, thiazolyl, pyrazinyl, pyrrolyl, pyridinyl, pyrimidinyl, indolyl, isoquinolinyl, carbazol-9-yl, furanyl, benzofuranyl, benzo[1,2,3]thiadiazolyl, benzo[b]thiophenyl, 9H-thioxanthenyl, and thieno[2,3-c]pyridinyl
each of which is optionally substituted by one or more CN, Cl, F, Br, $CF_3$, $CHF_2$, —O—$C_1$-$C_7$-alkyl, —(CO)—$R^b$, —$(CH_2)_m$—$R^c$, —NH—(CO)—$C_1$-

C₇-alkyl, —O—CH₂F, —O—CHF₂, —O—CF₃, —S(O)₂—R$^d$, or —NR$^g$R$^h$ or wherein the heteroaryl is optionally substituted by C₁-C₇-alkyl;

R⁵ is H, —OH, Cl, F, Br, CN, CF₃, CHF₂, C₁-C₇-alkyl, —C₃-C₆-cycloalkyl —O—(C₁-C₇-alkyl or —(CH₂)$_m$—R$^g$;

R⁷ is H or F;

R$^b$ is C₁-C₇-alkyl, —NR$^g$R$^h$ or —O—C₁-C₇-alkyl;

R$^c$ is —OH, —NR$^g$R$^h$ or NH—(CO)—O—C₁-C₇-alkyl;

R$^d$ is C₁-C₇-alkyl, —NR$^g$R$^h$, —NH—C₁-C₇-alkyl or —N-di(C₁-C₇alkyl);

R$^e$ is —OH, CH₂F, CHF₂, CF₃ or —O—(CO)—C₁-C₇-alkyl;

R$^g$ and R$^h$ are each independently H, C₁-C₇-alkyl, C₃-C₈-cycloalkyl, C₃-C₈-alkenyl, phenyl, benzyl, or —(CO)—R' or R$^g$ and R$^h$ can also, together with the nitrogen atom to which they are attached, form 5- to 7-membered heterocyclic or heteroaryl ring optionally substituted with 1 or 2 OH;

R' is NR$^g$R$^h$, —NH—C₁-C₇-alkyl, C₁-C₇-alkyl, or C₁-C₇-alkoxy;

m is 1 to 4;

or a pharmaceutically acceptable salt thereof.

3. The compound of claim 1 wherein:

R² is C₁-C₇-alkyl;

R³ is aryl or is heteroaryl selected from the group consisting of imidazolyl, oxazolyl, thiazolyl, pyrazinyl, pyrrolyl, pyridinyl, pyrimidinyl, indolyl, isoquinolinyl, carbazol-9-yl, furanyl, benzofuranyl, benzo[1,2,3]thiadiazolyl, benzo[b]thiophenyl, 9H-thioxanthenyl, and thieno[2,3-c]pyridinyl each of which is optionally substituted by one or more substituents independently selected from the group consisting of CN, Cl, F, CF₃, C₁-C₇-alkyl, —O—C₁-C₇-alkyl, —(CH₂)$_m$—R$^c$, —O—CF₃, and —S(O)₂—R$^d$;

R⁵ is H, Cl, CN, CF₃, CHF₂, C₁-C₇alkyl, C₃-C₆-cycloalkyl, —O(CO)—C₁-C₇-alkyl, —(CH₂)$_m$—R$^e$ or —(CO)—NR$^i$R$^j$;

R⁶ is C₁-C₇-alkyl or —(CH₂)$_m$—R$^g$;

R⁷ is H, Cl, F, CN, or C₁-C₇-alkyl;

R$^c$ is OH;

R$^d$ C₁-C₇-alkyl;

R$^e$ is —CF₃, CN, C₁-C₇alkoxy, —O(CO)—C₁-C₇alkyl or —(CO)—NR$^i$R$^j$;

R$^i$ and R$^j$ are each independently H or C₁-C₇-alkyl; and m is 1;

or a pharmaceutically acceptable salt thereof.

4. The compound of claim 1 having formula (Ia)

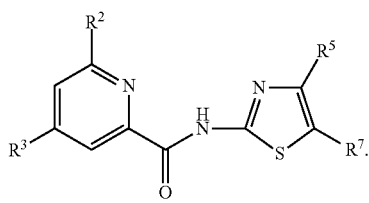

(Ia)

5. The compound of claim 4 selected from the group consisting of 4-(3-Fluoro-phenyl)-6-methyl-pyridine-2-carboxylic acid (4-methyl-thiazol-2-yl)-amide;

4-(3,5-Difluoro-phenyl)-6-methyl-pyridine-2-carboxylic acid (4-methyl-thiazol-2-yl)-amide;

4-(3-Cyano-phenyl)-6-methyl-pyridine-2-carboxylic acid (4-methyl-thiazol-2-yl)-amide;

6-Chloro-6'-methyl-[3,4']bipyridinyl-2'-carboxylic acid (4-methyl-thiazol-2-yl)-amide;

4-(2,5-Difluoro-phenyl)-6-methyl-pyridine-2-carboxylic acid (4-methyl-thiazol-2-yl)-amide;

4-(3-Methoxy-phenyl)-6-methyl-pyridine-2-carboxylic acid (4-methyl-thiazol-2-yl)-amide;

6-Methyl-4-(3-trifluoromethoxy-phenyl)-pyridine-2-carboxylic acid (4-methyl-thiazol-2-yl)-amide;

4-(3-Methanesulfonyl-phenyl)-6-methyl-pyridine-2-carboxylic acid (4-methyl-thiazol-2-yl)-amide;

4-(4-Methoxy-phenyl)-6-methyl-pyridine-2-carboxylic acid (4-methyl-thiazol-2-yl)-amide;

4-(3,4-Difluoro-phenyl)-6-methyl-pyridine-2-carboxylic acid (4-methyl-thiazol-2-yl)-amide; and 6-Methyl-4-(3,4,5-trifluoro-phenyl)-pyridine-2-carboxylic acid (4-methyl-thiazol-2-yl)-amide.

6. The compound of claim 4 selected from the group consisting of 4-(4-Cyano-phenyl)-6-methyl-pyridine-2-carboxylic acid (4-methyl-thiazol-2-yl)-amide;

4-(2-Methoxy-phenyl)-6-methyl-pyridine-2-carboxylic acid (4-methyl-thiazol-2-yl)-amide;

4-(2-Chloro-phenyl)-6-methyl-pyridine-2-carboxylic acid (4-methyl-thiazol-2-yl)-amide;

4-(3-Hydroxymethyl-phenyl)-6-methyl-pyridine-2-carboxylic acid (4-methyl-thiazol-2-yl)-amide;

6'-Methyl-[3,4']bipyridinyl-2'-carboxylic acid (4-methyl-thiazol-2-yl)-amide;

4-(3,5-Dichloro-phenyl)-6-methyl-pyridine-2-carboxylic acid (4-methyl-thiazol-2-yl)-amide;

6-Methyl-4-pyrimidin-5-yl-pyridine-2-carboxylic acid (4-methyl-thiazol-2-yl)-amide;

5-Fluoro-6'-methyl-[3,4']bipyridinyl-2'-carboxylic acid (4-methyl-thiazol-2-yl)-amide;

4-(4-Fluoro-phenyl)-6-methyl-pyridine-2-carboxylic acid (4-methyl-thiazol-2-yl)-amide;

6-(3,5-Difluoro-phenyl)-2-methyl-pyrimidine-4-carboxylic acid (4-methyl-thiazol-2-yl)-amide; and 2-Methyl-6-pyridin-3-yl-pyrimidine-4-carboxylic acid (4-methyl-thiazol-2-yl)-amide.

7. The compound of claim 4 selected from the group consisting of 4-(2,5-Dimethyl-2H-pyrazol-3-yl)-6-methyl-pyridine-2-carboxylic acid (4-methyl-thiazol-2-yl)-amide;

2'-Chloro-6-methyl-[4,4']bipyridinyl-2-carboxylic acid (4-methyl-thiazol-2-yl)-amide;

6'-Methyl-[2,4']bipyridinyl-2'-carboxylic acid (4-methyl-thiazol-2-yl)-amide;

6-Methyl-4-(3-trifluoromethyl-phenyl)-pyridine-2-carboxylic acid (4-methyl-thiazol-2-yl)-amide;

2-Chloro-6'-methyl-[3,4']bipyridinyl-2'-carboxylic acid (4-methyl-thiazol-2-yl)-amide;

5-Cyano-6'-methyl-[3,4']bipyridinyl-2'-carboxylic acid (4-methyl-thiazol-2-yl)-amide;

4-(3,5-Dimethyl-isoxazol-4-yl)-6-methyl-pyridine-2-carboxylic acid (4-methyl-thiazol-2-yl)-amide;

4,6'-Dimethyl-[3,4']bipyridinyl-2'-carboxylic acid (4-methyl-thiazol-2-yl)-amide;

5-Methoxy-6'-methyl-[3,4']bipyridinyl-2'-carboxylic acid (4-methyl-thiazol-2-yl)-amide;

6-Fluoro-6'-methyl-[3,4']bipyridinyl-2'-carboxylic acid (4-methyl-thiazol-2-yl)-amide; and 2'-Chloro-6-methyl-[4,4']bipyridinyl-2-carboxylic acid (4-methyl-thiazol-2-yl)-amide.

8. The compound of claim 4 selected from the group consisting of
- 4-(3,5-Difluoro-phenyl)-6-methyl-pyridine-2-carboxylic acid (4-trifluoromethyl-thiazol-2-yl)-amide;
- 5-Fluoro-6'-methyl-[3,4']bipyridinyl-2'-carboxylic acid (4-trifluoromethyl-thiazol-2-yl)-amide;
- 4-(3-Fluoro-phenyl)-6-methyl-pyridine-2-carboxylic acid (4-trifluoromethyl-thiazol-2-yl)-amide;
- 4-(3-Cyano-phenyl)-6-methyl-pyridine-2-carboxylic acid (4-trifluoromethyl-thiazol-2-yl)-amide;
- 4-(2-Chloro-phenyl)-6-methyl-pyridine-2-carboxylic acid (4-trifluoromethyl-thiazol-2-yl)-amide;
- 6'-Methyl-[3,4']bipyridinyl-2'-carboxylic acid (4-trifluoromethyl-thiazol-2-yl)-amide;
- 2'-Chloro-6-methyl-[4,4']bipyridinyl-2-carboxylic acid (4-trifluoromethyl-thiazol-2-yl)-amide;
- 4-(2,5-Dimethyl-2H-pyrazol-3-yl)-6-methyl-pyridine-2-carboxylic acid (4-trifluoromethyl-thiazol-2-yl)-amide;
- 6'-Methyl-[3,4']bipyridinyl-2'-carboxylic acid (4-difluoromethyl-thiazol-2-yl)-amide; and
- 2'-Chloro-6-methyl-[4,4']bipyridinyl-2-carboxylic acid (4-difluoromethyl-thiazol-2-yl)-amide.

9. A compound selected from the group consisting of
- 4-(3-Chloro-4-fluoro-phenyl)-3,6-dimethyl-pyridine-2-carboxylic acid (4-methyl-thiazol-2-yl)-amide;
- 4-(3,5-Difluoro-phenyl)-3,6-dimethyl-pyridine-2-carboxylic acid (4-methyl-thiazol-2-yl)-amide;
- 5-Fluoro-3',6'-dimethyl-[3,4']bipyridinyl-2'-carboxylic acid (4-methyl-thiazol-2-yl)-amide;
- 4-(4-Fluoro-phenyl)-3,6-dimethyl-pyridine-2-carboxylic acid (4-methyl-thiazol-2-yl)-amide;
- 3',6'-Dimethyl-[3,4']bipyridinyl-2'-carboxylic acid (4-methyl-thiazol-2-yl)-amide;
- 3,6-Dimethyl-4-pyrimidin-5-yl-pyridine-2-carboxylic acid (4-methyl-thiazol-2-yl)-amide; and
- 4-(3,4-Difluoro-phenyl)-3,6-dimethyl-pyridine-2-carboxylic acid (4-methyl-thiazol-2-yl)-amide.

10. A compound selected from the group consisting of
- 4-(2,5-Dimethyl-2H-pyrazol-3-yl)-3,6-dimethyl-pyridine-2-carboxylic acid (4-methyl-thiazol-2-yl)-amide;
- 2'-Chloro-3,6-dimethyl-[4,4']bipyridinyl-2-carboxylic acid (4-methyl-thiazol-2-yl)-amide;
- 3,6,2'-Trimethyl-[4,4']bipyridinyl-2-carboxylic acid (4-methyl-thiazol-2-yl)-amide;
- 6'-Methyl-5-trifluoromethyl-[3,4']bipyridinyl-2'-carboxylic acid (4-methyl-thiazol-2-yl)-amide;
- 2'-Fluoro-6-methyl-[4,4']bipyridinyl-2-carboxylic acid (4-methyl-thiazol-2-yl)-amide;
- 6-Methyl-4-pyrazin-2-yl-pyridine-2-carboxylic acid (4-methyl-thiazol-2-yl)-amide;
- 2,6'-Dimethyl-[3,4']bipyridinyl-2'-carboxylic acid (4-methyl-thiazol-2-yl)-amide;
- 6,2'-Dimethyl-[4,4']bipyridinyl-2-carboxylic acid (4-methyl-thiazol-2-yl)-amide;
- 6-Methyl-2-trifluoromethyl-[4,4']bipyridinyl-2-carboxylic acid (4-methyl-thiazol-2-yl)-amide;
- 2'-Cyano-6-methyl-[4,4']bipyridinyl-2-carboxylic acid (4-methyl-thiazol-2-yl)-amide; and
- 6'-Cyano-6,2'-dimethyl-[4,4']bipyridinyl-2-carboxylic acid (4-methyl-thiazol-2-yl)-amide.

11. The compound of claim 4 selected from the group consisting of
- 2'-Chloro-5'-fluoro-6-methyl-[4,4']bipyridinyl-2-carboxylic acid (4-methyl-thiazol-2-yl)-amide;
- 5,6'-Dimethyl-[3,4']bipyridinyl-2'-carboxylic acid (4-methyl-thiazol-2-yl)-amide;
- 4-(3,5-Difluoro-phenyl)-6-methyl-pyridine-2-carboxylic acid (4-cyanomethyl-thiazol-2-yl)-amide;
- 4-(3,5-Difluoro-phenyl)-6-methyl-pyridine-2-carboxylic acid (4-difluoromethyl-thiazol-2-yl)-amide;
- 4-(3,5-Difluoro-phenyl)-6-methyl-pyridine-2-carboxylic acid (4-cyano-thiazol-2-yl)-amide;
- 4-(3,5-Difluoro-phenyl)-6-methyl-pyridine-2-carboxylic acid (4-methoxymethyl-thiazol-2-yl)-amide;
- 5-Fluoro-6'-methyl-[3,4']bipyridinyl-2'-carboxylic acid (4-difluoromethyl-thiazol-2-yl)-amide;
- 5-Fluoro-6'-methyl-[3,4']bipyridinyl-2'-carboxylic acid (4-cyano-thiazol-2-yl)-amide;
- 5-Fluoro-6'-methyl-[3,4']bipyridinyl-2'-carboxylic acid (4-cyclopentyl-thiazol-2-yl)-amide;
- 6,2'-Dimethyl-[4,4']bipyridinyl-2-carboxylic acid (4-cyano-thiazol-2-yl)-amide; and
- 6,2'-Dimethyl-[4,4']bipyridinyl-2-carboxylic acid (4-methoxymethyl-thiazol-2-yl)-amide.

12. The compound of claim 4 selected from the group consisting of
- 6,2'-Dimethyl-[4,4']bipyridinyl-2-carboxylic acid (4-methyl-thiazol-2-yl)-amide;
- 2-{[4-(3,5-Difluoro-phenyl)-6-methyl-pyridine-2-carbonyl]-amino}-thiazole-4-carboxylic acid methyl ester;
- 4-(3,5-Difluoro-phenyl)-6-methyl-pyridine-2-carboxylic acid (4-methylcarbamoyl-thiazol-2-yl)-amide;
- 4-(3,5-Difluoro-phenyl)-6-methyl-pyridine-2-carboxylic acid (4-methoxymethyl-thiazol-2-yl)-amide;
- 6,2'-Dimethyl-[4,4']bipyridinyl-2-carboxylic acid (4-methoxymethyl-thiazol-2-yl)-amide;
- 4-(3,5-Difluoro-phenyl)-6-methyl-pyridine-2-carboxylic acid (4-methoxymethyl-thiazol-2-yl)-amide;
- 6,2'-Dimethyl-[4,4']bipyridinyl-2-carboxylic acid (4-methoxymethyl-thiazol-2-yl)-amide;
- 4-(3,5-Difluoro-phenyl)-6-methyl-pyridine-2-carboxylic acid (5-methyl-thiazol-2-yl)-amide;
- 5-Fluoro-6'-methyl-[3,4']bipyridinyl-2'-carboxylic acid (4-methoxymethyl-thiazol-2-yl)-amide;
- 5-Fluoro-6'-methyl-[3,4']bipyridinyl-2'-carboxylic acid (4-cyanomethyl-thiazol-2-yl)-amide; and
- 5-Fluoro-6'-methyl-[3,4']bipyridinyl-2'-carboxylic acid (5-fluoro-thiazol-2-yl)-amide.

13. The compound of claim 1 having formula (Ib)

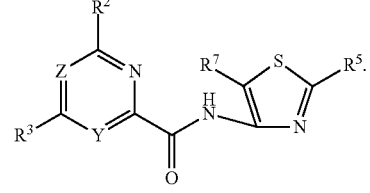

(Ib)

14. The compound of claim 13 selected from the group consisting of
- 4-(3,5-Dichloro-phenyl)-6-methyl-pyridine-2-carboxylic acid (2-methyl-thiazol-4-yl)-amide;
- 4-(3-Chloro-4-fluoro-phenyl)-6-methyl-pyridine-2-carboxylic acid (2-methyl-thiazol-4-yl)-amide;
- 4-(3,4-Difluoro-phenyl)-6-methyl-pyridine-2-carboxylic acid (2-methyl-thiazol-4-yl)-amide;
- 6-(3,5-Difluoro-phenyl)-2-methyl-pyrimidine-4-carboxylic acid (2-methyl-thiazol-4-yl)-amide;
- 5-Methoxy-6'-methyl-[3,4']bipyridinyl-2'-carboxylic acid (2-methyl-thiazol-4-yl)-amide;

6'-Methyl-[3,4']bipyridinyl-2'-carboxylic acid (2-methyl-thiazol-4-yl)-amide;
5-Fluoro-6'-methyl-[3,4']bipyridinyl-2'-carboxylic acid (2-methyl-thiazol-4-yl)-amide;
4-(4-Fluoro-phenyl)-6-methyl-pyridine-2-carboxylic acid (2-methyl-thiazol-4-yl)-amide;
4-(3,5-Difluoro-phenyl)-6-methyl-pyridine-2-carboxylic acid (2-methyl-thiazol-4-yl)-amide;
2'-Chloro-6-methyl-[4,4']bipyridinyl-2-carboxylic acid (2-methyl-thiazol-4-yl)-amide; and
4-(2,5-Dimethyl-2H-pyrazol-3-yl)-6-methyl-pyridine-2-carboxylic acid (2-methyl-thiazol-4-yl)-amide.

15. The compound of claim 13 selected from the group consisting of
4-(4-Fluoro-3-trifluoromethyl-phenyl)-6-methyl-pyridine-2-carboxylic acid (2-methyl-thiazol-4-yl)-amide;
4-(2,5-Dimethyl-2H-pyrazol-3-yl)-3,6-dimethyl-pyridine-2-carboxylic acid (2-methyl-thiazol-4-yl)-amide;
2'-Chloro-3,6-dimethyl-[4,4']bipyridinyl-2-carboxylic acid (2-methyl-thiazol-4-yl)-amide;
4-(3,5-Difluoro-phenyl)-3,6-dimethyl-pyridine-2-carboxylic acid (2-methyl-thiazol-4-yl)-amide;
3',6-Dimethyl-[3,4']bipyridinyl-2'-carboxylic acid (2-methyl-thiazol-4-yl)-amide;
4-(3-Chloro-4-fluoro-phenyl)-3,6-dimethyl-pyridine-2-carboxylic acid (2-methyl-thiazol-4-yl)-amide;
5-Fluoro-3',6'-dimethyl-[3,4']bipyridinyl-2'-carboxylic acid (2-methyl-thiazol-4-yl)-amide;
3,6-Dimethyl-4-pyrimidin-5-yl-pyridine-2-carboxylic acid (2-methyl-thiazol-4-yl)-amide;
4-(4-Fluoro-phenyl)-3,6-dimethyl-pyridine-2-carboxylic acid (2-methyl-thiazol-4-yl)-amide;
4-(3,4-Difluoro-phenyl)-3,6-dimethyl-pyridine-2-carboxylic acid (2-methyl-thiazol-4-yl)-amide; and
2'-Fluoro-6-methyl-[4,4]bipyridinyl-2-carboxylic acid (2-methyl-thiazol-4-yl)-amide.

16. A pharmaceutical composition comprising a therapeutically effective amount of a compound of formula I

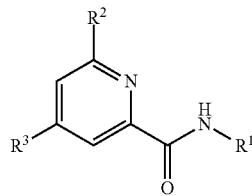

(I)

wherein
R$^1$ is a 5-membered ring of formula (II):

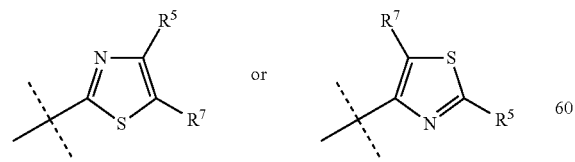

(II)

R$^2$ is C$_1$-C$_7$-alkyl;
R$^3$ is aryl or is heteroaryl selected from the group consisting of imidazolyl, oxazolyl, thiazolyl, pyrazinyl, pyrrolyl, pyridinyl, pyrimidinyl, indolyl, isoquinolinyl, carbazol-9-yl, furanyl, benzofuranyl, benzo[1,2,3]thiadiazolyl, benzo[b]thiophenyl, 9H-thioxanthenyl, and thieno[2,3-c]pyridinyl
each of which optionally substituted by one or more substituents selected from the group consisting of
CN, Cl, F, Br, CF$_3$, CHF$_2$, C$_1$-C$_7$-alkyl, —O—C$_1$-C$_7$-alkyl, —(CO)—R$^b$, —(CH$_2$)$_m$—R$^c$, —NH—(CO)—C$_1$-C$_7$-alkyl, —O—CH$_2$F, —O—CHF$_2$, —O—CF$_3$, S(O)$_2$—R$^d$, and —NR$^g$R$^h$ or wherein the heteroaryl is optionally substituted by C$_1$-C$_7$-alkyl;
R$^5$ is H, —OH, Cl, F, Br, CN, CF$_3$, CHF$_2$, C$_1$-C$_7$-alkyl, —C$_3$-C$_6$-cycloalkyl, —O—(CO)—C$_1$-C$_7$-alkyl, —(CH$_2$)$_m$—R$^a$, or —(CO)—NR$^i$R$^j$;
R$^7$ is H, Cl, F, CN or C$_1$-C$_7$-alkyl;
R$^b$ is C$_1$-C$_7$-alkyl, —NR$^g$R$^h$ or —O—C$_1$-C$_7$-alkyl;
R$^c$ is —OH, —NR$^g$R$^h$ or NH—(CO)—O—C$_1$-C$_7$-alkyl;
R$^d$ is C$_1$-C$_7$-alkyl, NR$^g$R$^h$, —NH—C$_1$-C$_7$-alkyl or —N-di(C$_1$-C$_7$-alkyl);
R$^e$ is —OH, CH$_2$F, CHF$_2$, CF$_3$, CN, C$_1$-C$_7$-alkyl, C$_1$-C$_7$-alkoxy, —(CO)—NR$^i$R$^j$ or —O—(CO)—C$_1$-C$_7$-alkyl;
each of which is optionally substituted by one or more substituents selected from the group consisting of
CN, Cl, F, Br, CF$_3$, CHF$_2$, C$_1$-C$_7$alkyl, —O—C$_1$-C$_7$alkyl, —(CO)—R$^b$, —(CH$_2$)$_m$—R$^c$, —NH—(CO)—C$_1$-C$_7$-alkyl, —O—CH$_2$F, —O—CHF$_2$, —O—CF$_3$, —S(O)$_2$—R$^d$, and —NR$^g$R$^h$ or wherein the heteroaryl is optionally substituted by C$_1$-C$_7$-alkyl;
R$^5$ is H, —OH, Cl, F, Br, CN, CF$_3$, CHF$_2$, C$_1$-C$_7$-alkyl, —C$_3$-C$_6$-cycloalkyl, —O—(CO)—C$_1$-C$_7$-alkyl, —(CH$_2$)$_m$—R$^a$, or —(CO)—NR$^i$R$^j$;
R$^7$ is H, Cl, F, CN or C$_1$-C$_7$-alkyl;
R$^b$ is C$_1$-C$_7$-alkyl, —NR$^g$R$^h$ or —O—C$_1$-C$_7$-alkyl;
R$^c$ is —OH, —NR$^g$R$^h$ or NH—(CO)—O—C$_1$-C$_7$-alkyl;
R$^d$ is C$_1$-C$_7$-alkyl, —NR$^g$R$^h$, —NH—C$_1$-C$_7$-alkyl or —N-di(C$_1$-C$_7$-alkyl);
R$^e$ is —OH, CH$_2$F, CHF$_2$, CF$_3$, CN, C$_1$-C$_7$-alkyl, C$_1$-C$_7$-alkoxy, —(CO)—NR$^i$R$^j$ or —O—(CO)—C$_1$-C$_7$-alkyl;
R$^g$ and R$^h$ are each independently H, C$_1$-C$_7$-alkyl, C$_3$-C$_6$-cycloalkyl, C$_3$-C$_6$-alkenyl, phenyl, benzyl, or —(CO)—R$^i$ or R$^g$ and R$^h$ can also, together with the nitrogen atom to which they are attached, form a 5- to 7-membered heterocyclic or heteroaryl ring optionally substituted with 1 or 2 OH:
R$^i$ and R$^j$ are each independently H or C$_1$-C$_7$-alkyl;
R' is —NR$^g$R$^h$, —NH—C$_1$-C$_7$-alkyl, C$_1$-C$_7$-alkyl, or C$_1$-C$_7$-alkoxy;
m is 1 to 4; and
or a pharmaceutically acceptable salt thereof.

17. A pharmaceutical composition comprising a therapeutically effective amount of a compound of formula (I')

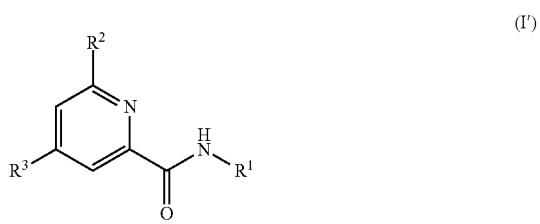

(I')

wherein
R¹ is a 5-membered ring of formulae (II')

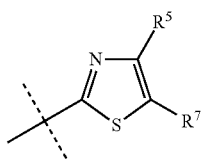 or 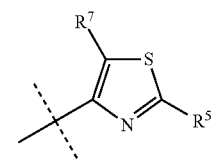  (II')

R² si $C_1$-$C_7$-alkyl;

R³ is aryl or is heteroaryl selected from the group consisting of imidazolyl, oxazolyl, thiazolyl, pyrazinyl, pyrrolyl, pyridinyl, pyrimidinyl, indolyl, isoquinolinyl, carbazol-9-yl, furanyl, benzofuranyl, benzo[1,2,3]thiadiazolyl, benzo[b]thiophenyl, 9H-thioxanthenyl, and thieno[2,3-c]pyridinyl
each of which is optionally substituted by one or more CN, Cl, F, Br, $CF_3$, $CHF_2$, —O—$C_1$-$C_7$-alkyl, —(CO)—$R^b$, —$(CH_2)_m$—$R^c$, —NH—(CO)—$C_1$-$C_7$-alkyl, —O—$CH_2F$, —O—$CHF_2$, —O—$CF_3$, —$S(O)_2$—$R^d$, or wherein the heteroaryl is optionally substituted by $C_1$-$C_7$-alkyl;

R⁵ is H, —OH, Cl, F, Br, CN, $CF_3$, $CHF_2$, $C_1$-$C_7$-alkyl, —$C_3$-$C_6$-cycloalkyl —O—(CO)—$C_1$-$C_7$-alkyl or —$(CH_2)_m$—$R^e$;

R⁷ is H or F;

$R^b$ is $C_1$-$C_7$-alkyl, —$NR^gR^h$ or —O—$C_1$-$C_7$-alkyl;

$R^c$ is —OH, —$NR^gR^h$ or NH—(CO)—O—$C_1$-$C_7$alkyl;

$R^d$ is $C_1$-$C_7$alkyl, —$NR^gR^h$, —NH—$C_1$-$C_7$-alkyl or —N-di($C_1$-$C_7$-alkyl);

$R^e$ is —OH, $CH_2F$, $CHF_2$, $CF_3$ or —O—(CO)—$C_1$-$C_7$-alkyl;

$R^g$ and $R^h$ are each independently H, $C_1$-$C_7$alkyl, $C_3$-$C_6$-cycloalkyl, $C_3$-$C_6$-alkenyl, phenyl, benzyl, or —(CO)—R' or $R^g$ and $R^h$ can also, together with the nitrogen atom to which hey are attached, form a 5- to 7-membered heterocyclic or heteroaryl ring optionally substituted with 1 or 2 OH;

R' is —$NR^gR^h$, —NH—$C_1$-$C_7$-alkyl, $C_1$-$C_7$-alkyl, or $C_1$-$C_7$-alkoxy;

m is 1 to 4;

or a pharmaceutically acceptable salt thereof and a pharmaceutically acceptable carrier.

18. A compound of formula (I)

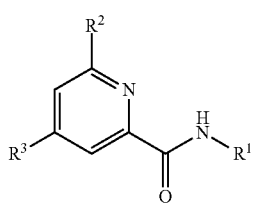  (I)

wherein
R¹ is a 6-membered ring of formula (III):

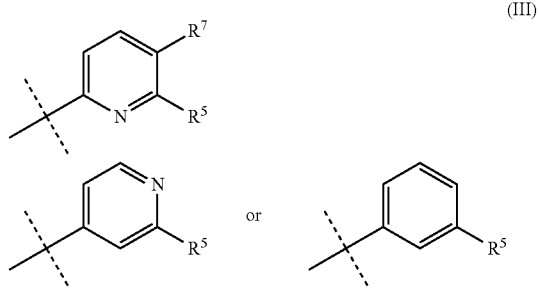  (III)

R² is $C_1$-$C_7$-alkyl;

R³ is heteroaryl selected from the group consisting of imidazolyl, oxazolyl, thiazolyl, pyrazinyl, pyrrolyl, pyridinyl, indolyl, isoquinolinyl, carbazol-9-yl, furanyl, benzofuranyl, benzo[1,2,3]thiadiazolyl, benzo[b]thiophenyl, 9H-thioxanthenyl, and thieno[2,3-c]pyridinyl

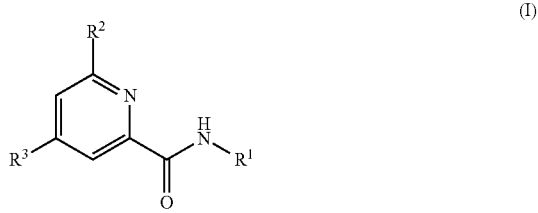  (I)

wherein
R¹ is a 6-membered ring of formula (III):

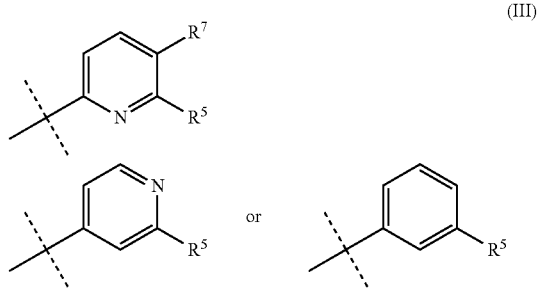  (III)

R² is $C_1$-$C_7$-alkyl;

R³ is heteroaryl selected from the group consisting of imidazolyl, oxazolyl, thiazolyl, pyrazinyl, pyrrolyl, pyridinyl, indolyl, isoquinolinyl, carbazol-9-yl, furanyl, benzofuranyl, benzo[1,2,3]thiadiazolyl, benzo[b]thiophenyl, 9H-thioxanthenyl, and thieno[2,3-c]pyridinyl
each of which is optionally substituted by one or more substituents selected from the group consisting of CN, Cl, F, Br, $CF_3$, $CHF_2$, $C_1$-$C_7$alkyl, —O—$C_1$-$C_7$-alkyl, —(CO)—$R^b$, —$(CH_2)_m$—$R^c$, —NH—(CO)—$C_1$-$C_7$-alkyl, —O—$CH_2F$, —O—$CHF_2$, —O—$CF_3$, —S(O)$_2$—R$^d$, and —NR$^g$R$^h$ or wherein the heteroaryl is optionally substituted by C$_1$-C$_7$-alkyl;

R$^5$ is H, —OH, Cl, F, Br, CN, CF$_3$, CHF$_2$, C$_1$-C$_7$-alkyl, —C$_3$-C$_6$-cycloalkyl, —O—(CO)—C$_1$-C$_7$-alkyl, —(CH$_2$)$_m$—R$^a$, or —(CO)—NR$^i$R$^j$;

R$^7$ is H, Cl, F, CN or C$_1$-C$_7$-alkyl;

R$^b$ is C$_1$-C$_7$-alkyl, —NR$^g$R$^h$ or —O—C$_1$-C$_7$-alkyl;

R$^c$ is —OH, —NR$^g$R$^h$ or NH—(CO)—O—C$_1$-C$_7$-alkyl or —N-di(C$_1$-C$_7$-alkyl);

R$^d$ is C$_1$-C$_7$-alkyl, —NR$^g$R$^h$, —NH—C$_1$-C$_7$-alkyl or —N-di(C$_1$-C$_7$-alkyl);

R$^e$ is —OH, CH$_2$F, CHF$_2$, CF$_3$, CN, C$_1$-C$_7$-alkyl, C$_1$-C$_7$-alkoxy, —(CO)—NR$^i$R$^j$ or —O—(CO)—C$_1$-C$_7$-alkyl;

R$^g$ and R$^h$ are each independently H, C$_1$-C$_7$-alkyl, C$_3$-C$_6$-cycloalkyl, C$_3$-C$_6$-alkenyl, phenyl, benzyl, or —(CO)—R' or R$^g$ and R$^h$ can also, together with the nitrogen atom to which they are attached, form a 5- to 7-membered heterocyclic or heteroaryl ring optionally substituted with 1 or 2 OH;

R$^i$ and R$^j$ are each independently H or C$_1$-C$_7$-alkyl;

R' is —NR$^g$R$^h$, —NH—C$_1$-C$_7$-alkyl, C$_1$-C$_7$-alkyl, or C$_1$-C$_7$-alkoxy;

m is 1 to 4;

or a pharmaceutically acceptable salt thereof and a pharmaceutically acceptable carrier.

19. A compound of formula (I')

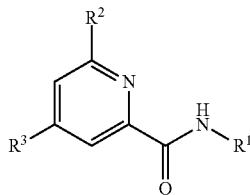

wherein

R$^1$ is a 6-membered ring of formula (III'):

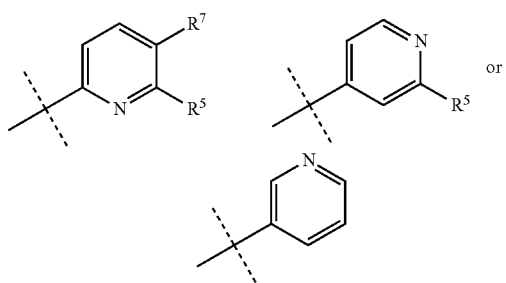

R$^2$ is C$_1$-C$_7$-alkyl;

R$^3$ is heteroaryl selected from the group consisting of imidazolyl, oxazolyl, thiazolyl, pyrazinyl, pyrrolyl, pyridinyl, indolyl, isoquinolinyl, carbazol-9-yl, furanyl, benzofuranyl, benzo[1,2,3]thiadiazolyl, benzo[b]thiophenyl, 9H-thioxanthenyl, and thieno[2,3-c]pyridinyl each of which is optimally substituted by one Or more CN, Cl, F, Br, CF$_3$, CHF$_2$, —O—C$_1$-C$_7$-alkyl, —(CO)—R$^b$, —(CH$_2$)$_m$—R$^c$, —NH—(CO)—C$_3$-C$_7$-alkyl, —O—CHF$_2$, —O—CF$_3$, —S(O)$_2$—R$^d$, or —NR$^g$R$^h$ or wherein the heteroaryl is optionally substituted by C$_1$-C$_7$-alkyl;

R$^5$ is H, —OH, Cl, F, Br, CN, CF$_3$, CHF$_2$, C$_1$-C$_7$-alkyl, —C$_3$-C$_5$-cycloalkyl —O—(CO)—C$_1$-C$_7$-alkyl or —(CH$_2$)$_m$—R$^e$;

R$^7$ is H or F;

R$^b$ is C$_1$-C$_7$-alkyl, —NR$^g$R$^h$ or —O—C$_1$-C$_7$-alkyl;

R$^c$ is —OH, —NR$^g$R$^h$ or NH—(CO)—O—C$_1$-C$_7$-alkyl;

R$^d$ is C$_1$-C$_7$alkyl, —NR$^g$R$^h$, —NH—C$_1$-C$_7$-alkyl or —N-di(C$_1$-C$_7$-alkyl);

R$^e$ is —OH, CH$_2$F, CHF$_2$, CF$_3$ or —O—(CO)—C$_1$-C$_7$-alkyl;

R$^g$ and R$^h$ are each independently H, C$_1$-C$_7$-alkyl, C$_3$-C$_6$cycloalkyl, C$_3$-C$_8$-alkenyl, phenyl, benzyl, or —(CO)—R' or R$^g$ and R$^h$ can also together with the nitrogen atom to which they are attached, form a 5- to 7-membered heterocyclic or heteroaryl ring optionally substituted with 1 or 2 OH;

R$^i$ and R$^j$ are each independently H or C$_1$-C$_7$alkyl;

R' is —NR$^g$R$^h$, —NH—C$_1$-C$_7$-alkyl, C$_1$-C$_7$-alkyl, or C$_1$-C$_7$alkoxy;

m is 1 to 4;

or a pharmaceutically acceptable salt thereof.

20. The compound of claim 18 having formula (Ie)

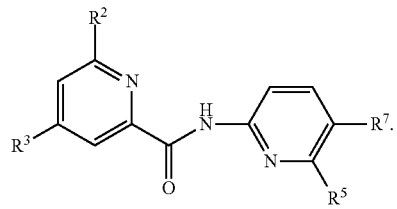

21. The compound of claim 20 selected from the group consisting of

6'-Methyl-[3,4']bipyridinyl-2'-carboxylic acid (6-methyl-pyridin-2-yl)-amide;

6'-Methyl-[3,4']bipyridinyl-2'-carboxylic acid (6-chloro-pyridin-2-yl)-amide;

5-Fluoro-3',6'-dimethyl-[3,4']bipyridinyl-2'-carboxylic acid (2-methyl-pyridin-4-yl)-amide;

3',6'-Dimethyl-[3,4']bipyridinyl-2'-carboxylic acid (2-methyl-pyridin-4-yl)-amide;

5-Fluoro-6'-methyl-[3,4']bipyridinyl-2'-carboxylic acid (5-chloro-pyridin-2-yl)amide;

2'-Chloro-6-methyl-[4,4']bipyridinyl-2-carboxylic acid (6-methyl-pyridin-2-yl)amide;

2'-Chloro-6-methyl-[4,4']bipyridinyl-2-carboxylic acid (5-chloro-pyridin-2-yl)amide; and 2'-Chloro-6-methyl-[4,4']bipyridinyl-2-carboxylic acid (5-methyl-pyridin-2-yl)amide.

22. The compound of claim 18 having formula (Ig)

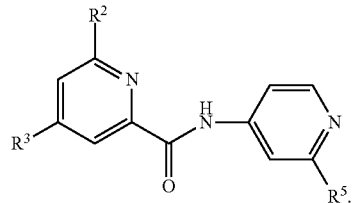

23. The compound of claim 22 selected from the group consisting of
- 4-(4-Fluoro-phenyl)-6-methyl-pyridine-2-carboxylic acid (2-methyl-pyridin-4-yl)-amide;
- 4-(4-Fluoro-phenyl)-6-methyl-pyridine-2-carboxylic acid (2-chloro-pyridin-4-yl)-amide;
- 5-Fluoro-6'-methyl-[3,4']bipyridinyl-2'-carboxylic acid (2-chloro-pyridin-4-yl)-amide;
- 4-(3,4-Difluoro-phenyl)-6-methyl-pyridine-2-carboxylic acid (2-chloro-pyridin-4-yl)-amide;
- 6'-Methyl-[3,4']bipyridinyl-2'-carboxylic acid (2-chloro-pyridin-4-yl)-amide;
- 4-(3,5-Difluoro-phenyl)-6-methyl-pyridine-2-carboxylic acid (2-chloro-pyridin-4-yl)-amide;
- 4-(3-Chloro-4-fluoro-phenyl)-6-methyl-pyridine-2-carboxylic acid (2-chloro-pyridin-4-yl)-amide;
- 4-(3,4-Difluoro-phenyl)-6-methyl-pyridine-2-carboxylic acid (2-methyl-pyridin-4-yl)-amide; and
- 5-Fluoro-6'-methyl-[3,4']bipyridinyl-2'-carboxylic acid (2-methyl-pyridin-4-yl)-amide.

24. The compound of claim 22 selected from the group consisting of
- 4-(3-Chloro-4-fluoro-phenyl)-6-methyl-pyridine-2-carboxylic acid (2-methyl-pyridin-4-yl)-amide;
- 6'-Methyl-[3,4']bipyridinyl-2'-carboxylic acid (2-methyl-pyridin-4-yl)-amide;
- 4-(3,5-Difluoro-phenyl)-6-methyl-pyridine-2-carboxylic acid (2-methyl-pyridin-4-yl)-amide;
- 5-Cyano-6'-methyl-[3,4']bipyridinyl-2'-carboxylic acid (2-methyl-pyridin-4-yl)-amide;
- 4-(2,5-Dimethyl-2H-pyrazol-3-yl)-6-methyl-pyridine-2-carboxylic acid (5-chloro-pyridin-2-yl)-amide;
- 4-(3,5-Difluoro-phenyl)-6-methyl-pyridine-2-carboxylic acid (5-chloro-pyridin-2-yl)-amide;
- 4-(3-Chloro-4-fluoro-phenyl)-6-methyl-pyridine-2-carboxylic acid (5-chloro-pyridin-2-yl)-amide;
- 6'-Methyl-[3,4']bipyridinyl-2'-carboxylic acid (5-chloro-pyridin-2-yl)-amide;
- 2'-Cyano-6-methyl-[4,4']bipyridinyl-2-carboxylic acid (2-methyl-pyridin-4-yl)-amide;
- 6'-Cyano-6,2'-dimethyl-[4,4']bipyridinyl-2-carboxylic acid (2-methyl-pyridin-4-yl)-amide; and
- 6,2'-Dimethyl-[4,4]bipyridinyl-2-carboxylic acid (2-methyl-pyridin-4-yl)-amide.

25. The compound of claim 22 selected from the group consisting of
- 2'-Chloro-6-methyl-[4,4']bipyridinyl-2-carboxylic acid (2-methyl-pyridin-4-yl)-amide;
- 6'-Cyano-6,2'-dimethyl-[4,4']bipyridinyl-2-carboxylic acid (2-chloro-pyridin-4-yl)-amide;
- 2'-Cyano-6-methyl-[4,4']bipyridinyl-2-carboxylic acid (2-chloro-pyridin-4-yl)-amide;
- 6,2'-Dimethyl-[4,4']bipyridinyl-2-carboxylic acid (2-chloro-pyridin-4-yl)-amide;
- 6,2',6'-Trimethyl-[4,4']bipyridinyl-2-carboxylic acid (2-chloro-pyridin-4-yl)-amide;
- 5,6'-Dimethyl-[3,4']bipyridinyl-2'-carboxylic acid (2-chloro-pyridin-4-yl)-amide;
- 2'-Chloro-6-methyl-[4,4']bipyridinyl-2-carboxylic acid (2-chloro-pyridin-4-yl)-amide;
- 6,2',5'-Trimethyl-[4,4']bipyridinyl-2-carboxylic acid (2-chloro-pyridin-4-yl)-amide; and
- 4-(3,5-Difluoro-phenyl)-6-methyl-pyridine-2-carboxylic acid (2-cyano-pyridin-4-yl)-amide.

26. The compound of claim 18 having formula (Ih)

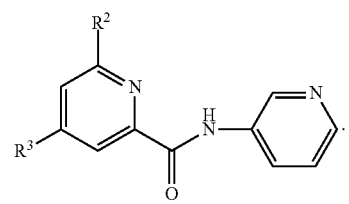

27. The compound of claim 26 which is 5-Fluoro-6'-methyl-[3,4']bipyridinyl-2'-carboxylic acid pyridin-3-ylamide.

28. A pharmaceutical composition comprising a therapeutically effective amount of a compound of formula I
$R^g$ and $R^h$ are each independently H, $C_1$-$C_7$-alkyl, $C_3$-$C_6$-cycloalkyl, $C_3$-$C_8$-alkenyl, phenyl, benzyl, or —(CO)—R' or $R^g$ and $R^h$ can also, together with the nitrogen atom to which they are attached, form a 5- to 7-membered heterocyclic or heteroaryl ring optionally substituted with 1 or 2 OH;
$R^i$ and $R^j$ are each independently H or $C_1$-$C_7$-alkyl;
R' is —$NR^gR^h$, —NH—$C_1$-$C_7$-alkyl, $C_1$-$C_7$-alkyl, or $C_1$-$C_7$-alkoxy;
m is 1 to 4;
or a pharmaceutically acceptable salt thereof and a pharmaceutically acceptable carrier.

29. A pharmaceutical composition comprising a therapeutically effective amount of a compound of formula (I')

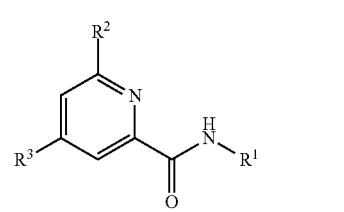

wherein
$R^1$ is 6-membered ring of formula (III')

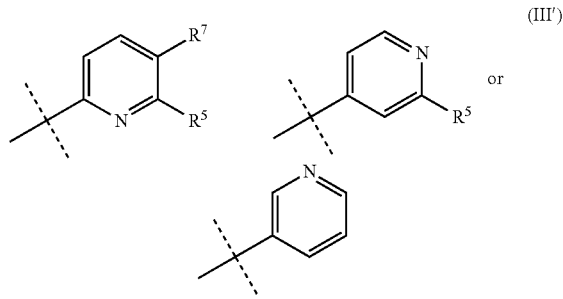

$R^2$ is $C_1$-$C_7$-alkyl;
$R^3$ is heteroaryl selected from the group consisting of imidazolyl, oxazolyl, thiazolyl, pyrazinyl, pyrrolyl, pyridinyl, indolyl, isoquinolinyl, carbazol-9-yl, furanyl, benzofuranyl, benzo[1,2,3]thiadiazolyl, benzo[b]thiophenyl, 9H-thioxanthenyl, and thieno[2,3-c]pyridinyl each of which is optionally substituted by one or more CN, Cl, F, Br, $CF_3$, $CHF_2$, $-O-C_1-C_7$-alkyl, $-(CO)-R^b$, $-(CH_2)_m-R^c$, $-NH-(CO)-C_1-C_7$-alkyl, $-O-CH_2F$, $-O-CHF_2$, $-O-CF_3$, $-S(O)_2-R^d$, or $-NR^gR^h$ or wherein the heteroaryl is optionally substituted by $C_1-C_7$-alkyl;

$R^5$ is H, $-OH$, Cl, F, Br, CN, $CF_3$, $CHF_2$, $C_1-C_7$-alkyl, $C_3-C_6$-cycloalkyl, $-O-(CO)-C_1-C_7$-alkyl or $-(CH_2)_m-R^e$;

$R^7$ is H or F;

$R^b$ is $C_1-C_7$-alkyl, $-NR^gR^h$ or $-O-C_1-C_7$-alkyl;

$R^c$ is $-OH$, $-NR^gR^h$ or $NH-(CO)-O-C_1-C_7$-alkyl;

$R^d$ is $C_1-C_7$-alkyl, $NR^gR^h$, $-NH-C_1-C_7$-alkyl or $-N$-di$(C_1-C_7$-alkyl);

$R^e$ is $-OH$, $CH_2F$, $CHF_2$, $CF_3$ or $-O-(CO)-C_1-C_7$-alkyl;

$R^g$ and $R^h$ are each independently H, $C_1-C_7$-alkyl, $C_3-C_6$-cycloalkyl, $C_3-C_6$-alkenyl, phenyl, benzyl, or $-(CO)-R'$ $R^g$ and $R^h$ can also, together with the nitrogen atom to which they are attached, form a 5- to 7-membered heterocyclic or heteroaryl ring optionally substituted with 1 or 2 OH;

$R^i$ and $R^j$ are each independently H or $C_1-C_7$-alkyl;

R' is $-NR^gR^h$, $-NH-C_1-C_7$-alkyl, $C_1-C_7$-alkyl, or $C_1-C_7$-alkoxy;

m is 1 to 4;

or a pharmaceutically acceptable salt thereof and a pharmaceutically acceptable carrier.

* * * * *